US007320958B2

(12) United States Patent
Rupar et al.

(10) Patent No.: US 7,320,958 B2
(45) **Date of Patent: *Jan. 22, 2008**

(54) COLEOPTERAN-TOXIC POLYPEPTIDE COMPOSITIONS

(75) Inventors: Mark J. Rupar, Wilmington, DE (US); William P. Donovan, Levittown, PA (US); Chih-Rei Chu, Exton, PA (US); Elizabeth Pease, Danville, PA (US); Yuping Tan, Fremont, CA (US); Annette C. Slaney, Burlington, NJ (US); Thomas M. Malvar, Troy, MO (US); James A. Baum, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/485,621

(22) Filed: Jul. 12, 2006

(65) Prior Publication Data

US 2006/0253925 A1 Nov. 9, 2006

Related U.S. Application Data

(62) Division of application No. 10/408,692, filed on Apr. 7, 2003, now Pat. No. 7,078,592, which is a division of application No. 09/563,269, filed on May 3, 2000, now Pat. No. 6,555,655.

(60) Provisional application No. 60/172,240, filed on May 4, 1999.

(51) Int. Cl.
*A01N 37/18* (2006.01)
*C07K 14/325* (2006.01)

(52) U.S. Cl. .......................................... 514/2; 530/350

(58) Field of Classification Search ..................... None
See application file for complete search history.

(56) References Cited

U.S. PATENT DOCUMENTS

| | | | |
|---|---|---|---|
| 6,127,180 A | 10/2000 | Narva et al. | |
| 6,197,312 B1 | 3/2001 | Peak et al. ............... | 424/250.1 |

FOREIGN PATENT DOCUMENTS

| | | |
|---|---|---|
| EP | 0 454 485 | 10/1990 |
| WO | WO 93 14205 | 7/1993 |
| WO | WO 97/40162 | 10/1997 |

OTHER PUBLICATIONS

Ely, S., The Engineering of Plants to Express *Bacillus thuringiensis* δ-Endotoxins, *Bacillus thuringiensis*, An Environmental Biopesticide: Theory and Practice, Edited by P.F. Entwistle et al., XP-002054693, pp. 105-124 (1993).

Donovan, W.P., et al., Characterization of Two Genes Encoding *Bacillus thuringiensis* Insecticidal Crystal Proteins Toxic to *Coleoptera Species*, Applied and Environmental Microbiology,XP-000876861, pp. 3921-3927 (1992).

Fidock et al., "Conservation of the *Plasmodium falciparum* Sporozoite Surface Protein Gene, STARP, in Field Isolates and Distinct Species of *Plasmodium," Molecular and Biochemicval Parasitology*, 67:255-267 (1994).

Yuan et al., GenBank Accession No. AJ000743 (1998).

Salomon et al., GenBank Accession No. S42303 (1993).

Morio et al., GenBank Accession No. C89791 (1998).

*Primary Examiner*—Anish Gupta
*Assistant Examiner*—Ronald T Niebauer
(74) *Attorney, Agent, or Firm*—Timothy K. Ball; Howrey LLP

(57) ABSTRACT

Disclosed are novel insecticidal polypeptides, and compositions comprising these polypeptides, peptide fragments thereof, and antibodies specific therefor. Also disclosed are vectors, transformed host cells, and transgenic plants that contain nucleic acid segments that encode the disclosed δ-endotoxin polypeptides. Also disclosed are methods of identifying related polypeptides and polynucleotides, methods of making and using transgenic cells comprising these polynucleotide sequences, as well as methods for controlling an insect population, such as Colorado potato beetle, southern corn rootworm and western corn rootworm, and for conferring to a plant resistance to a target insect species.

9 Claims, 3 Drawing Sheets

COLEOPTERAN-TOXIC POLYPEPTIDE COMPOSITIONS

Figure 1:
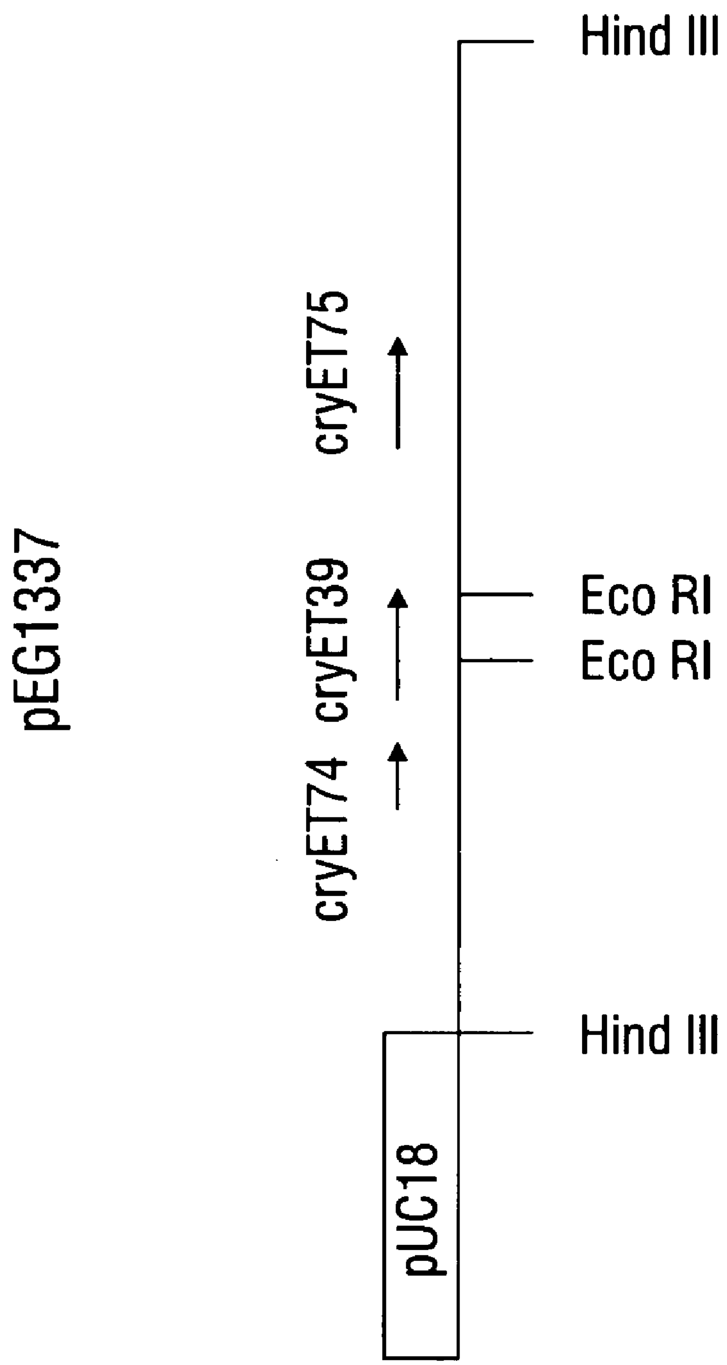

This application is a divisional of application Ser. No. 10/408,692, now U.S. Pat. No. 7,078,592, filed Apr. 7, 2003, which is a divisional of application Ser. No. 09/563,269, filed May 3, 2000, now U.S. Pat. No. 6,555,655, which claims the benefit of U.S. Provisional Application No. 60/172,240, filed May 4,1999.

1.0 BACKGROUND OF THE INVENTION

1.1 Field of the Invention

The present invention relates generally to the fields of molecular biology. More particularly, certain embodiments concern methods and compositions comprising DNA segments, and proteins derived from bacterial species. More particularly, it concerns novel genes from *Bacillus thuringiensis* encoding coleopteran-toxic crystal proteins. Various methods for making and using these DNA segments, DNA segments encoding synthetically-modified δ-endotoxin polypeptides, and native and synthetic crystal proteins are disclosed, such as, for example, the use of DNA segments as diagnostic probes and templates for protein production, and the use of proteins, fusion protein carriers and peptides in various immunological and diagnostic applications. Also disclosed are methods of making and using nucleic acid segments in the development of transgenic plant cells containing the polynucleotides disclosed herein.

1.2 Description of the Related Art

Because crops of commercial interest are often the target of insect attack, environmentally-sensitive methods for controlling or eradicating insect infestation are desirable in many instances. This is particularly true for farmers, nurserymen, growers, and commercial and residential areas which seek to control insect populations using eco-friendly compositions. The most widely used environmentally-sensitive insecticidal formulations developed in recent years have been composed of microbial pesticides derived from the bacterium *Bacillus thuringiensis. B. thuringiensis* is a Gram-positive bacterium that produces crystal proteins or inclusion bodies which are specifically toxic to certain orders and species of insects. Many different strains of *B. thuringiensis* have been shown to produce insecticidal crystal proteins. Compositions including *B. thuringiensis* strains which produce insecticidal proteins have been commercially-available and used as environmentally-acceptable insecticides because they are quite toxic to the specific target insect, but are harmless to plants and other non-targeted organisms.

1.2.1 δ-Endotoxins

δ-endotoxins are used to control a wide range of leaf-eating caterpillars and beetles, as well as mosquitoes. These proteinaceous parasporal crystals, also referred to as insecticidal crystal proteins, crystal proteins, Bt inclusions, crystalline inclusions, inclusion bodies, and Bt toxins, are a large collection of insecticidal proteins produced by *B. thuringiensis* that are toxic upon ingestion by a susceptible insect host. Over the past decade research on the structure and function of *B. thuringiensis* toxins has covered all of the major toxin categories, and while these toxins differ in specific structure and function, general similarities in the structure and function are assumed. Based on the accumulated knowledge of *B. thuringiensis* toxins, a generalized mode of action for *B. thuringiensis* toxins has been created and includes: ingestion by the insect, solubilization in the insect midgut (a combination stomach and small intestine), resistance to digestive enzymes sometimes with partial digestion actually "activating" the toxin, binding to the midgut cells, formation of a pore in the insect cells and the disruption of cellular homeostasis (English and Slatin, 1992).

One of the unique features of *B. thuringiensis* is its production of crystal proteins during sporulation which are specifically toxic to certain orders and species of insects. Many different strains of *B. thuringiensis* have been shown to produce insecticidal crystal proteins. Compositions including *B. thuringiensis* strains which produce proteins having insecticidal activity against lepidopteran and dipteran insects have been commercially available and used as environmentally-acceptable insecticides because they are quite toxic to the specific target insect, but are harmless to plants and other non-targeted organisms.

The mechanism of insecticidal activity of the *B. thuringiensis* crystal proteins has been studied extensively in the past decade. It has been shown that the crystal proteins are toxic to the insect only after ingestion of the protein by the insect. The alkaline pH and proteolytic enzymes in the insect mid-gut solubilize the proteins, thereby allowing the release of components which are toxic to the insect. These toxic components disrupt the mid-gut cells, cause the insect to cease feeding, and, eventually, bring about insect death. For this reason, *B. thuringiensis* has proven to be an effective and environmentally safe insecticide in dealing with various insect pests.

As noted by Höfte et al., (1989) the majority of insecticidal *B. thuringiensis* strains are active against insects of the order Lepidoptera, i.e. caterpillar insects. Other *B. thuringiensis* strains are insecticidally active against insects of the order Diptera, i.e., flies and mosquitoes, or against both lepidopteran and dipteran insects. In recent years, a few *B. thuringiensis* strains have been reported as producing crystal proteins that are toxic to insects of the order Coleoptera, i.e., beetles (Krieg et al., 1983; Sick et al., 1990; Donovan et al., 1992; Lambert et al., 1992a; 1992b).

1.2.2 Genes Encoding Crystal Proteins

Many of the δ-endotoxins are related to various degrees by similarities in their amino acid sequences. Historically, the proteins and the genes which encode them were classified based largely upon their spectrum of insecticidal activity. The review by Höfte and Whiteley (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins, and cryII genes encode CryII proteins that are toxic to both lepidopterans and dipterans. cryIII genes encode coleopteran-toxic CryIII proteins, while cryIV genes encode dipteran-toxic CryIV proteins.

Based on the degree of sequence similarity, the proteins were further classified into subfamilies; more highly related proteins within each family were assigned divisional letters such as CryIA, CryIB, CryIC, etc. Even more closely related proteins within each division were given names such as CryIC1, CryIC2, etc.

Recently, a new nomenclature was developed which systematically classified the Cry proteins based upon amino acid sequence homology rather than upon insect target specificities (Crickmore et al., 1998). The classification scheme for many known toxins, not including allelic variations in individual proteins, is summarized in Section 4.3.

1.2.3 Crystal Proteins Toxic to Coleopteran Insects

The cloning and expression of the cry3Bb gene has been described (Donovan et al., 1992). This gene encodes a 74-kDa protein having insecticidal activity against Coleopterans, such as Colorado potato beetle (CPB), and southern corn root worm (SCRW).

A *B. thuringiensis* strain, PS201T6, reported to have activity against western corn rootworm (WCRW, *Diabrotica virgifera virgifera*) was described in U.S. Pat. No. 5,436,002 (specifically incorporated herein by reference in its entirety). This strain also showed activity against *Musca domestica, Aedes aegypti*, and *Liriomyza trifoli*.

The cloning and expression of the cryET29 gene has also been described (Intl. Pat. Appl. Publ. Ser. No. WO 97/17507, 1997). This gene encodes a 25-kDa protein that is active against Coleopteran insects, particularly the CPB, SCRW, WCRW, and the cat flea, *Ctenocephalides felis*.

The cloning and expression of the cryET33 and cryET34 genes has been described (Intl. Pat. Appl. Publ. Ser. No. WO 97/17600, 1997). These genes encode proteins of ~30 and ~15 kDa, respectively, and are active against Coleopteran insects, particularly CPB larvae and the Japanese beetle (*Popillia japonica*).

The vip1A gene, which produces a vegetative, soluble, insecticidal protein, has also been cloned and sequenced (Intl. Pat. Appl. Publ. Ser. No. WO 96/10083, 1996). This gene encodes a protein of approximately 80 kDa, that is active against both WCRW and northern corn rootworm (NCRW).

Another endotoxin active against coleopteran insects, including WCRW, is Cry1Ia (Intl. Pat. Appl. Publ. Ser. No. WO 90/13651, 1990). The gene encoding this 81-kDa polypeptide has been cloned and sequenced.

Additional crystal proteins with toxicity towards the WCRW have been described (Intl. Pat. Appl. Publ. Ser. No. WO 97/40162, 1997). These proteins appear to function as binary toxins and show sequence similarity to mosquitocidal proteins isolated from *B. sphaericus*.

Certain strains of *B. sphaericus* are highly active against mosquito larvae, with many producing, upon sporulation, a crystalline inclusion composed of two protein toxins. The analysis of the genes encoding these proteins have been described by Baumann et al., (1988). The toxins are designated P51 and P42 on the basis of their predicted molecular masses of 51.4- and 41.9-kDa, respectively. The P42 protein alone is weakly active against mosquito larvae. The P51 protein has no mosquitocidal activity by itself. Both P51 and P42 are required for full insecticidal activity. There are no reports of the crystal proteins of *B. sphaericus* having activity on any insects other than mosquitos (for a recent review see Charles et al., 1996a; 1996b).

A second class of mosquitocidal protein toxins are produced by some strains of *B. sphaericus*. These proteins, known as Mtx toxins, are produced during vegetative growth and do not form a crystalline inclusion. The two Mtx toxins that have been identified, designated Mtx and Mtx2, have molecular masses of 100 and 30.8 kDa, respectively. The cloning and sequencing of the genes for these toxins, designated mtx and mtx2, has been described (Thanabalu et al., 1991, Thanabalu and Porter, 1995). The Mtx and Mtx2 proteins do not share sequence similarity to any other known insecticidal proteins, including the crystal proteins of *B. sphaericus* and *B. thuringiensis*.

2.0 SUMMARY OF THE INVENTION

The present invention provides novel insecticidal polypeptides and DNA sequences that encode them. For five of these polypeptides, their disimiliarity to the known crystal proteins indicates the existence of a new class or sub-class of *B. thuringiensis* crystal proteins, as they share less than 65% amino acid sequence identity with any of the presently known insecticidal polypeptides. The invention further provides novel polypeptides that when in combination, produce insecticidally-active crystal proteins. Also provided are transformed host cells, transgenic plants, vectors, and methods for making and using the novel polypeptides and polynucleotides.

In a first embodiment, the invention provides an isolated CryET69 polypeptide comprising at least 7 contiguous amino acids from SEQ ID NO:14. More preferably the polypeptide comprises at least 9 or at least 11 contiguous amino acids from SEQ ID NO:14. Still more preferably, the polypeptide comprises at least 13 or at least 15 contiguous amino acids from SEQ ID NO:14, and more preferably comprises at least 17 or at least 19 contiguous amino acids from SEQ ID NO:14. In an exemplary embodiment, the polypeptide comprises the sequence of SEQ ID NO:14. Such a polypeptide is preferably encoded by a nucleic acid segment that comprises an at least 45-basepair contiguous nucleotide sequence from SEQ ID NO:13, and more preferably is encoded by a nucleic acid segment that comprises an at least 90-basepair contiguous sequence from SEQ ID NO:13. More preferably still, such a polypeptide is encoded by a nucleic acid segment that comprises an at least 150-basepair contiguous sequence from SEQ ID NO:13. Exemplary polynucleotides encoding the insecticidal polypeptide comprise an at least 300-basepair contiguous nucleotide sequence from SEQ ID NO:13, and in one embodiment comprises the nucleotide sequence of SEQ ID NO:13.

Also disclosed and claimed is an isolated CryET84 polypeptide comprising at least 15 contiguous amino acids from SEQ ID NO:19. More preferably the polypeptide comprises at least 30 to 45 contiguous amino acids from SEQ ID NO:19. Still more preferably, the polypeptide comprises at least 45 to 90 contiguous amino acids from SEQ ID NO:19, and more preferably comprises at least 90 to 150 contiguous amino acids from SEQ ID NO:19. In an exemplary embodiment, the polypeptide comprises the sequence of SEQ ID NO:19. Such a polypeptide is preferably encoded by a nucleic acid segment that comprises an at least 45-basepair contiguous nucleotide sequence from SEQ ID NO:18, and more preferably is encoded by a nucleic acid segment that comprises an at least 90-basepair contiguous sequence from SEQ ID NO:18. More preferably still, such a polypeptide is encoded by a nucleic acid segment that comprises an at least 150-basepair contiguous sequence from SEQ ID NO:18. Exemplary polynucleotides encoding the insecticidal polypeptide comprise an at least 300-basepair contiguous nucleotide sequence from SEQ ID NO:18, and in one embodiment comprises the nucleotide sequence of SEQ ID NO:18.

Also disclosed and claimed is an isolated CryET75 polypeptide comprising at least 15 contiguous amino acids from SEQ ID NO:16. More preferably the polypeptide comprises at least 30 to 45 contiguous amino acids from SEQ ID NO:16. Still more preferably, the polypeptide comprises at least 45 to 90 contiguous amino acids from SEQ ID NO:16, and more preferably comprises at least 90 to 150 contiguous amino acids from SEQ ID NO:16. In an exemplary embodiment, the polypeptide comprises the sequence of SEQ ID NO:16. Such a polypeptide is preferably encoded by a nucleic acid segment that comprises an at least 45-basepair contiguous nucleotide sequence from SEQ ID NO:15, and more preferably is encoded by a nucleic acid segment that comprises an at least 90-basepair contiguous sequence from SEQ ID NO:15. More preferably still, such a polypeptide is encoded by a nucleic acid segment that comprises an at least 150-basepair contiguous sequence from SEQ ID NO:15. Exemplary polynucleotides encoding the insecticidal polypeptide comprise an at least 300-basepair contiguous nucleotide sequence from SEQ ID NO:15, and in one embodiment comprises the nucleotide sequence of SEQ ID NO:15.

In another embodiment, the invention discloses and claims an isolated CryET80 polypeptide comprising at least 17 contiguous amino acids from SEQ ID NO:4. More preferably the polypeptide comprises at least 20 or at least 23 contiguous amino acids from SEQ ID NO:4. Still more preferably, the polypeptide comprises at least 26 or at least 29 contiguous amino acids from SEQ ID NO:4, and more preferably comprises at least 32 or at least 35 contiguous amino acids from SEQ ID NO:4. In an exemplary embodiment, the polypeptide comprises the sequence of SEQ ID NO:4. Such a polypeptide is preferably encoded by a nucleic acid segment that comprises an at least 51-basepair contiguous nucleotide sequence from SEQ ID NO:3, and more preferably is encoded by a nucleic acid segment that comprises an at least 60-basepair contiguous sequence from SEQ ID NO:3. More preferably still, such a polypeptide is encoded by a nucleic acid segment that comprises an at least 78-basepair contiguous sequence from SEQ ID NO:3. Exemplary polynucleotides encoding the insecticidal polypeptide comprise an at least 96-basepair contiguous nucleotide sequence from SEQ ID NO:3, and in one embodiment comprises the nucleotide sequence of SEQ ID NO:3.

In another embodiment, the invention provides an isolated CryET76 polypeptide comprising at least 55 contiguous amino acids from SEQ ID NO:2. More preferably the polypeptide comprises at least 60 or at least 70 contiguous amino acids from SEQ ID NO:2. Still more preferably, the polypeptide comprises at least 75 or at least 80 contiguous amino acids from SEQ ID NO:2, and more preferably comprises at least 85 or at least 90 contiguous amino acids from SEQ ID NO:2. In an exemplary embodiment, the polypeptide comprises the sequence of SEQ ID NO:2. Such a polypeptide is preferably encoded by a nucleic acid segment that comprises an at least 165-basepair contiguous nucleotide sequence from SEQ ID NO:1, and more preferably is encoded by a nucleic acid segment that comprises an at least 180-basepair contiguous sequence from SEQ ID NO:1. More preferably still, such a polypeptide is encoded by a nucleic acid segment that comprises an at least 225-basepair contiguous sequence from SEQ ID NO:1. Exemplary polynucleotides encoding the insecticidal polypeptide comprise an at least 270-basepair contiguous nucleotide sequence from SEQ ID NO:1, and in one embodiment comprises the nucleotide sequence of SEQ ID NO:1.

In a further embodiment, the invention discloses and claims an isolated CryET71 polypeptide comprising at least 146 contiguous amino acids from SEQ ID NO:12. More preferably the polypeptide comprises at least 150 or at least 154 contiguous amino acids from SEQ ID NO:12. Still more preferably, the polypeptide comprises at least 158 or at least 162 contiguous amino acids from SEQ ID NO:12, and more preferably comprises at least 166 or at least 170 contiguous amino acids from SEQ ID NO:12. In an exemplary embodiment, the polypeptide comprises the sequence of SEQ ID NO:12. Such a polypeptide is preferably encoded by a nucleic acid segment that comprises an at least 438-basepair contiguous nucleotide sequence from SEQ ID NO:11, and more preferably is encoded by a nucleic acid segment that comprises an at least 450-basepair contiguous sequence from SEQ ID NO:11. More preferably still, such a polypeptide is encoded by a nucleic acid segment that comprises at least a 462-basepair contiguous sequence from SEQ ID NO:11. Exemplary polynucleotides encoding the insecticidal polypeptide comprise an at least 510-basepair contiguous nucleotide sequence from SEQ ID NO:11, and in one embodiment comprises the nucleotide sequence of SEQ ID NO:11.

The invention also provides an isolated CryET74 polypeptide that comprises the sequence of SEQ ID NO:6. Such a polypeptide is preferably encoded by a nucleic acid segment that comprises at least 45-basepair contiguous nucleotide sequence from SEQ ID NO:5, and more preferably is encoded by a nucleic acid segment that comprises an at least 90-basepair contiguous sequence from SEQ ID NO:5. More preferably still, such a polypeptide is encoded by a nucleic acid segment that comprises an at least 150-basepair contiguous sequence from SEQ ID NO:5. Exemplary polynucleotides encoding the insecticidal polypeptide comprise an at least 300-basepair contiguous nucleotide sequence from SEQ ID NO:5, and in one embodiment comprises the nucleotide sequence of SEQ ID NO:5.

Furthermore, the invention provides an isolated CryET39 polypeptide that comprises the sequence of SEQ ID NO:8. Such a polypeptide is preferably encoded by a nucleic acid segment that comprises an at least 45-basepair contiguous nucleotide sequence from SEQ ID NO:7, and more preferably is encoded by a nucleic acid segment that comprises an at least 90-basepair contiguous sequence from SEQ ID NO:7. More preferably still, such a polypeptide is encoded by a nucleic acid segment that comprises an at least 150-basepair contiguous sequence from SEQ ID NO:7. Exemplary polynucleotides encoding the insecticidal polypeptide comprise an at least 300-basepair contiguous nucleotide sequence from SEQ ID NO:7, and in one embodiment comprises the nucleotide sequence of SEQ ID NO:7.

Likewise, the invention provides an isolated CryET79 polypeptide that comprises the sequence of SEQ ID NO:10. Such a polypeptide is preferably encoded by a nucleic acid segment that comprises an at least 45-basepair contiguous nucleotide sequence from SEQ ID NO:9, and more preferably is encoded by a nucleic acid segment that comprises an at least 90-basepair contiguous sequence from SEQ ID NO:9. More preferably still, such a polypeptide is encoded by a nucleic acid segment that comprises an at least 150-basepair contiguous sequence from SEQ ID NO:9. Exemplary polynucleotides encoding the insecticidal polypeptide comprise at least 300-basepair contiguous nucleotide sequence from SEQ ID NO:9, and in one embodiment comprises the nucleotide sequence of SEQ ID NO:9.

The invention also discloses compositions and insecticidal formulations that comprise one or more of the polypeptides disclosed herein. Such composition may be a cell extract, cell suspension, cell homogenate, cell lysate, cell supernatant, cell filtrate, or cell pellet of a bacteria cell that comprises polynucleotides encoding such polypeptides. Exemplary bacterial cells that produce such polypeptides include *B. thuringiensis* EG4550 (deposited with the NRRL on May 30, 1997 as NRRL B-21784); EG5899 (deposited with the NRRL on May 30, 1997 as NRRL B-21783); EG11529 (deposited with the NRRL on Feb. 12, 1998 as NRRL B-21917); EG4100 (deposited with the NRRL on May 30, 1997 as NRRL B-21786); EG11647 (deposited with the NRRL on May 30, 1997 as NRRL B-21787); EG9444 (deposited with the NRRL on May 30, 1997 as NRRL B-21785); EG11648 (deposited with the NRRL on May 30, 1997 as NRRL B-21788); EG4851 (deposited with the NRRL on Feb. 12, 1998 as NRRL B-21915); and EG11658 (deposited with the NRRL on Feb. 12, 1998 as NRRL B-21916).

The composition as described in detail hereinbelow in this disclosure may be formulated as a powder, dust, pellet, granule, spray, emulsion, colloid, solution, or such like, and may be preparable by such conventional means as desiccation, lyophilization, homogenization, extraction, filtration, centrifugation, sedimentation, or concentration of a culture of cells comprising the polypeptide. Preferably such compositions are obtainable from one or more cultures of the *B. thuringiensis* cells described herein. In all such compositions that contain at least one such insecticidal polypeptide, the polypeptide may be present in a concentration of from about 1% to about 99% by weight.

An exemplary insecticidal polypeptide formulation may be prepared by a process comprising the steps of culturing a suitable *B. thuringiensis* cell under conditions effective to produce the insecticidal polypeptide(s); and obtaining the insecticidal polypeptide(s) so produced.

For example, the invention discloses and claims a method of preparing a δ-endotoxin polypeptide having insecticidal activity against a coleopteran or lepidopteran insect. The method generally involves isolating from a suitable culture of *B. thuringiensis* cells that have been grown under appropriate conditions, one or more of the δ-endotoxin polypeptides produced by the cells. Such polypeptides may be isolated from the cell culture or supernatant or from spore suspensions derived from the cell culture and used in the native form, or may be otherwise purified or concentrated as appropriate for the particular application.

A method of controlling an insect population is also provided by the invention. The method generally involves contacting the population with an insecticidally-effective amount of a polypeptide comprising the amino acid sequence of SEQ ID NOS: 2, 4, 6, 8, 10, 12, 14, 16, or 19. Such methods may be used to kill or reduce the numbers of target insects in a given area, or may be prophylactically applied to an environmental area to prevent infestation by a susceptible insect. Preferably the insect ingests, or is contacted with, an insecticidally-effective amount of the polypeptides.

Additionally, the invention provides a purified antibody that specifically binds to the insecticidal polypeptides disclosed herein. Also provided are methods of preparing such an antibody, and methods for using the antibody to isolate, identify, characterize, and/or purify polypeptides to which such an antibody specifically binds. Immunological kits and immunodetection methods useful in the identification of such polypeptides and peptide fragments and/or epitopes thereof are provided in detail herein, and also represent important aspects of the present invention.

Such antibodies may be used to detect the presence of such polypeptides in a sample, or may be used as described hereinbelow in a variety of immunological methods. An exemplary method for detecting a δ-endotoxin polypeptide in a biological sample generally involves obtaining a biological sample suspected of containing a δ-endotoxin polypeptide; contacting the sample with an antibody that specifically binds to the polypeptide, under conditions effective to allow the formation of complexes; and detecting the complexes so formed.

For such methods, the invention also provides an immunodetection kit. Such a kit generally contains, in suitable container means, an antibody that binds to the δ-endotoxin polypeptide, and at least a first immunodetection reagent. Optionally, the kit may provide additional reagents or instructions for using the antibody in the detection of δ-endotoxin polypeptides in a sample.

Preparation of such antibodies may be achieved using the disclosed polypeptide as an antigen in an animal as described below. Antigenic epitopes, shorter peptides, peptide fusions, carrier-linked peptide fragments, and the like may also be generated from a whole or a portion of the polypeptide sequence disclosed herein.

Another aspect of the invention relates to a biologically-pure culture of a *B. thuringiensis* bacterium as shown in Table 9, deposited with the Agricultural Research Culture Collection, Northern Regional Research Laboratory (NRRL).

A further embodiment of the invention relates to a vector comprising a sequence region that encodes a polypeptide comprising one or more of the amino acid sequences disclosed herein, a recombinant host cell transformed with such a recombinant vector, and biologically-pure cultures of recombinant bacteria transformed with a polynucleotide sequence that encodes the polypeptide disclosed herein. All strains deposited with the NRRL were submitted to the Patent Culture Collection under the terms of the Budapest Treaty, and viability statements pursuant to International Receipt Form BP/4 were obtained. Exemplary vectors, recombinant host cells, transgenic cell lines, pluripotent plant cells, and transgenic plants comprising at least a first sequence region that encodes a polypeptide comprising one or more of the sequences disclosed herein are described in detail hereinbelow.

In a further embodiment, the invention provides methods for preparing an insecticidal polypeptide composition. In exemplary embodiments, such polypeptides may be formulated for use as an insecticidal agent, and may be used to control insect populations in an environment, including agricultural environs and the like. The formulations may be used to kill an insect, either by topical application, or by ingestion of the polypeptide composition by the insect. In certain instances, it may be desirable to formulate the polypeptides of the present invention for application to the soil, on or near plants, trees, shrubs, and the like, near live plants, livestock, domiciles, farm equipment, buildings, and the like.

The present invention also provides transformed host cells, pluripotent plant cell populations, embryonic plant tissue, plant calli, plantlets, and transgenic plants that comprise a selected sequence region that encodes the insecticidal polypeptide. Such cells are preferably prokaryotic or eukaryotic cells such as bacterial, fungal, or plant cells, with exemplary bacterial cells including *B. thuringiensis, B. subtilis, B. megaterium, B. cereus, Escherichia, Salmonella, Agrobacterium* or *Pseudomonas* cells.

The plants and plant host cells are preferably monocotyledonous or dicotyledonous plant cells such as corn, wheat, soybean, oat, cotton, rice, rye, sorghum, sugarcane, tomato, tobacco, kapok, flax, potato, barley, turf grass, pasture grass, berry, fruit, legume, vegetable, ornamental plant, shrub, cactus, succulent, and tree cell.

Illustrative transgenic plants of the present invention preferably have incorporated into their genome a selected polynucleotide (or "transgene"), that comprises at least a first sequence region that encodes one or more of the insecticidal polypeptides disclosed herein.

Likewise, a progeny (decendant, offspring, etc.) of any generation of such a transgenic plant also represents an important aspect of the invention. Preferably such progeny comprise the selected transgene, and inherit the phenotypic trait of insect resistance demonstrated by the parental plant. A seed of any generation of all such transgenic insect-resistant plants is also an important aspect of the invention. Preferably the seed will also comprise the selected transgene and will confer to the plants grown from the seed the phenotypic trait of insect resistance.

Insect resistant, crossed fertile transgenic plants comprising one or more transgenes that encode one or more of the polypeptides disclosed herein may be prepared by a method that generally involves obtaining a fertile transgenic plant that contains a chromosomally incorporated transgene encoding such an insecticidal polypeptide; operably linked to a promoter active in the plant; crossing the fertile transgenic plant with a second plant lacking the transgene to obtain a third plant comprising the transgene; and backcrossing the third plant to obtain a backcrossed fertile plant. In such cases, the transgene may be inherited through a male parent or through a female parent. The second plant may be an inbred, and the third plant may be a hybrid.

Likewise, an insect resistant hybrid, transgenic plant may be prepared by a method that generally involves crossing a first and a second inbred plant, wherein one or both of the first and second inbred plants comprises a chromosomally incorporated transgene that encodes the selected polypeptide operably linked to a plant expressible promoter that expresses the transgene. In illustrative embodiments, the first and second inbred plants may be monocot plants selected from the group consisting of: corn, wheat, rice, barley, oats, rye, sorghum, turfgrass and sugarcane.

In related embodiment, the invention also provides a method of preparing an insect resistant plant. The method generally involves contacting a recipient plant cell with a DNA composition comprising at least a first transgene that encodes an insecticidal polypeptide under conditions permitting the uptake of the DNA composition; selecting a recipient cell comprising a chromosomally incorporated transgene that encodes the polypeptide; regenerating a plant from the selected cell; and identifying a fertile transgenic plant that has enhanced insect resistance relative to the corresponding non-transformed plant.

A method of producing transgenic seed generally involves obtaining a fertile transgenic plant comprising a chromosomally integrated transgene that encodes a polypeptide comprising one or more of the amino acid sequences disclosed herein, operably linked to a promoter that expresses the transgene in a plant; and growing the plant under appropriate conditions to produce the transgenic seed.

A method of producing progeny of any generation of an insect resistance-enhanced fertile transgenic plant is also provided by the invention. The method generally involves collecting transgenic seed from a transgenic plant comprising a chromosomally integrated transgene that encodes such a polypeptide, operably linked to a promoter that expresses the transgene in the plant; planting the collected transgenic seed; and growing the progeny transgenic plants from the seed.

These methods for creating transgenic plants, progeny and seed may involve contacting the plant cell with the DNA composition using one of the processes well-known for plant cell transformation such as microprojectile bombardment, electroporation or *Agrobacterium*-mediated transformation. These and other embodiments of the present invention will be apparent to those of skill in the art from the following examples and claims, having benefit of the teachings of the Specfication herein.

2.1 Polynucleotide Segments

The present invention provides nucleic acid segments, that can be isolated from virtually any source, that are free from total genomic DNA and that encode the novel insecticidal polypeptides and peptide fragments thereof that are disclosed herein. The polynucleotides encoding these peptides and polypeptides may encode active insecticidal proteins, or peptide fragments, polypeptide subunits, functional domains, or the like of one or more of the CryET84, CryET80, CryET76, CryET71, CryET69, CryET75, CryET39, CryET79, CryET74 and related crystal proteins as the polypeptides disclosed herein. In addition the invention encompasses nucleic acid segments which may be synthesized entirely in vitro using methods that are well-known to those of skill in the art which encode the novel polypeptides, peptides, peptide fragments, subunits, or functional domains disclosed herein.

As used herein, the term "nucleic acid segment" or "polynucleotide" refers to a nucleic acid molecule that has been isolated free of the total genomic DNAs of a particular species. Therefore, a nucleic acid segment or polynucleotide encoding an endotoxin polypeptide refers to a nucleic acid molecule that comprises at least a first crystal protein-encoding sequences yet is isolated away from, or purified free from, total genomic DNA of the species from which the nucleic acid segment is obtained, which in the instant case is the genome of the Gram-positive bacterial genus, *Bacillus*, and in particular, the species of *Bacillus* known as *B. thuringiensis*. Included within the term "nucleic acid segment", are polynucleotide segments and smaller fragments of such segments, and also recombinant vectors, including, for example, plasmids, cosmids, phagemids, phage, virions, baculoviruses, artificial chromosomes, viruses, and the like. Accordingly, polynucleotide sequences that have between about 70% and about 80%, or more preferably between about 81% and about 90%, or even more preferably between about 91% and about 99% nucleic acid sequence identity or functional equivalence to the polynucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:18 will be sequences that are "essentially as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:18." Highly preferred sequences, are those which are preferably about 91%, about 92%, about 93%, about 94%, about 95%, about 96%, about 97%, about 98%, about 99%, or about 100% identical or finctionally equivalent to the nucleotide sequence of SEQ ID NO: 1, SEQ ID NO:3, SEQ ID NO:13, SEQ ID NO:15, or SEQ ID NO:18. Other preferred sequences that encode related polypeptide sequences are those which are about 81%, 82%, 83%, 84%, 85%, 86%, 87%, 88%, 89%, or 90% identical or finctionally equivalent to the polynucleotide sequence set forth in one or more of these sequence identifiers. Likewise, sequences that are about 71%, 72%, 73%, 74%, 75%, 76%, 77%, 78%, 79%, or 80% identical or functionally equivalent to the polynucleotide sequence set forth in one or more of these sequence identifiers are also contemplated to be useful in the practice of the present invention.

Similarly, a polynucleotide comprising an isolated, purified, or selected gene or sequence region refers to a polynucleotide which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, or polypeptide-encoding unit. As will be understood by those in the art, this functional term includes both genomic sequences, operator sequences and smaller engineered gene segments that express, or may be adapted to express, proteins, polypeptides or peptides. In certain embodiments, a nucleic acid segment will comprise at least a first gene that encodes one or more of the polypeptides disclosed herein.

To permit expression of the gene, and translation of the mRNA into mature polypeptide, the nucleic acid segment preferably also comprises at least a first promoter operably linked to the gene to express the gene product in a host cell transformed with this nucleic acid segment. The promoter may be an endogenous promoter, or alternatively, a heterologous promoter selected for its ability to promote expression of the gene in one or more particular cell types. For example, in the creation of transgenic plants and pluripotent plant cells comprising a selected gene, the heterologous promoter of choice is one that is plant-expressible, and in many instances, may preferably be a plant-expressible promoter that is tissue- or cell cycle-specific. The selection of plant-expressible promoters is well-known to those skilled in the art of plant transformation, and exemplary suitable promoters are described herein. In certain embodiments, the plant-expressible promoter may be selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated polynucleotides (such as DNAs, RNAs, antisense DNAs, antisense RNAs, ribozymes, and PNAs) and recombinant vectors comprising polynucleotide sequences that encode one or more of the polypeptides disclosed herein.

The term "a sequence essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19" means that the sequence substantially corresponds to a portion of the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19 will be sequences that are "essentially as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19." Highly preferred sequences, are those which are preferably about 91%, about 92%, about 93%, about 94%, about 95%, about 96%, about 97%, about 98%, about 99%, or about 100% identical or functionally equivalent to the amino acid sequence of SEQ ID NO:2, SEQ ID NO:4, SEQ ID NO:14, SEQ ID NO:16, or SEQ ID NO:19. Other preferred sequences are those which are about 81%, 82%, 83%, 84%, 85%, 86%, 87%, 88%, 89%, or 90% identical or functionally equivalent to the amino acid sequence of SEQ ID NO:2, SEQ ID NO:4, SEQ ID NO:14, SEQ ID NO:16, or SEQ ID NO:19. Likewise, sequences that are about 71%, 72%, 73%, 74%, 75%, 76%, 77%, 78%, 79%, or 80% identical or finctionally equivalent to the polypeptide sequence set forth in SEQ ID NO:2, SEQ ID NO:4, SEQ ID NO:14, SEQ ID NO:16, or SEQ ID NO:19 are also contemplated to be useful in the practice of the present invention.

It will also be understood that amino acid and nucleic acid sequences may include additional residues, such as additional N— or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, ie., introns, which are known to occur within genes.

The nucleic acid segments of the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. For example, nucleic acid fragments may be prepared that include a short contiguous stretch encoding the peptide sequence disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19, or that are identical to or complementary to nucleic acid sequences which encode the peptides disclosed in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or SEQ ID NO:19, and particularly those nucleic acid segments disclosed in SEQ ID NOS:1, 3, 13, 15, or 18. For example, nucleic acid sequences such as about 23 nucleotides, and that are up to about 10,000, about 5,000, about 3,000, about 2,000, about 1,000, about 500, about 200, about 100, about 50, and about 23 or so base pairs in length (including all intermediate lengths) that comprise a contiguous nucleotide sequence from SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:18 or those that encode a contiguous amino acid sequence from SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19 are contemplated to be particularly useful.

It will be readily understood that "intermediate lengths", in the context of polynucleotide sequences, or nucleic acid segments, or primer or probes specific for the disclosed gene, means any length between the quoted ranges, such as from about 24, 25, 26, 27, 28, 29, etc.; 30, 31, 32, 33, 34, 35, 36, 37, 38, 39, etc.; 40, 41, 42, 43, 44, 45, 46, 47, 48, 49, 50, 51, 52, 53, 54, 55, 56, 57, 58, 59, 60, 65, 70, 75, 80, 85, 90, 95, etc.; 100, 101, 102, 103, 104, etc.; 110, 120, 125, 130, 135, 140, 145, 150, 155, 160, 165, 170, 180, 190, etc.; including all integers in the ranges of from about 200-500; 500-1,000; 1,000-2,000; 2,000-3,000; 3,000-5,000; and up to and including sequences of about 10,000 or 12,000 or so nucleotides and the like.

Likewise, it will be readily understood that "intermediate lengths", in the context of polypeptides or peptides, means any length between the quoted ranges of contiguous amino acids. For example, when considering the disclosed insecticidal polypeptides, all lengths between about 7 and about 300 contiguous amino acid sequences are contemplated to be useful in particular embodiments disclosed herein. For example, peptides comprising contiguous amino acid sequences having about 7, about 8, about 9, about 10, about 11, about 12, about 13, about 14, about 15, about 16, about 17, about 18, about 19, about 20, about 21, about 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, etc., 70, 75, etc., 80, 85, etc., 90, 95, etc., and even those peptides comprising at least about 96, 97, 98, 99, 100, 101, 102, 103, and 104, or more contiguous amino acids from SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19 are explicitly considered to fall within the scope of the present invention.

Furthermore, it will also be readily understood by one of skill in the art, that "intermediate lengths", in the context of larger insecticidally-active polypeptides, means any length between the quoted ranges of contiguous amino acids that comprise such a polypeptide. For example, when considering the polypeptides of the present invention, all lengths between about 100 and about 1000 contiguous amino acid sequences are contemplated to be useful in particular embodiments disclosed herein. For example, polypeptides comprising a contiguous amino acid sequence having at least about 100, about 101, about 102, 103, 104, 105, 106, 107, 108, 109, 110, 115, 120, 125, 130, 135, 140, 145, 150, 155, 160, 165, 170, 175, 180, 185, 190, 195, etc., 200, 201, 202, 203, 204, 205, 206, 207, 208, 209, 210, 220, 230, 240, 250, 260, 270, 280, 290, etc., 300, 310, 320, 330, 340, 350, 360, 370, 380, 390, 400, etc., 410, 430, 450, 470, 490, etc., 500, 525, 550, 575, 600, 650, 675, 700, etc., 750, etc., and even those polypeptides that comprise at least about 775 or more amino acids are explicitly considered to fall within the scope of the present invention. Particularly in the case of fusion proteins comprising a whole or a portion of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19 longer polypeptide sequences may be preferred, including sequences that comprise about 760, 770, 780, 790, or even about 800 or 900 or greater amino acids in length.

It will also be understood that this invention is not limited to the particular nucleic acid sequences which encode peptides of the present invention, or which encode the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19 including the DNA sequence which is particularly disclosed in SEQ ID NO:1, SEQ ID NO:3, SEQ ID NO:5, SEQ ID NO:7, SEQ ID NO:9, SEQ ID NO:11, SEQ ID NO:13, SEQ ID NO:15 or SEQ ID NO:18. Recombinant vectors and isolated DNA segments may therefore variously include the polypeptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level. Alternatively, native, as yet-unknown or as yet unidentified polynucleotides and/or polypeptides structurally and/or functionally-related to the sequences disclosed herein may also be identified that fall within the scope of the present invention. Such polynucleotides are those polynucleotides that encode a polypeptide structurally and/or functionally similar or identical to, the polypeptide characterized herein as a crystal protein-encoding polynucleotide. Since the designations "CryET39," "CryET69," "CryET71," "CryET74," "CryET76," "CryET79," "CryET80," "CryET84" and "CryET75" are arbitrary names chosen to readily identify polypeptides comprising the amino acid sequences disclosed herein, it is likely that many other polypeptides may be identified that are highly homologous to (or even identical to) this sequence, but which may have been isolated from different organisms or sources, or alternatively, may even have been synthesized entirely, or partially de novo. As such, all polypeptide sequences, whether naturally-occurring, or artificially-created, that are structurally homologous to the primary amino acid sequences as described herein and that have similar insecticidal activity against the target insects disclosed herein are considered to fall within the scope of this disclosure. Likewise, all polynucleotide sequences, whether naturally-occurring, or artificially-created, that are structurally homologous to the nucleotide sequences disclosed herein, or that encodes a polypeptide that is homologous, and biologically-functionally equivalent to the amino acid sequence disclosed herein are also considered to fall within the scope of this disclosure.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length insecticidal protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein. In many cases, the promoter may be a native promoter, or alternatively, a heterologous promoter, such as those of bacterial origin (including promoters from other crystal proteins), fungal origin, viral, phage or phagemid origin (including promoters such as CaMV35, and its derivatives, T3, T7, λ, and ϕ promoters and the like), or plant origin (including constitutive, inducible, and/or tissue-specific promoters and the like).

2.1.1 Characteristics of the CryET76, CryET80 and CryET84 Polypeptides Isolated from EG4851

The present invention provides a novel polypeptide that defines a whole or a portion of a *B. thuringiensis* CryET76, CryET84 or a CryET80 crystal proteins.

In a preferred embodiment, the invention discloses and claims an isolated and purified CryET76 protein. The CryET76 protein isolated from EG4851 comprises a 387-amino acid sequence, and has a calculated molecular mass of approximately 43,800 Da. CryET76 has a calculated isoelectric constant (pI) equal to 5.39.

In a preferred embodiment, the invention discloses and claims an isolated and purified CryET80 protein. The CryET80 protein isolated from EG4851 comprises a 132-amino acid sequence, and has a calculated molecular mass of approximately 14,800 Da. CryET80 has a calculated isoelectric constant (pI) equal to 6.03.

In a preferred embodiment, the invention discloses and claims an isolated and purified CryET84 protein. The CryET84 protein isolated from EG4851 comprises a 341-amino acid sequence, and has a calculated molecular mass of approximately 37,884 Da. CryET84 has a calculated isoelectric constant (pI) equal to 5.5.

In strain EG4851, the cryET80 and cryET76 genes are preferably located on a single DNA segment and are separated by about 95 nucleotides. The gene for CryET76 extends from nucleotide nucleotide 514 to nucleotide 1674 of SEQ ID NO:5, and the gene encoding CryET80 extends from nucleotide 23 to nucleotide 418 of SEQ ID NO:5. In the present invention, the cryET80 and cryET76 genes may be preferably located on a single DNA segment.

In strain EG4851, the cryET84 gene is located immediately 5' to the cryET80 and cryET76 genes. The nucleotide sequence of the cryET84 gene is shown in SEQ ID NO:18 and the deduced amino acid sequence of the CryET84 protein is shown in SEQ ID NO:19. In the present invention, the cryET80, cryET84, and cryET76 genes may be preferably located on a single DNA segment (e.g. SEQ ID NO:17).

2.2 Nucleic Acid Segments as Hybridization Probes and Primers

In addition to their use in directing the expression of crystal proteins or peptides of the present invention, the nucleic acid sequences described herein also have a variety of other uses. For example, they have utility as probes or primers in nucleic acid hybridization embodiments. The invention provides a method for detecting a nucleic acid sequence encoding a δ-endotoxin polypeptide. The method generally involves obtaining sample nucleic acids suspected of encoding a δ-endotoxin polypeptide; contacting the sample nucleic acids with an isolated nucleic acid segment comprising one of the sequences disclosed herein, under conditions effective to allow hybridization of substantially complementary nucleic acids; and detecting the hybridized complementary nucleic acids thus formed.

Also provided is a nucleic acid detection kit comprising, in suitable container means, at least a first nucleic acid segment comprising at least 23 contiguous nucleotides from SEQ ID NO:1, SEQ ID NO:3, SEQ ID NO:5, SEQ ID NO:7, SEQ ID NO:9, SEQ ID NO:11, SEQ ID NO:13, SEQ ID NO:15 or SEQ ID NO:18, and at least a first detection reagent. The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 23 to about 50, or even up to and including sequences of about 100-200 nucleotides or so, identical or complementary to the DNA sequences herein, are particularly contemplated as hybridization probes for use in, e.g., Southern and Northern blotting. Intermediate-sized fragments will also generally find use in hybridization embodiments, wherein the length of the contiguous complementary region may be varied, such as between about 25-30, or between about 30 and about 40 or so nucleotides, but larger contiguous complementary stretches may be used, such as those from about 200 to about 300, or from about 300 to about 400 or 500 or so nucleotides in length, according to the length complementary sequences one wishes to detect. It is even possible that longer contiguous sequence regions may be utilized including those sequences comprising at least about 600, 700, 800, 900, 1000, 1100, 1200, 1300, 1400, 1500, or more contiguous nucleotides from one of the sequences disclosed herein.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids. "High stringency" hybridization conditions, e.g., typically employ relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1990; Maloy 1994; Segal, 1976; Prokop and Bajpai, 1991; and Kuby, 1994, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ “low stringency” or “reduced stringency” hybridization conditions such as those employing from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results. Regardless of what particular combination of salts (such as NaCl or NaCitrate and the like), organic buffers (including e.g., formamide and the like), and incubation or washing temperatures are employed, the skilled artisan will readily be able to employ hybridization conditions that are “high,” “medium,” or “low” stringency, and will be able to interpret the results from hybridization analyses using such conditions to determine the relative homology of a target nucleic acid sequence to that of the particular novel polynucleotide probe sequence employed from SEQ ID NO:1, SEQ ID NO:3, SEQ ID NO:5, SEQ ID NO:7, SEQ ID NO:9, SEQ ID NO:11, SEQ ID NO:13, SEQ ID NO:15 or SEQ ID NO:18.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 Vectors and Methods for Recombinant Expression of Cry Related Polypeptides In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., (1989). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise a contiguous amino acid sequence as disclosed herein.

2.4 Transgenic Plants Expressing CryET Polypeptides

In yet another aspect, the present invention provides methods for producing a transgenic plant that expresses a selected nucleic acid segment comprising a sequence region that encodes the novel endotoxin polypeptides of the present invention. The process of producing transgenic plants is well-known in the art. In general, the method comprises transforming a suitable plant host cell with a DNA segment that contains a promoter operatively linked to a coding region that encodes one or more of the disclosed polypeptides. Such a coding region is generally operatively linked to at least a first transcription-terminating region, whereby the promoter is capable of driving the transcription of the coding region in the cell, and hence providing the cell the ability to produce the polypeptide in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises transgenic plants which express a gene, gene segment, or sequence region that encodes at least one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more transgenes, either native, synthetically modified, or mutated, that encodes an insecticidal polypeptide that is identical to, or highly homologous to the polypeptide disclosed herein. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant. Alternatively, a second transgene may be introduced into the plant cell to confer additional phenotypic traits to the plant. Such transgenes may confer resistance to one or more insects, bacteria, fungi, viruses, nematodes, or other pathogens.

A preferred gene which may be introduced includes, for example, a crystal protein-encoding DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of pluripotent plant cells, and regeneration of a transgenic cell line from a transformed cell, cell culture, embryo, or callus tissue are well-known in the art, and are discussed herein. Vectors, (including plasmids, cosmids, phage, phagemids, baculovirus, viruses, virions, BACs [bacterial artificial chromosomes], YACs [yeast artificial chromosomes]) comprising at least a first nucleic acid segment encoding an insecticidal polypeptide for use in transforming such cells will, of course, generally comprise either the operons, genes, or gene-derived sequences of the present invention, either native, or synthetically-derived, and particularly those encoding the disclosed crystal proteins. These nucleic acid constructs can further include structures such as promoters, enhancers, polylinkers, introns, terminators, or even gene sequences which have positively- or negatively-regulating activity upon the cloned δ-endotoxin gene as desired. The DNA segment or gene may encode either a native or modified crystal protein, which will be expressed in the resultant recombinant cells, and/or which will confer to a transgenic plant comprising such a segment, an improved phenotype (in this case, increased resistance to insect attack, infestation, or colonization).

The preparation of a transgenic plant that comprises at least one polynucleotide sequence encoding an insecticidal polypeptide for the purpose of increasing or enhancing the resistance of such a plant to attack by a target insect represents an important aspect of the invention. In particular, the inventors describe herein the preparation of insect-resistant monocotyledonous or dicotyledonous plants, by incorporating into such a plant, a transgenic DNA segment encoding one or more insecticidal polypeptides which are toxic to a coleopteran or lepidopteran insect.

In a related aspect, the present invention also encompasses a seed produced by the transformed plant, a progeny from such seed, and a seed produced by the progeny of the original transgenic plant, produced in accordance with the above process. Such progeny and seeds will have a crystal protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more crystal proteins or polypeptides are aspects of this invention. As well-known to those of skill in the art, a progeny of a plant is understood to mean any offspring or any descendant from such a plant.

2.5 Crystal Protein Screening and Detection Kits

The present invention contemplates methods and kits for screening samples suspected of containing crystal protein polypeptides or crystal protein-related polypeptides, or cells producing such polypeptides. A kit may contain one or more antibodies specific for the disclosed amino acid sequences disclosed, or one or more antibodies specific for a peptide derived from one of the sequences disclosed, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

The reagent(s) of the kit can be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a crystal protein or peptide or a crystal protein-related peptide or antibody sought to be detected, as the case may be, may be employed. It is contemplated that such embodiments may have application in the tittering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides. Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.6 Insecticidal Compositions and Methods of Use

The inventors contemplate that the polypeptide compositions disclosed herein will find particular utility as insecticides for topical and/or systemic application to field crops, grasses, fruits and vegetables, lawns, trees, and/or ornamental plants. Alternatively, the polypeptides disclosed herein may be formulated as a spray, dust, powder, or other aqueous, atomized or aerosol for killing an insect, or controlling an insect population. The polypeptide compositions disclosed herein may be used prophylactically, or alternatively, may be administered to an environment once target insects, such as WCRW, have been identified in the particular environment to be treated. The polypeptide compositions may comprise an individual Cry polypeptide or may contain various combinations of the polypeptides disclosed herein.

Regardless of the method of application, the amount of the active polypeptide component(s) is applied at an insecticidally-effective amount, which will vary depending on such factors as, for example, the specific target insects to be controlled, the specific environment, location, plant, crop, or agricultural site to be treated, the environmental conditions, and the method, rate, concentration, stability, and quantity of application of the insecticidally-active polypeptide composition. The formulations may also vary with respect to climatic conditions, environmental considerations, and/or frequency of application and/or severity of insect infestation.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

2.6.1 Oil Flowable Suspensions

In a preferred embodiment, the bioinsecticide composition comprises an oil flowable suspension of bacterial cells which expresses the novel crystal protein disclosed herein. Exemplary bacterial species include those such as *B. thuringiensis, B. megaterium, B. subtilis, B. cereus, E. coli, Salmonella* spp., *Agrobacterium* spp., or *Pseudomonas* spp.

2.6.2 Water-Dispersible Granules

In another important embodiment, the bioinsecticide composition comprises a water dispersible granule. This granule comprises bacterial cells which expresses a novel crystal protein disclosed herein. Preferred bacterial cells include bacteria such as *B. megaterium, B. subtilis, B. cereus, E. coli, Salmonella* spp., *Agrobacterium* spp., or *Pseudomonas* spp. cells transformed with a DNA segment disclosed herein and expressing the crystal protein are also contemplated to be useful.

2.6.3 Powders, Dusts, and Spore Formulations

In a third important embodiment, the bioinsecticide composition comprises a wettable powder, dust, spore crystal formulation, cell pellet, or colloidal concentrate. This powder comprises bacterial cells which expresses a novel crystal protein disclosed herein. Preferred bacterial cells include *B. thuringiensis* cells, or cells of strains of bacteria such as *B. megaterium, B. subtilis, B. cereus, E. coli, Salmonella* spp., *Agrobacterium* spp., or *Pseudomonas* spp. and the like, may also be transformed with one or more nucleic acid segments as disclosed herein. Such dry forms of the insecticidal compositions may be formulated to dissolve immediately upon wetting, or alternatively, dissolve in a controlled-release, sustained-release, or other time-dependent manner. Such compositions may be applied to, or ingested by, the target insect, and as such, may be used to control the numbers of insects, or the spread of such insects in a given environment.

2.6.4 Aqueous Suspensions and Bacterial Cell Filtrates or Lysates

In a fourth important embodiment, the bioinsecticide composition comprises an aqueous suspension of bacterial cells or an aqueous suspension of parasporal crystals, or an aqueous suspension of bacterial cell lysates or filtrates, etc., such as those described above which express the crystal protein. Such aqueous suspensions may be provided as a concentrated stock solution which is diluted prior to application, or alternatively, as a diluted solution ready-to-apply.

For these methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel insecticidal polypeptides may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or colloidal preparations of such crystals and/or spores as the active bioinsecticidal composition.

2.6.5 Multifunctional Formulations

In certain embodiments, when the control of multiple insect species is desired, the insecticidal formulations described herein may also further comprise one or more chemical pesticides, (such as chemical pesticides, nematocides, fungicides, virucides, microbicides, amoebicides, insecticides, etc.), and/or one or more δ-endotoxin polypeptides having the same, or different insecticidal activities or insecticidal specificities, as the insecticidal polypeptide identified herein. The insecticidal polypeptides may also be used in conjunction with other treatments such as fertilizers, weed killers, cryoprotectants, surfactants, detergents, insecticidal soaps, dormant oils, polymers, and/or time-release or biodegradable carrier formulations that permit long-term dosing of a target area following a single application of the formulation. Likewise the formulations may be prepared into edible "baits" or fashioned into insect "traps" to permit feeding or ingestion by a target insect of the insecticidal formulation.

The insecticidal compositions of the invention may also be used in consecutive or simultaneous application to an environmental site singly or in combination with one or more additional insecticides, pesticides, chemicals, fertilizers, or other compounds.

2.6.6 Application Methods and Effective Rates

The insecticidal compositions of the invention are applied to the environment of the target insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, including dusting, sprinkling, soil soaking, soil injection, seed coating, seedling coating, foliar spraying, aerating, misting, atomizing, fumigating, aerosolizing, and the like, are also feasible and may be required under certain circumstances such as e.g., insects that cause root or stalk infestation, or for application to delicate vegetation or ornamental plants. These application procedures are also well-known to those of skill in the art.

The insecticidal compositions of the present invention may also be formulated for preventative or prophylactic application to an area, and may in certain circumstances be applied to pets, livestock, animal bedding, or in and around farm equipment, barns, domiciles, or agricultural or industrial facilities, and the like.

The concentration of insecticidal composition which is used for environmental, systemic, topical, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the polypeptide compositions may be from about 1% to about 99% or more by weight of the protein composition, while liquid formulations may generally comprise from about 1% to about 99% or more of the active ingredient by weight. As such, a variety of formulations are preparable, including those formulations that comprise from about 5% to about 95% or more by weight of the insecticidal polypeptide, including those formulations that comprise from about 10% to about 90% or more by weight of the insecticidal polypeptide. Naturally, compositions comprising from about 15% to about 85% or more by weight of the insecticidal polypeptide, and formulations comprising from about 20% to about 80% or more by weight of the insecticidal polypeptide are also considered to fall within the scope of the present disclosure.

In the case of compositions in which intact bacterial cells that contain the insecticidal polypeptide are included, preparations will generally contain from about $10^4$ to about $10^8$ cells/mg, although in certain embodiments it may be desirable to utilize formulations comprising from about $10^2$ to about $10^4$ cells/mg, or when more concentrated formulations are desired, compositions comprising from about $10^8$ to about $10^{10}$ or $10^{11}$ cells/mg may also be formulated. Alternatively, cell pastes, spore concentrates, or crystal protein suspension concentrates may be prepared that contain the equivalent of from about $10^{12}$ to $10^{13}$ cells/mg of the active polypeptide, and such concentrates may be diluted prior to application.

The insecticidal formulation described above may be administered to a particular plant or target area in one or more applications as needed, with a typical field application rate per hectare ranging on the order of from about 50 g/hectare to about 500 g/hectare of active ingredient, or alternatively, from about 500 g/hectare to about 1000 g/hectare may be utilized. In certain instances, it may even be desirable to apply the insecticidal formulation to a target area at an application rate of from about 1000 g/hectare to about 5000 g/hectare or more of active ingredient. In fact, all application rates in the range of from about 50 g of active polypeptide per hectare to about 10,000 g/hectare are contemplated to be useful in the management, control, and killing, of target insect pests using such insecticidal formulations. As such, rates of about 100 g/hectare, about 200 g/hectare, about 300 g/hectare, about 400 g/hectare, about 500 g/hectare, about 600 g/hectare, about 700 g/hectare, about 800 g/hectare, about 900 g/hectare, about 1 kg/hectare, about 1.1 kg/hectare, about 1.2 kg/hectare, about 1.3 kg/hectare, about 1.4 kg/hectare, about 1.5 kg/hectare, about 1.6 kg/hectare, about 1.7 kg/hectare, about 1.8 kg/hectare, about 1.9 kg/hectare, about 2.0 kg/hectare, about 2.5 kg/hectare, about 3.0 kg/hectare, about 3.5 kg/hectare, about 4.0 kg/hectare, about 4.5 kg/hectare, about 6.0 kg/hectare, about 7.0 kg/hectare, about 8.0 kg/hectare, about 8.5 kg/hectare, about 9.0 kg/hectare, and even up to and including about 10.0 kg/hectare or greater of active polypeptide may be utilized in certain agricultural, industrial, and domestic applications of the pesticidal formulations described hereinabove.

2.7 Epitopic Core Sequences

The present invention is also directed to protein or peptide compositions, free from total cells and other peptides, which comprise a purified peptide which incorporates an epitope that is immunologically cross-reactive with one or more antibodies that are specific for the disclosed polypeptide sequences. In particular, the invention concerns epitopic core sequences derived from one or more of the polypeptides disclosed herein.

As used herein, the term "incorporating an epitope(s) that is immunologically cross-reactive with one or more antibodies that are specific for the disclosed polypeptide sequence" is intended to refer to a peptide or protein antigen which includes a primary, secondary or tertiary structure similar to an epitope located within the disclosed polypeptide. The level of similarity will generally be to such a degree that monoclonal or polyclonal antibodies directed against the crystal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic crystal protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to crystal proteins and related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the crystal protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.8 Definitions

The following words and phrases have the meanings set forth below.

Expression: The combination of intracellular processes, including transcription and translation undergone by a coding DNA molecule such as a structural gene to produce a polypeptide.

Pluripotent: A term used to describe develomental plasiticity. A pluripotent cell is capable of differentiating into a number of different cell types and lineages. For example, a stem cell in the bone marrow may give rise to many different lineages of circulating blood cells. This is in contrast to a differentiated cell, which is generally committed to a particular developmental pathway.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived from or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or a progeny of any generation of the plant that was derived from a transformed plant cell or protoplast, wherein the plant nucleic acids contains an exogenous selected nucleic acid sequence region not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast or from transformed pluripotent plant cells as being a transgenic plant. Preferably, transgenic plants of the present invention include those plants that comprise at least a first selected polynucleotide that encodes an insecticidal polypeptide. This selected polynucleotide is preferably a δ-endotoxin coding region (or gene) operably linked to at least a first promoter that expresses the coding region to produce the insecticidal polypeptide in the transgenic plant. Preferably, the transgenic plants of the present invention that produce the encoded polypeptide demonstrate a phenotype of improved resistance to target insect pests. Such transgenic plants, their progeny, descendants, and seed from any such generation are preferably insect resistant plants.

Vector: A nucleic acid molecule capable of replication in a host cell and/or to which another nucleic acid segment can be operatively linked so as to bring about replication of the attached segment. Plasmids, phage, phagemids, and cosmids are all exemplary vectors. In many embodiments, vectors are used as a vehicle to introduce one or more selected polynucleotides into a host cell, thereby generating a "transformed" or "recombinant" host cell.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1 Restriction map of pEG1337

Figure 2:
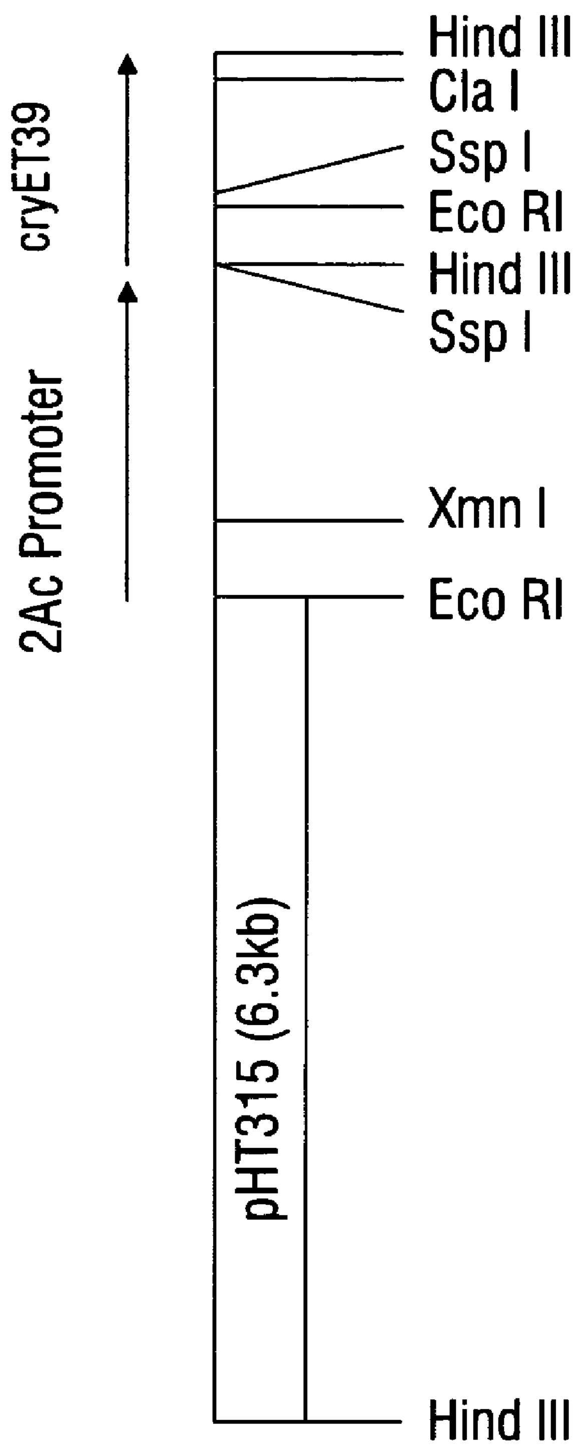

FIG. 2 Restriction map of pEG1921.

Figure 3:
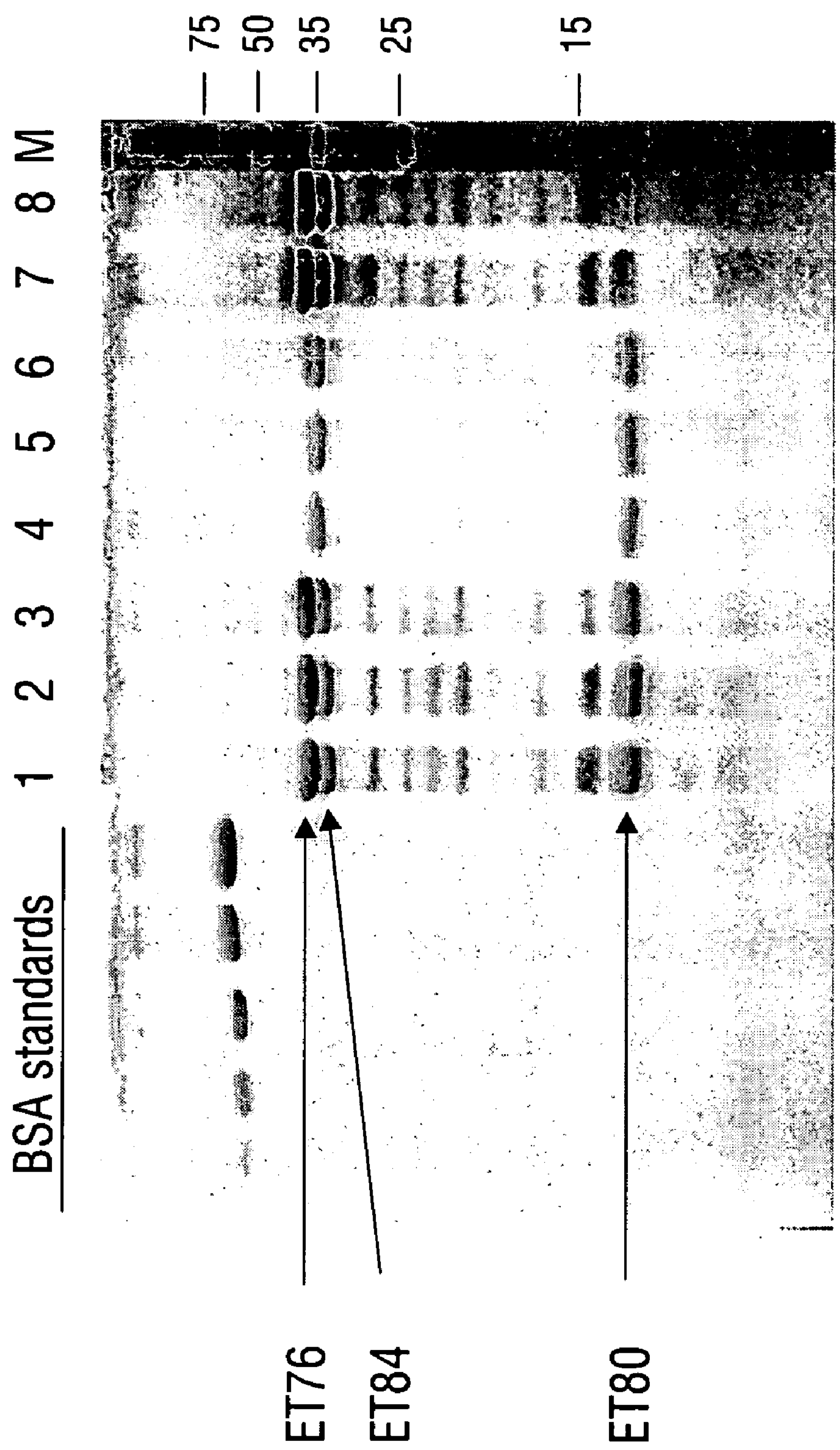

FIG. 3 SDS-PAGE analysis of spore-crystal suspensions from C2 cultures of EG11658, EG12156, and EG12158. Twenty-five microliters (μl) of the suspensions were diluted with 75 μl of sterile water and prepared for electrophoresis as described in Example 11. Ten microliters were loaded per lane on the 15% acrylamide gel. A serial dilution of bovine serum albumin (BSA) was included as a standard. Lanes 1-3, EG11658; lanes 4-6, EG12156; lanes 7-8, EG12158. M=molecular weight standards (Sigma M-0671) in kilodaltons. The bands corresponding to CryET76, CryET80, and CryET84 are indicated by the arrows.

4.0 DESCRIPTION OF ILLUSTRATIVE EMBODIMENTS

4.1 Some Advantages of the Invention

The present invention provides novel δ-endotoxins which are highly toxic to insects such as WCRW, SCRW, and CPB. These protein have amino acid sequences which are only distantly related to those of other δ-endotoxins that are toxic to dipteran or coleopteran insects. Based on the guidelines established for the *B. thuringiensis* crystal protein nomenclature (Crickmore et al., 1998), two of these polypeptides, designated CryET76 and CryET80, represent a new subclass of coleopteran active insecticidal crystal proteins.

4.2 Insect Pests

Almost all field crops, plants, and commercial farming areas are susceptible to attack by one or more insect pests. Particularly problematic are the lepidopteran and coleopteran pests identified in Table 1. For example, vegetable and cole crops such as artichokes, kohlrabi, arugula, leeks, asparagus, lentils, beans, lettuce (e.g., head, leaf, romaine), beets, bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, peas, Chinese cabbage, peppers, collards, potatoes, cucumber, pumpkins, cucurbits, radishes, dry bulb onions, rutabaga, eggplant, salsify, escarole, shallots, endive, soybean, garlic, spinach, green onions, squash, greens, sugar beets, sweet potatoes, turnip, swiss chard, horseradish, tomatoes, kale, turnips, and a variety of spices are sensitive to infestation by one or more of the following insect pests: alfalfa looper, armyworm, beet armyworm, artichoke plume moth, cabbage budworm, cabbage looper, cabbage webworm, corn earworm, celery leafeater, cross-striped cabbageworm, european corn borer, diamondback moth, green cloverworm, imported cabbageworm, melonworm, omnivorous leafroller, pickleworm, rindworm complex, saltmarsh caterpillar, soybean looper, tobacco budworm, tomato fruitworm, tomato hornworm, tomato pinworm, velvetbean caterpillar, and yellowstriped armyworm.

Likewise, pasture and hay crops such as alfalfa, pasture grasses and silage are often attacked by such pests as armyworm, beef armyworm, alfalfa caterpillar, European skipper, a variety of loopers and webworms, as well as yellowstriped armyworms.

Fruit and vine crops such as apples, apricots, cherries, nectarines, peaches, pears, plums, prunes, quince almonds, chestnuts, filberts, pecans, pistachios, walnuts, citrus, blackberries, blueberries, boysenberries, cranberries, currants, loganberries, raspberries, strawberries, grapes, avocados, bananas, kiwi, persimmons, pomegranate, pineapple, tropical fruits are often susceptible to attack and defoliation by achema sphinx moth, amorbia, armyworm, citrus cutworm, banana skipper, blackheaded fireworm, blueberry leafroller, cankerworm, cherry fruitworm, citrus cutworm, cranberry girdler, eastern tent caterpillar, fall webworm, fall webworm, filbert leafroller, filbert webworm, fruit tree leafroller, grape berry moth, grape leaffolder, grapeleaf skeletonizer, green fruitworm, gummosos-batrachedra commosae, gypsy moth, hickory shuckworm, hornworms, loopers, navel orangeworm, obliquebanded leafroller, omnivorous leafroller. omnivorous looper, orange tortrix, orangedog, oriental fruit moth, pandemis leafroller, peach twig borer, pecan nut casebearer, redbanded leafroller, redhumped caterpillar, roughskinned cutworm, saltmarsh caterpillar, spanworm, tent caterpillar, thecla-thecla basillides, tobacco budworm, tortrix moth, tufted apple budmoth, variegated leafroller, walnut caterpillar, western tent caterpillar, and yellowstriped armyworm.

Field crops such as canola/rape seed, evening primrose, meadow foam, corn (field, sweet, popcorn), cotton, hops, jojoba, peanuts, rice, safflower, small grains (barley, oats, rye, wheat, etc.), sorghum, soybeans, sunflowers, and tobacco are often targets for infestation by insects including armyworm, asian and other corn borers, banded sunflower moth, beet armyworm, bollworm, cabbage looper, corn rootworm (including southern and western varieties), cotton leaf perforator, diamondback moth, european corn borer, green cloverworm, headmoth, headworm, imported cabbageworm, loopers (including *Anacamptodes* spp.), obliquebanded leafroller, omnivorous leaftier, podworm, podworm, saltmarsh caterpillar, southwestern corn borer, soybean looper, spotted cutworm, sunflower moth, tobacco budworm, tobacco hornworm, velvetbean caterpillar, Bedding plants, flowers, ornamentals, vegetables and container stock are frequently fed upon by a host of insect pests such as armyworm, azalea moth, beet armyworm, diamondback moth, ello moth (hornworm), Florida fern caterpillar, Io moth, loopers, oleander moth, omnivorous leafroller, omnivorous looper, and tobacco budworm.

Forests, fruit, ornamental, and nut-bearing trees, as well as shrubs and other nursery stock are often susceptible to attack from diverse insects such as bagworm, blackheaded budworm, browntail moth, California oakworm, douglas fir tussock moth, elm spanworm, fall webworm, fruittree leafroller, greenstriped mapleworm, gypsy moth, jack pine budworm, mimosa webworm, pine butterfly, redhumped caterpillar, saddleback caterpillar, saddle prominent caterpillar, spring and fall cankerworm, spruce budworm, tent caterpillar, tortrix, and western tussock moth. Likewise, turf grasses are often attacked by pests such as armyworm, sod webworm, and tropical sod webworm.

TABLE 1

TAXONOMY OF COLEOPTERAN PESTS IN THE SUBORDERS *ARCHOSTEMATA* AND *POLYPHAGA*

| Infraorder | Superfamily | Family | Subfamily | Tribe | Genus | Species |
|---|---|---|---|---|---|---|
| | | *Cupedidae* (reticulated beetles) | | | *Priacma* | *P. serrata* |
| *Bostrichiformia* | | *Dermestidae* (skin and larder beetles) | | | *Attagenus* | *A. pellio* |
| *Chrysomeliformia* | | *Cerambycidae* (long-horned beetles) | | | *Agapanthia* | *Agapanthia* sp. |

TABLE 1-continued

TAXONOMY OF COLEOPTERAN PESTS IN THE SUBORDERS *ARCHOSTEMATA* AND *POLYPHAGA*

| Infraorder | Super-family | Family | Subfamily | Tribe | Genus | Species |
|---|---|---|---|---|---|---|
| | | | *Lepturinae* | | *Leptura* | *Leptura* sp. (flower long-horned beetle) |
| | | | | | *Rhagium* | *Rhagium* sp. |
| | | | | | *Megacyllene* | *M. robiniae* |
| | | | *Prioninae* | | *Derobrachus* | *D. geminatus* |
| | | | | | *Tetraopes* | *T. tetropthalmus* |
| | | *Chrysomelidae* (leaf beetles) | *Chlamisinae* | | *Exema* | *E. neglecta* |
| | | | *Chrysomelinae* | *Chrysomelini* | *Chrysomela* | *C. tremula*, *Chrysomela* sp. |
| | | | | | *Oreina* | *O. cacaliae* |
| | | | | *Doryphorini* | *Chrysoline* | *Chrysolina* sp. |
| | | | | | *Leptinotarsa* | *L. decemlineata* (Colorado potato beetle) |
| | | | | *Gonioctenini* | *Gonioctena* | *G. fornicata*, *G. holdausi*, *G. intermedia*, *G. interposita*, *G. kamikawai*, *G. linnaeana*, *G. nigroplagiata*, *G. occidentalis*, *G. olivacea*, *G. pallida*, *G. quinquepunctata*, *G. rubripennis*, *G. rufipes*, *G. tredecim-maculata*, *G. variabilis*, *G. viminalis* |
| | | | | *Timarchini* | *Timarcha* | *Timarcha* sp. |
| | | | *Criocerinae* | | *Oulema* | *Oulema* sp. |
| | | | *Galerucinae* | *Galerucini* | *Monoxia* | *M. inornata*, *Monoxia* sp. |
| | | | | | *Ophraella* | *O. arctica*, *O. artemisiae*, *O. bilineata*, *O. communa*, *O. conferta*, *O. cribrata*, *O. notata*, *O. notulata*, *O. nuda*, *O. pilosa*, *O. sexvittata*, *O. slobodkini* |
| | | | | *Luperini* | *Cerotoma* | *C. trifurcata* |
| | | | | | *Diabrotica* | *D. barberi* (northern corn rootworm), *D. undecimpunctata*, (southern corn rootworm), *D. virgifera* (western corn rootworm) |
| | | | unclassified *Chrysomelidae* | | *Lachnaia* | *Lachnaia* sp. |
| | | | | | *Epitrix* | *E. cucumeris* (Harris) (potato flea beetle), *E. fuscala* (eggplant flea beetle) |
| | | *Curculionidae* (weevils) | *Curculioninae* | | *Anthonomus* | *A. grandis* (boll weevil) |
| | | | *Entiminae* | *Naupactini* | *Aramigus* | *A. conirostris*, *A. globoculus*, *A. intermedius*, *A. planioculus*, *A. tesselatus* |
| | | | | | *Otiorhynchus* | *Otiorhynchus* sp. |
| | | | | *Phyllobiini* | *Diaprepes* | *D. abbreviata* |
| | | | | | *Phyllobius* | *Phyllobius* sp. |
| | | | | | *Galapaganus* | *G. galapagoensis* |
| | | | *Hyperinae* | | *Hypera* | *H. brunneipennis* (Egyptian alfalfa weevil), *H. postica* (alfalfa weevil), *H. punctata* (clover leaf weevil) |
| | | | *Molytinae* | | *Pissodes* | *P. affinis*, *P. nemorensis*, *P. schwarzi*, *P. strobi*, *P. terminalis* |
| | | | *Rhynchophorinae* | *Sitophilini* | *Sitophilus* | *S. granarius* (granary weevil), *S. zeamais* (maize weevil) |
| | | *Nemonychidae* | | | *Lebanorhinus* | *L. succinus* |
| | | *Scolytidae* | | | *Ips* | *I. acuminatus*, *I. amitinus*, *I. cembrae*, *I. duplicatus*, *I. mannsfeldi*, *I. sexdentatus*, *I. typographus* |
| | | | | | *Orthotomicus* | *O. erosus* |
| | | | | | *Tomicus* | *T. minor* |
| *Cucujiformia* | | *Coccinellidae* (ladybird beetles) | | | *Epilachna* | *E. borealis* (squash ladybird beetle), *E. varivstis* (Mexican bean beetle) |
| | | *Cucujidae* (flat bark beetles) | | | *Cryptolestes* | *C. ferrugineus* |

TABLE 1-continued

TAXONOMY OF COLEOPTERAN PESTS IN THE SUBORDERS *ARCHOSTEMATA* AND *POLYPHAGA*

| Infraorder | Super-family | Family | Subfamily | Tribe | Genus | Species |
|---|---|---|---|---|---|---|
| | | | | | *Oryzaephilus* (grain beetles) | *O. surinamensis* (saw-toothed grain beetle) |
| | | *Lagriidae* (long-joined beetles) | | | *Lagria* | *Lagria* sp. |
| | | *Meloidae* (blister beetles) | | | *Epicauta* | *E. funebris* |
| | | | | | *Meloe* | *M. proscarabaeus* |
| | | *Rhipiphoridae* | | | *Rhipiphorus* | *R. fasciatus* |
| | | *Tenebrionidae* (darkling ground beetles) | | | *Alphitobius* | *A. diaperinus* (lesser mealworm) |
| | | | | | *Hegeter* | *H. amaroides*, *H. brevicollis*, *H. costipennis*, *H. fernandez*, *H. glaber*, *H. gomerensis*, *H. grancanariensis*, *H. impressus*, *H. intercedens*, *H. lateralis*, *H. plicifrons*, *H. politus*, *H. subrotundatus*, *H. tenuipunctatus*, *H. transversus*, *H. webbianus* |
| | | | | | *Misolampus* | *M. goudoti* |
| | | | | | *Palorus* | *P. ficicola*, *P. ratzeburgi* (small-eyed flour beetle), *P. subdepressus* (depressed flour beetle) |
| | | | | | *Pimelia* | *P. baetica*, *P. canariensis*, *P. criba*, *P. elevate*, *P. estevezi*, *P. fernan-dezlopezi*, *P. grandis*, *P. granulicollis*, *P. integra*, *P. interjecta*, *P. laevigata*, *P. lutaria*, *P. radula*, *P. sparse*, *P. variolosa* |
| | | | | | *Tenebrio* | *T. molitor* (yellow mealworm), *T. obscurus* (dark mealworm) |
| | | | | | *Tentyria* | *T. schaumi* |
| | | | | | *Tribolium* | *T. brevicornis*, *T. castaneum* (red flour beetle), *T. confusum* (confused flour beetle), *T. freemani*, *T. madens* |
| | | | | | *Zophobas* | *Z. atratus* |
| | | | | | | *Z. rugipes* |
| *Elateriformia* | *Elateroidea* | | | | *Octinodes* | *Octinodes* sp. |
| | | | | | *Pyrophorus* | *P. plagio-phthalamus* |
| *Scarabaeiformia* | | *Lucanidae* (Stag beetles) | | | *Dorcus* | *D. parallelo-pipedus* |
| | | | | | *Lucanus* | *L. cervus* |
| | | *Scarabaeidae* (lamellicorn beetles) | | | *Allomyrina* | *A. dichotoma* |
| | | | *Cetoniinae* (flower beetle) | | *Pachnoda* | *P. marginata* |
| | | | *Dynastinae* | | *Xyloryctes* | *X. faunus* |
| | | | *Geotrupinae* (earth-boring dung beetles) | | *Geotrupes* | *G. stercorosus* |
| | | | *Melonlonthinae* (chafers) | | *Costelytra* | *C. zealandica* |
| | | | | | *Holotrichia* | *H. diomphalia* |
| | | | | | *Melolontha* | *M. melolontha* (cockchafer) |
| | | | | | *Odontria* | *O. striata* |
| | | | | | | *O. variegata* |
| | | | | | *Prodontria* | *P. bicolorata*, *P. capito*, *P. lewisi*, *P. tarsis*, *P. modesta*, *P. pinguis*, *P. praelatella*, *P. truncata*, *Prodontria* sp. |
| | | | | | *Scythrodes* | *S. squalidus* |
| | | | *Rutelinae* (shining leaf chafers) | | *Popillia* | *P. japonica* (Japanese beetle) |
| | | | *Scarabaeinae* | | *Copris* | *C. lunaris* (black dung beetle) |
| | | | | | *Scarabaeus* | *Scarabaeus* sp. (scarab) |

TABLE 1-continued

| TAXONOMY OF COLEOPTERAN PESTS IN THE SUBORDERS *ARCHOSTEMATA* AND *POLYPHAGA* | | | | | | |
|---|---|---|---|---|---|---|
| Infraorder | Super-family | Family | Subfamily | Tribe | Genus | Species |
| *Staphyliniformia* | | *Hydrophilidae* | | | *Cercyon* | *Cercyon* sp. |
| | | *Silphidae* | | | *Nicrophorus* | *N. americanus, N. marginatus, N. orbicollis, N. tomentosus* |
| | | *Staphylinidae* (rove beetles) | | | *Carpelimus* | *Carpelimus* sp. |
| | | | | | *Quedius* | *Q. mesomelinus* |
| | | | | | *Tachyporus* | *Tachyporus* sp. |
| | | | | | *Xantholinus* | *Xantholinus* sp. |

4.3 Nomenclature of *B. thuringiensis* δ-Endotoxins

Table 2 contains a list of the traditional, and currently recognized nomenclature for the known δ-endotoxins. Also shown are GenBank accession numbers for the sequenced polypeptides and polynucleotides.

TABLE 2

| NOMENCLATURE OF KNOWN *B. THURINGIENSIS* δ-ENDOTOXINS[A] | | |
|---|---|---|
| New | Old | GenBank Accession # |
| Cry1Aa1 | CryIA(a) | M11250 |
| Cry1Aa2 | CryIA(a) | M10917 |
| Cry1Aa3 | CryIA(a) | D00348 |
| Cry1Aa4 | CryIA(a) | X13535 |
| Cry1Aa5 | CryIA(a) | D175182 |
| Cry1Aa6 | CryIA(a) | U43605 |
| Cry1Aa7 | | AF081790 |
| Cry1Aa8 | | I26149 |
| Cry1Aa9 | | AB026261 |
| Cry1Ab1 | CryIA(b) | M13898 |
| Cry1Ab2 | CryIA(b) | M12661 |
| Cry1Ab3 | CryIA(b) | M15271 |
| Cry1Ab4 | CryIA(b) | D00117 |
| Cry1Ab5 | CryIA(b) | X04698 |
| Cry1Ab6 | CryIA(b) | M37263 |
| Cry1Ab7 | CryIA(b) | X13233 |
| Cry1Ab8 | CryIA(b) | M16463 |
| Cry1Ab9 | CryIA(b) | X54939 |
| Cry1Ab10 | CryIA(b) | A29125 |
| Cry1Ab11 | | I12419 |
| Cry1Ab12 | | AF057670 |
| Cry1Ac1 | CryIA(c) | M11068 |
| Cry1Ac2 | CryIA(c) | M35524 |
| Cry1Ac3 | CryIA(c) | X54159 |
| Cry1Ac4 | CryIA(c) | M73249 |
| Cry1Ac5 | CryIA(c) | M73248 |
| Cry1Ac6 | CryIA(c) | U43606 |
| Cry1Ac7 | CryIA(c) | U87793 |
| Cry1Ac8 | CryIA(c) | U87397 |
| Cry1Ac9 | CryIA(c) | U89872 |
| Cry1Ac10 | CryIA(c) | AJ002514 |
| Cry1Ac11 | | AJ130970 |
| Cry1Ac12 | | I12418 |
| Cry1Ad1 | CryIA(d) | M73250 |
| Cry1Ad2 | | A27531 |
| Cry1Ae1 | CryIA(e) | M65252 |
| Cry1Af1 | | U82003 |
| Cry1Ag1 | | AF081248 |
| Cry1Ba1 | CryIB | X06711 |
| Cry1Ba2 | | X95704 |
| Cry1Bb1 | ET5 | L32020 |
| Cry1Bc1 | CryIb(c) | Z46442 |
| Cry1Bd1 | CryE1 | U70726 |

TABLE 2-continued

| NOMENCLATURE OF KNOWN *B. THURINGIENSIS* δ-ENDOTOXINS[A] | | |
|---|---|---|
| New | Old | GenBank Accession # |
| Cry1Ca1 | CryIC | X07518 |
| Cry1Ca2 | CryIC | X13620 |
| Cry1Ca3 | CryIC | M73251 |
| Cry1Ca4 | CryIC | A27642 |
| Cry1Ca5 | CryIC | X96682 |
| Cry1Ca6 | CryIC | X96683 |
| Cry1Ca7 | CryIC | X96684 |
| Cry1Cb1 | CryIC(b) | M97880 |
| Cry1Da1 | CryID | X54160 |
| Cry1Da2 | | I76415 |
| Cry1Db1 | PrtB | Z22511 |
| Cry1Ea1 | CryIE | X53985 |
| Cry1Ea2 | CryIE | X56144 |
| Cry1Ea3 | CryIE | M73252 |
| Cry1Ea4 | | U94323 |
| Cry1Ea5 | | A15535 |
| Cry1Eb1 | CryIE(b) | M73253 |
| Cry1Fa1 | CryIF | M63897 |
| Cry1Fa2 | CryIF | M63897 |
| Cry1Fb1 | PrtD | Z22512 |
| Cry1Fb2 | | Z22512 |
| Cry1Fb3 | | AF062350 |
| Cry1Fb4 | | I73895 |
| Cry1Ga1 | PrtA | Z22510 |
| Cry1Ga2 | CryIM | Y09326 |
| Cry1Gb1 | CryH2 | U70725 |
| Cry1Ha1 | PrtC | Z22513 |
| Cry1Hb1 | | U35780 |
| Cry1Ia1 | CryV | X62821 |
| Cry1Ia2 | CryV | M98544 |
| Cry1Ia3 | CryV | L36338 |
| Cry1Ia4 | CryV | L49391 |
| Cry1Ia5 | CryV | Y08920 |
| Cry1Ia6 | | AF076953 |
| Cry1Ib1 | CryV | U07642 |
| Cry1Ic1 | | AF056933 |
| Cry1Ja1 | ET4 | L32019 |
| Cry1Jb1 | ET1 | U31527 |
| Cry1Jc1 | | AF056933 |
| Cry1Ka1 | | U28801 |
| Cry2Aa1 | CryIIA | M31738 |
| Cry2Aa2 | CryIIA | M23723 |
| Cry2Aa3 | | D86084 |
| Cry2Aa4 | | AF047038 |
| Cry2Aa5 | | AJ132464 |
| Cry2Aa6 | | AJ1324635 |
| Cry2Aa7 | | AJ132463 |
| Cry2Ab1 | CryIIB | M23724 |
| Cry2Ab2 | CryIIB | X55416 |
| Cry2Ac1 | CryIIC | X57252 |

TABLE 2-continued

NOMENCLATURE OF KNOWN *B. THURINGIENSIS* δ-ENDOTOXINS[A]

| New | Old | GenBank Accession # |
|---|---|---|
| Cry3Aa1 | CryIIIA | M22472 |
| Cry3Aa2 | CryIIIA | J02978 |
| Cry3Aa3 | CryIIIA | Y00420 |
| Cry3Aa4 | CryIIIA | M30503 |
| Cry3Aa5 | CryIIIA | M37207 |
| Cry3Aa6 | CryIIIA | U10985 |
| Cry3Aa7 | | AJ237900 |
| Cry3Ba1 | CryIIIB | X17123 |
| Cry3Ba2 | CryIIIB | A07234 |
| Cry3Bb1 | CryIIIB2 | M89794 |
| Cry3Bb2 | CryIIIC(b) | U31633 |
| Cry3Bb3 | | I15475 |
| Cry3Ca1 | CryIIID | X59797 |
| Cry4Aa1 | CryIVA | Y00423 |
| Cry4Aa2 | CryIVA | D00248 |
| Cry4Ba1 | CryIVB | X07423 |
| Cry4Ba2 | CryIVB | X07082 |
| Cry4Ba3 | CryIVB | M20242 |
| Cry4Ba4 | CryIVB | D00247 |
| Cry5Aa1 | CryVA(a) | L07025 |
| Cry5Ab1 | CryVA(b) | L07026 |
| Cry5Ac1 | | I34543 |
| Cry5Ba1 | PS86Q3 | U19725 |
| Cry6Aa1 | CryVIA | L07022 |
| Cry6Ba1 | CryVIB | L07024 |
| Cry7Aa1 | CryIIIC | M64478 |
| Cry7Ab1 | CryIIICb | U04367 |
| Cry7Ab2 | | U04368 |
| Cry8Aa1 | CryIIIE | U04364 |
| Cry8Ba1 | | U04365 |
| Cry8Ca1 | | U04366 |
| Cry8Ba1 | CryIIIG | U04365 |
| Cry8Ca1 | CryIIIF | U04366 |
| Cry9Aa1 | CryIG | X58120 |
| Cry9Aa2 | CryIG | X58534 |
| Cry9Ba1 | CryIX | X75019 |
| Cry9Ca1 | CryIH | Z37527 |
| Cry9Da1 | N141 | D85560 |
| Cry9Da2 | | AF042733 |
| Cry9Ea1 | | |
| Cry10Aa1 | CryIVC | M12662 |
| Cry10Aa2 | | E00614 |
| Cry11Aa1 | CryIVD | M31737 |
| Cry11Aa2 | CryIVD | M22860 |
| Cry11Ba1 | Jeg80 | X86902 |
| Cry11Bb1 | | AF017416 |
| Cry12Aa1 | CryVB | L07027 |
| Cry13Aa1 | CryVC | L07023 |
| Cry14Aa1 | CryVD | U13955 |
| Cry15Aa1 | 34 kDa | M76442 |
| Cry16Aa1 | cbm71 | X94146 |
| Cry17Aa1 | cbm71 | X99478 |
| Cry18Aa1 | CryBP1 | X99049 |
| Cry19Aa1 | Jeg65 | Y08920 |
| Cry20Aa1 | | U82518 |
| Cry21Aa1 | | I32932 |
| Cry22Aa1 | | I34547 |
| Cry23Aa1 | | AF03048 |
| Cry24Aa1 | | U88188 |
| Cry25Aa1 | | U88189 |
| Cry26Aa1 | | AF122897 |
| Cry27Aa1 | | AB023293 |
| Cry28Aa1 | | AF132928 |
| Cyt1Aa1 | CytA | X03182 |
| Cyt1Aa2 | CytA | X04338 |
| Cyt1Aa3 | CytA | Y00135 |
| Cyt1Aa4 | CytA | M35968 |
| Cyt1Ab1 | CytM | X98793 |
| Cyt1Ba1 | | U37196 |
| Cyt2Aa1 | CytB | Z14147 |
| Cyt2Ba1 | "CytB" | U52043 |
| Cyt2Ba2 | "CytB" | AF020789 |
| Cyt2Ba3 | "CytB" | AF022884 |
| Cyt2Ba4 | "CytB" | AF022885 |
| Cyt2Ba5 | "CytB" | AF022886 |
| Cyt2Ba6 | | AF034926 |
| Cyt2Bb1 | | U82519 |
| Cyt2Bb1 | | U82519 |

[A]Adapted from: Crickmore, N. et al. Microbiol. and Mol. Bio. Rev. (1998) Vol. 62: 807-813.

4.4 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein-encoding gene sequence, e.g., a sequence such as that disclosed herein. The ability of such DNAs and nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCR™ using such primers.

To provide certain of the advantages in accordance with the present invention, a preferred nucleic acid sequence employed for hybridization studies or assays includes sequences that are complementary to at least an about 23 to about 40 or so long nucleotide stretch of a crystal protein-encoding sequence, such as that shown herein. A size of at least about 14 or 15 or so nucleotides in length helps to ensure that the fragment will be of sufficient length to form a duplex molecule that is both stable and selective. Molecules having complementary sequences over stretches greater than about 23 or so bases in length are generally preferred, though, in order to increase stability and selectivity of the hybrid, and thereby improve the quality and degree of specific hybrid molecules obtained. One will generally prefer to design nucleic acid molecules having gene-complementary stretches of about 14 to about 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, specifically incorporated herein by reference, or by excising selected DNA fragments from recombinant plasmids containing appropriate inserts and suitable restriction sites.

4.5 Expression Vectors

The present invention contemplates a polynucleotide of the present invention comprised within one or more expression vectors. Thus, in one embodiment an expression vector comprises a nucleic acid segment containing a crystal protein-encoding gene operably linked to a promoter which expresses the gene. Additionally, the coding region may also be operably linked to a transcription-terminating region, whereby the promoter drives the transcription of the coding region, and the transcription-terminating region halts transcription at some point 3' of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus*-derived crystal proteins include any of the known crystal protein gene promoters, including the cry gene promoters themselves. Alternatively, mutagenized or recombinant promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991a). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35S transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are specifically incorporated herein by reference in their entirety. Those vectors can be modified to include a coding sequence in accordance with the present invention.

A variety of methods has been developed to operatively insert a DNA segment into a vector via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a *B. thuringiensis* crystal protein-encoding gene. In preferred embodiments, such a polypeptide has the amino acid residue sequence of one of the sequences disclosed herein, or a functional equivalent thereof. In accordance with such embodiments, a coding region comprising the DNA sequence of such a sequence is also preferred

4.8 Nomenclature of the Novel Proteins

The inventors have arbitrarily assigned designations to the novel proteins of the invention. Likewise, the arbitrary gene designations have been assigned to the novel nucleic acid sequence which encodes these polypeptides. Formal assignment of gene and protein designations based on the revised nomenclature of crystal protein endotoxins will be assigned by a committee on the nomenclature of *B. thuringiensis*, formed to systematically classify *B. thuringiensis* crystal proteins. The inventors contemplate that the arbitrarily assigned designations of the present invention will be superseded by the official nomenclature assigned to these sequences.

4.9 Transformed Host Cells and Transgenic Plants

Methods and compositions for transforming a bacterium, a yeast cell, a plant cell, or an entire plant with one or more expression vectors comprising a crystal protein-encoding gene segment are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988a; Eglitis et al., 1988); and (4) receptor-mediated mechanisms (Curiel et al., 1991; 1992; Wagner et al., 1992).

4.9.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.9.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hr post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.9.3 *Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modem *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors as described (Bytebier et al., 1987). Therefore, commercially important cereal grains such as rice, corn, and wheat must usually be transformed using alternative methods. However, as mentioned above, the transformation of asparagus using *Agrobacterium* can also be achieved (see, for example, Bytebier et al., 1987).

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

4.9.4 Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil et al., 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.9.5 Gene Expression in Plants

Although great progress has been made in recent years with respect to preparation of transgenic plants which express bacterial proteins such as *B. thuringiensis* crystal proteins, the results of expressing native bacterial genes in plants are often disappointing. Unlike microbial genetics, little was known by early plant geneticists about the factors which affected heterologous expression of foreign genes in plants. In recent years, however, several potential factors have been implicated as responsible in varying degrees for the level of protein expression from a particular coding sequence. For example, scientists now know that maintaining a significant level of a particular mRNA in the cell is indeed a critical factor. Unfortunately, the causes for low steady state levels of mRNA encoding foreign proteins are many. First, full length RNA synthesis may not occur at a high frequency. This could, for example, be caused by the premature termination of RNA during transcription or due to unexpected mRNA processing during transcription. Second, full length RNA may be produced in the plant cell, but then processed (splicing, polyA addition) in the nucleus in a fashion that creates a nonfunctional mRNA. If the RNA is not properly synthesized, terminated and polyadenylated, it cannot move to the cytoplasm for translation. Similarly, in the cytoplasm, if mRNAs have reduced half lives (which are determined by their primary or secondary sequence) insufficient protein product will be produced. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure It is likely that structure per se or particular structural features also have a role in determining RNA stability.

To overcome these limitations in foreign gene expression, researchers have identified particular sequences and signals in RNAs that have the potential for having a specific effect on RNA stability. In certain embodiments of the invention, therefore, there is a desire to optimize expression of the disclosed nucleic acid segments in planta. One particular method of doing so, is by alteration of the bacterial gene to remove sequences or motifs which decrease expression in a transformed plant cell. The process of engineering a coding sequence for optimal expression in planta is often referred to as "plantizing" a DNA sequence.

Particularly problematic sequences are those which are A+T rich. Unfortunately, since *B. thuringiensis* has an A+T rich genome, native crystal protein gene sequences must often be modified for optimal expression in a plant. The sequence motif ATTTA (or AUUUA as it appears in RNA) has been implicated as a destabilizing sequence in mammalian cell mRNA (Shaw and Kamen, 1986). Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabiling elements or whether any of these effects are likely to be seen in plants.

Some studies on mRNA degradation in animal cells also indicate that RNA degradation may begin in some cases with nucleolytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA. Another example is the differential stability of IgG mRNA in B lymphocytes during B cell maturation (Genovese and Milcarek, 1988). These examples all provide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is common to most eukaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Studies in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e. a gene that has a normal AATAAA but has been replaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occurring mRNAs that are normally polyadenylated, it has been observed that disruption of this process, either by altering the polyA signal or other sequences in the mRNA, profound effects can be obtained in the level of functional mRNA. This has been observed in several naturally occurring mRNAs, with results that are gene-specific so far.

It has been shown that in natural mRNAs proper polyadenylation is important in mRNA accumulation, and that disruption of this process can effect mRNA levels significantly. However, insufficient knowledge exists to predict the effect of changes in a normal gene. In a heterologous gene, it is even harder to predict the consequences. However, it is possible that the putative sites identified are dysfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites in Table 3 called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as those encoding the crystal proteins of the present invention.

TABLE 3

| POLYADENYLATION SITES IN PLANT GENES | | |
|---|---|---|
| PA | AATAAA | Major consensus site |
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

As described above, the expression of native *B. thuringiensis* genes in plants is often problematic. The nature of the coding sequences of *B. thuringiensis* genes distinguishes them from plant genes as well as many other heterologous genes expressed in plants. In particular, *B. thuringiensis* genes are very rich (~62%) in adenine (A) and thymine (T) while plant genes and most other bacterial genes which have been expressed in plants are on the order of 45-55% A+T.

Due to the degeneracy of the genetic code and the limited number of codon choices for any amino acid, most of the "excess" A+T of the structural coding sequences of some *Bacillus* species are found in the third position of the codons. That is, genes of some *Bacillus* species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis.*

Typically, to obtain high-level expression of the δ-endotoxin genes in plants, existing structural coding sequence ("structural gene") which codes for the δ-endotoxin are modified by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

The selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the about 15 to about 30 or so nucleotide residues surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

4.9.6 Synthetic Oligonucleotides for Mutagenesis

When oligonucleotides are used in the mutagenesis, it is desirable to maintain the proper amino acid sequence and reading frame, without introducing common restriction sites such as BglII, HindIII, SacI, KpnI, EcoRI, NcoI, PstI and SalI into the modified gene. These restriction sites are found in poly-linker insertion sites of many cloning vectors. Of course, the introduction of new polyadenylation signals, ATTTA sequences or consecutive stretches of more than five A+T or G+C, should also be avoided. The preferred size for the oligonucleotides is about 40 to about 50 bases, but fragments ranging from about 18 to about 100 bases have been utilized. In most cases, a minimum of about 5 to about 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table 4 below) so as to avoid codons which are rarely found in plant genomes, and efforts should be made to select codons to preferably adjust the G+C content to about 50%.

TABLE 4

PREFERRED CODON USAGE IN PLANTS

| Amino Acid | Codon | Percent Usage in Plants |
|---|---|---|
| ARG | CGA | 7 |
| | CGC | 11 |
| | CGG | 5 |
| | CGU | 25 |
| | AGA | 29 |
| | AGG | 23 |
| LEU | CUA | 8 |
| | CUC | 20 |
| | CUG | 10 |
| | CUU | 28 |
| | UUA | 5 |
| | UUG | 30 |
| SER | UCA | 14 |
| | UCC | 26 |
| | UCG | 3 |
| | UCU | 21 |
| | AGC | 21 |
| | AGU | 15 |
| THR | ACA | 21 |
| | ACC | 41 |
| | ACG | 7 |
| | ACU | 31 |
| PRO | CCA | 45 |
| | CCC | 19 |
| | CCG | 9 |
| | CCU | 26 |
| ALA | GCA | 23 |
| | GCC | 32 |
| | GCG | 3 |
| | GCU | 41 |
| GLY | GGA | 32 |
| | GGC | 20 |
| | GGG | 11 |
| | GGU | 37 |
| ILE | AUA | 12 |
| | AUC | 45 |
| | AUU | 43 |
| VAL | GUA | 9 |
| | GUC | 20 |
| | GUG | 28 |
| | GUU | 43 |
| LYS | AAA | 36 |
| | AAG | 64 |
| ASN | AAC | 72 |
| | AAU | 28 |
| GLN | CAA | 64 |
| | CAG | 36 |
| HIS | CAC | 65 |
| | CAU | 35 |
| GLU | GAA | 48 |
| | GAG | 52 |
| ASP | GAC | 48 |
| | GAU | 52 |
| TYR | UAC | 68 |
| | UAU | 32 |
| CYS | UGC | 78 |
| | UGU | 22 |
| PHE | UUC | 56 |
| | UUU | 44 |
| MET | AUG | 100 |
| TRP | UGG | 100 |

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators).

Alternatively, a completely synthetic gene for a given amino acid sequence can be prepared, with regions of five or more consecutive A+T or G+C nucleotides being avoided. Codons are selected avoiding the TA and CG doublets in codons whenever possible. Codon usage can be normalized against a plant preferred codon usage table (such as Table 4) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

4.10 Methods for Producing Insect-Resistant Transgenic Plants

By transforming a suitable host cell, such as a plant cell, with a recombinant cry gene-containing segment, the expression of the encoded crystal protein (i.e. a bacterial crystal protein or polypeptide having insecticidal activity against Coleopterans) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a gene) that encodes a polypeptide as disclosed herein. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects, preferably in the field, under a range of environmental conditions. The inventors contemplate that the present invention will find particular utility in the creation of transgenic plants of commercial interest including various turf and pasture grasses, rye, wheat, corn, kapok, flax, rice, barley, oats, sugarcane, cotton, tomato, potato, soybeans and other legumes, tobacco, sorghum, as well as a variety of ornamental plants including cacti and succulents, fruits, berries, vegetables, and also a number of nut- and fruit-bearing trees and plants.

Transgenic plants comprising one or more transgenes that encode a polypeptide as described herein will preferably exhibit a phenotype of improved or enhanced insect resistance to the target coleopteran and lepidopteran insects as described herein. These plants will preferably provide transgenic seeds, which will be used to create lineages of transgenic plants (i.e. progeny or advanced generations of the original transgenic plant) that may be used to produce seed, or used as animal or human foodstuffs, or to produce fibers, oil, fruit, grains, or other commercially-important plant products or plant-derived components. In such instances, the progeny and seed obtained from any generation of the transformed plants will contain the selected chromosomally-integrated transgene that encodes the δ-endotoxin of the present invention. The transgenic plants of the present invention may be crossed to produce hybrid or inbred lines with one or more plants that have desirable properties. In certain circumstances, it may also be desirable to create transgenic plants, seed, and progeny that contain one or more additional transgenes incorporated into their genome in addition to the transgene encoding the polypeptide of the invention. For example, the transgenic plants may contain a second gene encoding the same, or a different insect-resistance polypeptide, or alternatively, the plants may comprise one or more additional transgenes such as those conferring herbicide resistance, fungal resistance, bacterial resistance, stress, salt, or drought tolerance, improved stalk or root lodging, increased starch, grain, oil, carbohydrate, amino acid, protein production, and the like.

4.11 Isolating Homologous Gene and Gene Fragments

The genes and δ-endotoxins according to the subject invention include not only the full length sequences disclosed herein but also fragments of these sequences, or fusion proteins, which retain the characteristic insecticidal activity of the sequences specifically exemplified herein.

It should be apparent to a person skill in this art that insecticidal δ-endotoxins can be identified and obtained through several means. The specific genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these δ-endotoxins.

Equivalent δ-endotoxins and/or genes encoding these equivalent δ-endotoxins can also be isolated from *Bacillus* strains and/or DNA libraries using the teachings provided herein. For example, antibodies to the δ-endotoxins disclosed and claimed herein can be used to identify and isolate other δ-endotoxins from a mixture of proteins. Specifically, antibodies may be raised to the portions of the δ-endotoxins which are most constant and most distinct from other *B. thuringiensis* δ-endotoxins. These antibodies can then be used to specifically identify equivalent δ-endotoxins with the characteristic insecticidal activity by immunoprecipitation, enzyme linked immunoassay (ELISA), or Western blotting.

A further method for identifying the δ-endotoxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal δ-endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxin, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed is due, in part, to the redundancy of the genetic code. Because of the redundancy of the genetic code, i.e. more than one coding nucleotide triplet (codon) can be used for most of the amino acids used to make proteins. Therefore different nucleotide sequences can code for a particular amino acid. Thus, the amino acid sequences of the *B. thuringiensis* δ-endotoxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein which do not alter the protein secondary structure, or if the structure is altered, the biological activity is substantially retained. Further, the invention also includes mutants of organisms hosting all or part of a δ-endotoxin encoding a gene of the invention. Such mutants can be made by techniques well known to persons skilled in the art. For example, UV irradiation can be used to prepare mutants of host organisms. Likewise, such mutants may include asporogenous host cells which also can be prepared by procedures well known in the art.

4.13 Recombinant Host Cells

The nucleotide sequences of the subject invention may be introduced into a wide variety of microbial and eukaryotic hosts. As hosts for recombinant expression of Cry polypeptides, of particular interest will be the prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae, *Actinomycetales*, and Nitrobacteraceae. Among eukaryotes are fungi, such as

*Phycomycetes* and *Ascomycetes*, which includes yeast, such as *Saccharomyces* and *Schizosaccharomyces*; and *Basidiomycetes* yeast, such as *Rhodotorula*, *Aureobasidium*, *Sporobolomyces*, and the like.

Characteristics of particular interest in selecting a host cell for purposes of production include ease of introducing the genetic constructs of the present invention into the host cell, availability of expression systems, efficiency of expression, stability of the gene of interest in the host, and the presence of auxiliary genetic capabilities.

A large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed genetic constructs. These microorganisms include bacteria, algae, and fungi. Of particular interest are microorganisms, such as bacteria, e.g., genera *Bacillus* (including the species and subspecies *B. thuringiensis kurstaki* HD-1, *B. thuringiensis kurstaki* HD-73, *B. thuringiensis sotto*, *B. thuringiensis berliner*, *B. thuringiensis thuringiensis*, *B. thuringiensis tolworthi*, *B. thuringiensis dendrolimus*, *B. thuringiensis alesti*, *B. thuringiensis galleriae*, *B. thuringiensis aizawai*, *B. thuringiensis subtoxicus*, *B. thuringiensis entomocidus*, *B. thuringiensis tenebrionis* and *B. thuringiensis san diego*); *Pseudomonas*, *Erwinia*, *Serratia*, *Klebsiella*, *Zanthomonas*, *Streptomyces*, *Rhizobium*, *Rhodopseudomonas*, *Methylophilius*, *Agrobacterium*, *Acetobacter*, *Lactobacillus*, *Arthrobacter*, *Azotobacter*, *Leuconostoc*, and *Alcaligenes*; fungi, particularly yeast, e.g., genera *Saccharomyces*, *Cryptococcus*, *Kluyveromyces*, *Sporobolomyces*, *Rhodotorula*, and *Aureobasidium*. Of particular interest are such phytosphere bacterial species as *Pseudomonas syringae*, *Pseudomonas fluorescens*, *Serratia marcescens*, *Acetobacter xylinum*, *Agrobacterium tumefaciens*, *Rhodobacter sphaeroides*, *Xanthomonas campestris*, *Rhizobium melioti*, *Alcaligenes eutrophus*, and *Azotobacter vinlandii*; and phytosphere yeast species such as *Rhodotorula rubra*, *R. glutinis*, *R. marina*, *R. aurantiaca*, *Cryptococcus albidus*, *C. diffluens*, *C. laurentii*, *Saccharomyces rosei*, *S. pretoriensis*, *S. cerevisiae*, *Sporobolomyces roseus*, *S. odorus*, *Kluyveromyces veronae*, and *Aureobasidium pollulans*.

Characteristics of particular interest in selecting a host cell for purposes of production include ease of introducing a selected genetic construct into the host, availability of expression systems, efficiency of expression, stability of the polynucleotide in the host, and the presence of auxiliary genetic capabilities. Other considerations include ease of formulation and handling, economics, storage stability, and the like.

4.14 Polynucleotide Sequences

DNA compositions encoding the insecticidally-active polypeptides of the present invention are particularly preferred for delivery to recipient plant cells, in the generation of pluripotent plant cells, and ultimately in the production of insect-resistant transgenic plants. For example, DNA segments in the form of vectors and plasmids, or linear DNA fragments, in some instances containing only the DNA element to be expressed in the plant cell, and the like, may be employed.

Vectors, plasmids, phagemids, cosmids, viral vectors, shuttle vectors, baculovirus vectors, BACs (bacterial artificial chromosomes), YACs (yeast artificial chromosomes) and DNA segments for use in transforming cells with a δ-endotoxin-encoding polynucleotide, will, of course, generally comprise at least a first gene that encodes the polypeptide in accordance with SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19, or a gene that encodes a polypeptide that has at least about 80% or 85% or 90% or 95% sequence identity to the amino acid sequence disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:19. These nucleic acid constructs may comprise one or more genes which one desires to introduce into recipient cells. These DNA constructs can include structures such as promoters, enhancers, polylinkers, or regulatory genes as desired. The DNA segment or gene chosen for cellular introduction will often encode a polypeptide which will be expressed in the resultant recombinant cells, such as will result in a screenable or selectable trait and/or which will impart an improved phenotype to the transformed host cell. Alternatively, the nucleic acid constructs may contain antisense constructs, or ribozyme-encoding regions when delivery or introduction of such nucleic acid constructs are desirable.

4.15 Methods for Preparing Mutagenized Polynucleotides

In certain circumstances, it may be desirable to modify or alter one or more nucleotides in one or more of the polynucleotide sequences disclosed herein for the purpose of altering or changing the insecticidal activity or insecticidal specificity of the encoded polypeptide. The mutant sequence is then subsequently amplified. Methods for mutagenizing and amplifying a DNA segment are well-known to those of skill in the art. Mutagenesis of the DNA segments may be made by random or site-specific mutagenesis procedures. The polynucleotides may be modified by the addition, deletion, or substitution of one or more nucleotides from the sequence encoding the insecticidally-active polypeptide.

Particular mutagenesis and amplification methods which may be useful in the practice of the present invention are described by Tomic et al., Michael, et al., Upender et al., Kwoh et al., Frohman, et al., Ohara et al., Wu, et al., Walker et al.; U.S. Pat. Nos. 4,683,195, 4,683,202, 4,800,159, 4,883,750, and; EP320,308 EP329,822; GB 2202328; PCT/US87/00880; PCT/US89/01025; WO 88/10315, WO 89/06700, each of which is incorporated herein by reference in its entirety.

4.16 Post-Transcriptional Events Affecting Expression of Transgenes in Plants In many instances, the level of transcription of a particular transgene in a given host cell is not always indicative of the amount of protein being produced in the transformed host cell. This is often due to post-transcriptional processes, such as splicing, polyadenylation, appropriate translation initiation, and RNA stability, that affect the ability of a transcript to produce protein. Such factors may also affect the stability and amount of mRNA produced from the given transgene. As such, it is often desirable to alter the post-translational events through particular molecular biology techniques. The inventors contemplate that in certain instances it may be desirable to alter the transcription and/or expression of the polypeptide-encoding nucleic acid constructs of the present invention to increase, decrease, or otherwise regulate or control these constructs in particular host cells and/or transgenic plants.

4.16.1 Efficient Initiation of Protein Translation

The 5'-untranslated leader (5'-UTL) sequence of eukaryotic mRNA plays a major role in translational efficiency. Many early chimeric transgenes using a viral promoter used an arbitrary length of viral sequence after the transcription initiation site and fused this to the AUG of the coding region. More recently studies have shown that the 5'-UTL sequence and the sequences directly surrounding the AUG can have a large effect in translational efficiency in host cells and particularly certain plant species and that this effect can be different depending on the particular cells or tissues in which the message is expressed.

In most eukaryotic mRNAs, the point of translational initiation occurs at the AUG codon closest to the 5' cap of the transcript. Comparison of plant mRNA sequences and site directed mutagenesis experiments have demonstrated the existence of a consensus sequence surrounding the initiation codon in plants, 5'-UAAACAAUGGCU-3' (SEQ ID NO:35) (Joshi, 1987; Lutcke et al., 1987). However, consensus sequences will be apparent amongst individual plant species. For example, a compilation of sequences surrounding the initiation codon from 85 maize genes yields a consensus of 5'-(C/G)AUGGCG-3' (Luehrsen et al., 1994). In tobacco protoplasts, transgenes encoding β-glucuronidase (GUS) and bacterial chitinase showed a 4-fold and an 8-fold increase in expression, respectively, when the native sequences of these genes were changed to encode 5'-ACCAUGG-3' (Gallie et al., 1987b; Jones et al., 1988).

When producing chimeric transgenes (i.e. transgenes comprising DNA segments from different sources operably linked together), often the 5'-UTL of plant viruses are used. The alfalfa mosaic virus (AMV) coat protein and brome mosaic virus (BMV) coat protein 5'-UTLs have been shown to enhance mRNA translation 8-fold in electroporated tobacco protoplasts (Gallie et al., 1987a; 1987b). A 67-nucleotide derivative (Ω) of the 5'-UTL of tobacco mosaic virus RNA (TMV) fused to the chloramphenicol acetyltransferase (CAT) gene and GUS gene has been shown to enhance translation of reporter genes in vitro (Gallie et al., 1987a; 1987b; Sleat et al., 1987; Sleat et al., 1988). Electroporation of tobacco mesophyll protoplasts with transcripts containing the TMV leader fused to reporter genes CAT, GUS, and LUC produced a 33-, 21-, and 36-fold level of enhancement, respectively (Gallie et al., 1987a; 1987b; Gallie et al., 1991). Also in tobacco, an 83-nt 5'-UTL of potato virus X RNA was shown to enhance expression of the neomycin phosphotransferese II (NptII) 4-fold (Poogin and Skryabin, 1992).

The effect of a 5'-UTL may be different depending on the plant, particularly between dicots and monocots. The TMV 5'-UTL has been shown to be more effective in tobacco protoplasts (Gallie et al., 1989) than in maize protoplasts (Gallie and Young, 1994). Also, the 5'-UTLs from TMV-Ω (Gallie et al., 1988), AMV-coat (Gehrke et al., 1983; Jobling and Gehrke, 1987), TMV-coat (Goelet et al., 1982), and BMV-coat (French et al., 1986) worked poorly in maize and inhibited expression of a luciferase gene in maize relative to its native leader (Koziel et al., 1996). However, the 5'-UTLs from the cauliflower mosaic virus (CaMV) 35S transcript and the maize genes glutelin (Boronat et al., 1986), PEP-carboxylase (Hudspeth and Grula, 1989) and ribulose biphosphate carboxylase showed a considerable increase in expression of the luciferase gene in maize relative to its native leader (Koziel et al., 1996).

These 5'-UTLs had different effects in tobacco. In contrast to maize, the TMV Ω 5'-UTL and the AMV coat protein 5'-UTL enhanced expression in tobacco, whereas the glutelin, maize PEP-carboxylase and maize ribulose-1,5-bisphosphate carboxylase 5'-UTLs did not show enhancement relative to the native luciferase 5'-UTL (Koziel et al., 1996). Only the CaMV 35S 5'-UTL enhanced luciferase expression in both maize and tobacco (Koziel et al., 1996). Furthermore, the TMV and BMV coat protein 5'-UTLs were inhibitory in both maize and tobacco protoplasts (Koziel et al., 1996).

4.16.2 Use of Introns to Increase Expression

Including one or more introns in the transcribed portion of a gene has been found to increase heterologous gene expression in a variety of plant systems (Callis et al., 1987; Maas et al., 1991; Mascerenhas et al., 1990; McElroy et al., 1990; Vasil et al., 1989), although not all introns produce a stimulatory effect and the degree of stimulation varies. The enhancing effect of introns appears to be more apparent in monocots than in dicots. Tanaka et al., (1990) has shown that use of the catalase intron 1 isolated from castor beans increases gene expression in rice. Likewise, the first intron of the alcohol dehydrogenase 1 (Adh1) has been shown to increase expression of a genomic clone of Adh1 comprising the endogenous promoter in transformed maize cells (Callis et al., 1987; Dennis et al., 1984). Other introns that are also able to increase expression of transgenes which contain them include the introns 2 and 6 of Adh1 (Luehrsen and Walbot, 1991), the catalase intron (Tanaka et al., 1990), intron 1 of the maize bronze 1 gene (Callis et al., 1987), the maize sucrose synthase intron 1 (Vasil et al., 1989), intron 3 of the rice actin gene (Luehrsen and Walbot, 1991), rice actin intron 1 (McElroy et al., 1990), and the maize ubiquitin exon 1 (Christensen et al., 1992).

Generally, to achieve optimal expression, the selected intron(s) should be present in the 5' transcriptional unit in the correct orientation with respect to the splice junction sequences (Callis et al., 1987; Maas et al., 1991; Mascerenhas et al., 1990; Oard et al., 1989; Tanaka et al., 1990; Vasil et al., 1989). Intron 9 of Adh1 has been shown to increase expression of a heterologous gene when placed 3' (or downstream of) the gene of interest (Callis et al., 1987).

4.16.3 Use of Synthetic Genes to Increase Expression of Heterologous Genes in Plants When introducing a prokaryotic gene into a eukaryotic host, or when expressing a eukaryotic gene in a non-native host, the sequence of the gene must often be altered or modified to allow efficient translation of the transcript(s) derived form the gene. Significant experience in using synthetic genes to increase expression of a desired protein has been achieved in the expression of *B. thuringiensis* in plants. Native *B. thuringiensis* genes are often expressed only at low levels in dicots and sometimes not at all in many species of monocots (Koziel et al., 1996). Codon usage in the native genes is considerably different from that found in typical plant genes, which have a higher G+C content. Strategies to increase expression of these genes in plants generally alter the overall G+C content of the genes. For example, synthetic *B. thuringiensis* crystal-protein encoding genes have resulted in significant improvements in expression of these endotoxins in various crops including cotton (Perlak et al., 1990; Wilson et al., 1992), tomato (Perlak et al., 1991), potato (Perlak et al., 1993), rice (Cheng et al., 1998), and maize (Koziel et al., 1993).

In a similar fashion the inventors contemplate that the genetic constructs of the present invention, because they contain one or more genes of bacterial origin, may in certain circumstances be altered to increase the expression of these prokaryotic-derived genes in particular eukaryotic host cells and/or transgenic plants which comprise such constructs. Using molecular biology techniques which are well-known to those of skill in the art, one may alter the coding or non coding sequences of the particular Cry-encoding gene sequences to optimize or facilitate its expression in transformed plant cells at levels suitable for preventing or reducing insect infestation or attack in such transgenic plants.

4.16.4 Chloroplast Sequestering and Targeting

Another approach for increasing expression of A+T rich genes in plants has been demonstrated in tobacco chloroplast transformation. High levels of expression of an unmodified *B. thuringiensis* crystal protein-encoding genes in tobacco has been reported by McBride et al., (1995).

Additionally, methods of targeting proteins to the chloroplast have been developed. This technique, utilizing the pea chloroplast transit peptide, has been used to target the enzymes of the polyhydroxybutyrate synthesis pathway to the chloroplast (Nawrath et al., 1994). Also, this technique negated the necessity of modification of the coding region other than to add an appropriate targeting sequence.

U.S. Pat. No. 5,576,198 (specifically incorporated herein by reference) discloses compositions and methods useful for genetic engineering of plant cells to provide a method of controlling the timing or tissue pattern of expression of foreign DNA sequences inserted into the plant plastid genome. Constructs include those for nuclear transformation which provide for expression of a viral single subunit RNA polymerase in plant tissues, and targeting of the expressed polymerase protein into plant cell plastids. Also included are plastid expression constructs comprising a promoter region which is specific to the RNA polymerase expressed from the nuclear expression constructs described above and a heterologous gene of interest to be expressed in the transformed plastid cells. Alternatively, the gene can be transformed/localized to chloroplast/plastid genome and expressed from there using promoters well known in the art (see Maliga, et al.)

4.16.5 Effects of 3' Regions on Transgene Expression

The 3'-end regions of transgenes have been found to have a large effect on transgene expression in plants (Ingelbrecht et al., 1989). In this study, different 3' ends were operably linked to the neomycin phosphotransferase II (NptII) reporter gene and expressed in transgenic tobacco. The different 3' ends used were obtained from the octopine synthase gene, the 2S seed protein from *Arabidopsis*, the small subunit of rbcS from *Arabidopsis*, extension form carrot, and chalcone synthase from *Antirrhinum*. In stable tobacco transformants, there was about a 60-fold difference between the best-expressing construct (small subunit rbcS 3' end) and the lowest expressing construct (shalcone synthase 3' end).

TABLE 5

PLANT PROMOTERS

| Promoter | Reference[a] |
|---|---|
| Viral | |
| Figwort Mosaic Virus (FMV) | U.S. Pat. No. 5,378,619 |
| Cauliflower Mosaic Virus (CaMV) | U.S. Pat. No. 5,530,196 |
| | U.S. Pat. No. 5,097,025 |
| | U.S. Pat. No. 5,110,732 |
| Plant | |
| Elongation Factor | U.S. Pat. No. 5,177,011 |
| Tomato Polygalacturonase | U.S. Pat. No. 5,442,052 |
| *Arabidopsis* Histone H4 | U.S. Pat. No. 5,491,288 |
| Phaseolin | U.S. Pat. No. 5,504,200 |
| Group 2 | U.S. Pat. No. 5,608,144 |
| Ubiquitin | U.S. Pat. No. 5,614,399 |
| P119 | U.S. Pat. No. 5,633,440 |
| α-amylase | U.S. Pat. No. 5,712,112 |
| Viral enhancer/Plant promoter | |
| CaMV 35Senhancer/mannopine synthase promoter | U.S. Pat. No. 5,106,739 |

[a]Each reference is specifically incorporated herein by reference in its entirety.

TABLE 6

TISSUE SPECIFIC PLANT PROMOTERS

| Tissue Specific Promoter | Tissue(s) | Reference[a] |
|---|---|---|
| Blec | epidermis | U.S. Pat. No. 5,646,333 |
| malate synthase | seeds; seedlings | U.S. Pat. No. 5,689,040 |
| isocitrate lyase | seeds; seedlings | U.S. Pat. No. 5,689,040 |
| patatin | tuber | U.S. Pat. No. 5,436,393 |
| ZRP2 | root | U.S. Pat. No. 5,633,363 |
| ZRP2(2.0) | root | U.S. Pat. No. 5,633,363 |
| ZRP2(1.0) | root | U.S. Pat. No. 5,633,363 |
| RB7 | root | U.S. Pat. No. 5,459,252 |
| | root | U.S. Pat. No. 5,401,836 |
| | fruit | U.S. Pat. No. 4,943,674 |
| | meristem | U.S. Pat. No. 5,589,583 |
| | guard cell | U.S. Pat. No. 5,538,879 |
| | stamen | U.S. Pat. No. 5,589,610 |
| SodA1 | pollen; middle layer; stomium of anthers | Van Camp et al., 1996 |
| SodA2 | vasular bundles; stomata; axillary buds; pericycle; stomium; pollen | Van Camp et al., 1996 |
| CHS15 | flowers; root tips | Faktor et al., 1996 |
| Psam-1 | phloem tissue; cortex; root tips | Vander et al., 1996 |
| ACT11 | elongating tissues and organs; pollen; ovules | Huang et al., 1997 |
| zmGBS | pollen; endosperm | Russell and Fromm, 1997 |
| zmZ27 | endosperm | Russell and Fromm, 1997 |
| osAGP | endosperm | Russell and Fromm, 1997 |
| osGT1 | endosperm | Russell and Fromm, 1997 |
| RolC | phloem tissue; bundle sheath; vascular parenchyma | Graham et al., 1997 |
| Sh | phloem tissue | Graham et al., 1997 |
| CMd | endosperm | Grosset et al., 1997 |
| Bnm1 | pollen | Treacy et al., 1997 |
| rice tungro bacilliform virus | phloem | Yin et al., 1997a; 1997b |
| S2-RNase | pollen | Ficker et al., 1998 |
| LeB4 | seeds | Baumlein et al., 1991 |
| gf-2.8 | seeds; seedlings | Berna and Bernier, 1997 |

[a]Each reference is specifically incorporated herein by reference in its entirety.

The ability to express genes in a tissue specific manner in plants has led to the production of male and female sterile plants. Generally, the production of male sterile plants involves the use of anther-specific promoters operably linked to heterologous genes that disrupt pollen formation (U.S. Pat. Nos. 5,689,051; 5,689,049; 5,659,124, each specifically incorporated herein by reference). U.S. Pat. No. 5,633,441 (specifically incorporated herein by reference) discloses a method of producing plants with female genetic sterility. The method comprises the use of style-cell, stigma-cell, or style- and stigma-cell specific promoters that express polypeptides that, when produced in the cells of the plant, kills or significantly disturbs the metabolism, functioning or development of the cells.

TABLE 7

INDUCIBLE PLANT PROMOTERS

| Promoter | Reference[a] |
|---|---|
| heat shock promoter | U.S. Pat. No. 5,447,858 |
| Em | U.S. Pat. No. 5,139,954 |
| Adh1 | Kyozoka et al., 1991 |
| HMG2 | U.S. Pat. No. 5,689,056 |
| cinnamyl alcohol dehydrogenase | U.S. Pat. No. 5,633,439 |
| asparagine synthase | U.S. Pat. No. 5,595,896 |
| GST-II-27 | U.S. Pat. No. 5,589,614 |

[a]Each reference is specifically incorporated herein by reference in its entirety.

4.18 Antibody Compositions and Methods of Making

In particular embodiments, the inventors contemplate the use of antibodies, either monoclonal or polyclonal which bind to one or more of the polypeptides disclosed herein. Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified crystal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

4.19 Elisas and Immunoprecipitation

ELISAs may be used in conjunction with the invention. The production and use of ELISAs or kits emplyoying such ELISAs are well know to those of skill in the art.

4.20 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

4.21 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 8.

TABLE 8

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation of *B. thuringiensis* Strains EG4550 and EG5899

Crop dust samples were obtained from various sources throughout the United States and abroad, typically from grain-storage facilities. The crop dust samples were treated and spread on agar plates to isolate individual *Bacillus*-type colonies, e.g., *B. thuringiensis*, as described in U.S. Pat. No. 5,187,091, specifically incorporated herein by reference in its entirety. Phase-contrast microscopy was used to visually identify cells with crystalline inclusions in the colonies that grew after this treatment. Crystal-producing strains were then characterized by modified Eckhardt agarose gel electrophoresis as described by Gonzalez et al., (1982). This procedure allows the visualization of the array of native plasmids in a *B. thuringiensis* strain. The plasmid arrays can be compared to those of known serovars of *B. thuringiensis* to facilitate the identification of wild-type strains (Carlton and Gonzalez, 1985).

Strain EG4550 is a crystal-producing *B. thuringiensis* strain isolated from a New York crop dust sample. The crystalline inclusions of sporulated EG4550 have a distinct morphology and resemble tiny rods. The plasmid array of EG4550 does not resemble the array of any of the known serovars of *B. thuringiensis.*

Strain EG5899 is a crystal-producing *B. thuringiensis* strain isolated from a California crop dust sample. The crystalline inclusions of sporulated EG5899 are unusual in that they appear to be multiple attached crystals with an irregular morphology. The plasmid array of EG5899 does not resemble the array of any of the known serovars of *B. thuringiensis.*

Insect bioassay of the *B. thuringiensis* strains EG4550 and EG5899 indicated that these strains are toxic to larvae of coleopteran insects, including SCRW, suggesting that the crystals in these strains contained novel insecticidal proteins. EG4550 and EG5899 were deposited with the ARS Patent Culture Collection and been assigned NRRL numbers B-21784 and B-21783, respectively. These strains and other strains of the present invention are listed in Table 9:

TABLE 9

WILD-TYPE AND RECOMBINANT BACTERIAL STRAINS[a]

| Strain | NRRL Accession # | NRRL Deposit Date[b] | Organism | Plasmid | Cloned Insert | Vector | cry Gene(s) Present | Plasmid Antibiotic Marker |
|---|---|---|---|---|---|---|---|---|
| EG4550 | B-21784 | May 30, 1997 | *B. thuringiensis* | — | — | — | cryET39, 74, 75 | — |
| EG5899 | B-21783 | May 30, 1997 | *B. thuringiensis* | — | — | — | cryET39, 74, 75 | — |
| EG11582 | — | — | *E. coli* | pEG1337 | 8.4-kb HindIII | pUC18 | cryET39, 74, 75 | Amp |
| EG11525 | — | — | *E. coli* | pEG1321 | 8.4-kb HindIII | pEG597 | cryET39, 74, 75 | Amp |
| EG11529 | B-21917 | Feb. 12, 1998 | *B. thuringiensis* | pEG1321 | 8.4-kb HindIII | pEG597 | cryET39, 74, 75 | Cm |
| EG11521 | — | — | *E. coli* | pEG1319 | 8.4-kb HindIII | pBluescript | cryET39, 74, 75 | Amp |
| EG11934 | — | — | *B. thuringiensis* | pEG1918 | 4.5-kb HindIII | pHT315 | cryET75 | Eryth |
| EG11935 | — | — | *B. thuringiensis* | pEG1919 | 3.2-kb HindIII-EcoRI | pHT315 | cryET74 | Eryth |
| EG11936 | — | — | *B. thuringiensis* | pEG1920 | 3.7-kb HindIII | pHT315 | cryET39, 74 | Eryth |
| EG11937 | — | — | *B. thuringiensis* | pEG1921 | 1.4-kb HindIII | pEG1915 | cryET39 | Eryth |
| EG4100 | B-21786 | May 30, 1997 | *B. thuringiensis* | — | — | — | cryET69 | — |
| EG11647 | B-21787 | May 30, 1997 | *B. thuringiensis* | pEG1820 | MboI partial | pHT315 | cryET69 | Eryth |
| EG9444 | B-21785 | May 30, 1997 | *B. thuringiensis* | — | — | — | cryET71, 79 | — |
| EG11648 | B-21788 | May 30, 1997 | *B. thuringiensis* | pEG1821 | MboI partial | pHT315 | cryET71, 79 | Eryth |
| EG4851 | B-21915 | Feb. 12, 1998 | *B. thuringiensis* | — | — | — | cryET76, 80, 84 | — |
| EG11658 | B-21916 | Feb. 12, 1998 | *B. thuringiensis* | pEG1823 | MboI partial | pHT315 | cryET76, 80, 84 | Eryth |

[a]The details of the construction of the strains listed above are included in the following Examples.

[b]The subject cultures have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the finishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Cultures shown in Table 3 were deposited in the permanent collection of the Agricultural Research Service Culture Collection, Northern Regional Research Laboratory (NRRL), located at 1815 N. University Street, Peoria, Ill. 61604, under the terms of the Budapest Treaty.

5.2 Example 2

Evaluation of the Crystal Proteins of EG4550 and EG5899

Strains EG4550 and EG5899 were grown in C2 sporulation medium (Donovan, et al., *J. Biol. Chem*., 263:561-567, 1988) for three days at 30° C. during which the cultures grew to stationary phase, sporulated and lysed, releasing the protein inclusions into the medium. The cultures were centrifuged to harvest cell pellets containing the spores and crystals. The pellets were washed by suspension in a solution of 0.005% Triton X-100® and centrifuged. The washed pellets were resuspended at one-tenth the original volume in 0.005% Triton X-100®.

Crystal proteins were solubilized from the spores-crystals suspensions by incubating in solubilization buffer [0.14 M Tris-HCl pH 8.0, 2% (wt./vol.) sodium dodecyl sulfate (SDS), 5% (vol./vol.) 2-mercaptoethanol, 10% (vol./vol.) glycerol, and 1% bromphenol blue] at 100° C. for 5 min. The solubilized crystal proteins were size-fractionated by SDS-PAGE using a gel with an acrylamide concentration of 12.5%.

After size fractionation the proteins were visualized by staining with Coomassie Brilliant Blue R-250. Strain EG4550 displayed proteins with approximate molecular weights of 45 and 15 kDa. Strain EG5899 displayed proteins of approximate molecular weights of 160 kDa, 45 kDa, 35 kDa, and 15 kDa.

5.3 Example 3

Characterization of the CryET39 Crystal Protein of EG4550

The $NH_2$-terminal sequence of the approximately 45-kDa protein of EG4550, designated CryET39, was determined. A sporulated culture of EG4550 was washed and resuspended. The crystal proteins in the suspension were solubilized and run on a 10% acrylamide gel following the procedures for SDS-PAGE analysis. After electrophoresis the proteins were transferred to a BioRad PVDF membrane using standard western blotting procedures. Following transfer the membrane was rinsed 3× in distilled $H_2O$ and stained for 1 min using Amido Black 1013 (Sigma Chemical Co., St. Louis, Mo.). The filter was destained for 1 min in 5% acetic acid and then rinsed in 3 changes of distilled $H_2O$. The portion of the filter containing the approximately 45-kDa CryET39 band was excised with a razor blade. This procedure resulted in a pure form of CryET39 being obtained as a protein band blotted onto a PVDF membrane (BioRad, Hercules, Calif.).

The determination of the $NH_2$-terminal amino acid sequence of the purified CryET39 protein immobilized on the membrane was performed in the Department of Physiology at the Tufts Medical School, Boston, Mass. using standard Edman degradation procedures. The $NH_2$-terminal sequence was determined to be:

```
                                      (SEQ ID NO:20)
1   2   3   4   5   6   7   8   9   10  11  12  13  14  15
Met Leu Asp Thr Asn Lys Val Tyr Glu Ile Ser Asn His Ala Asn
```

Computer algorithms (Korn and Queen, 1984) were used to compare the $NH_2$-terminal sequence of the CryET39 protein with the amino acid sequences of all *B. thuringiensis* crystal proteins of which the inventors were aware including the sequences of all *B. thuringiensis* crystal proteins which had been published in scientific literature, international patent applications, or issued patents. A list of the crystal proteins whose sequences have been published and assigned a gene/protein designation is shown in Table 2.

5.4 Example 4

Isolation of a DNA Fragment Comprising the CryET39 Gene

In order to identify the gene encoding CryET39, an oligonucleotide probe specific for the $NH_2$-terminal amino acid sequence of the protein was designed. Using codons typically found in *B. thuringiensis* toxin genes an oligonucleotide of 41 nucleotides was synthesized by Integrated DNA Technologies, Inc. (Coralville, Iowa) and designated wd271. The sequence of wd271 is:

```
                                     (SEQ ID NO:21)
5'-ATGTTAGATACAAATAAAGTATATGAAATTTCAAATCATGC-3'
```

Radioactively labeled wd271 was then used as a probe in Southern hybridization experiments, as described below, to identify a restriction fragment containing the cryET39 gene. Total DNA was extracted from strains EG4550 and EG5899 by the following procedure. Vegetative cells were resuspended in a lysis buffer containing 50 mM glucose, 25 mM Tris-HCl (pH 8.0), 10 mM EDTA, and 4 mg/ml lysozyme. The suspension was incubated at 37° C. for one hour. Following incubation, the suspension was extracted once with an equal volume of phenol, then once with an equal volume of phenol:chloroform:isoamyl alcohol (25:24:1), and once with an equal volume of chloroform:isoamyl alcohol (24:1). The DNA was precipitated from the aqueous phase by the addition of one-tenth volume 3 M sodium acetate then two volumes 100% ethanol. The precipitated DNA was collected by centrifugation, washed with 70% ethanol and resuspended in $dH_2O$.

The extracted DNA was then digested, in separate reactions, with various restriction endonucleases, including EcoRI and HindIII, using conditions recommended by the manufacturer (Promega Corp., Madison, Wis.). The digested DNA was size-fractionated by electrophoresis through a 0.8% agarose gel in 1× TBE (0.089 M Tris-borate, 0.089 M boric acid, 0.002 M EDTA) overnight at 2 volts/cm of gel length. The fractionated DNA fragments were then transferred to a Millipore Immobilon-NC® nitrocellulose filter (Millipore Corp., Bedford, Mass.) according to the method of Southern (1975). The DNA fragments were fixed to the nitrocellulose by baking the filter at 80° C. in a vacuum oven.

Identification of the DNA fragment(s) containing the sequence encoding the $NH_2$-terminus of the CryET39 protein (see Example 3) was accomplished by using the oligonucleotide wd271 as a hybridization probe. To radioactively label the probe, 1 to 5 pmoles wd271 was added to a reaction containing [$\gamma$-$^{32}$P]ATP (3 µl of 3,000 Ci/mmole at 10 mCi/ml in a 20-µl reaction volume), a 10× reaction buffer (700 mM Tris-HCl (pH 7.8), 100 mM $MgCl_2$, 50 mM DTT), and 10 units T4 polynucleotide kinase (Promega Corp.). The reaction was incubated 20 min at 37° C. to allow the transfer of the radioactive phosphate to the 5'-end of the oligonucleotide, thus making it useful as a hybridization probe.

The labeled probe was then incubated with the nitrocellulose filter overnight at 45° C. in 3×SSC, 0.1% SDS, 10× Denhardt's reagent (0.2% BSA, 0.2% polyvinylpyrrolidone, 0.2% Ficoll®), 0.2 mg/ml heparin. Following incubation the filter was washed in several changes of 3×SSC, 0.1% SDS at 45° C. The filter was blotted dry and exposed to Kodak X-OMAT AR X-ray film (Eastman Kodak Company, Rochester, N.Y.) overnight at −70° C. with a DuPont Cronex Lightning Plus screen to obtain an autoradiogram.

Examination of the autoradiogram identified an approximately 2.5-kb wd271-hybridizing EcoRI fragment in DNA from strain EG4550. Strain EG5899 had an approximately 8.4-kb HindIII restriction fragment that specifically hybridized to the labeled wd271. This result indicated that both EG4550 and EG5899 contained related, or perhaps identical, copies of the cryET39 gene.

5.5 Example 5

Cloning of the CryET39 Gene

The first cloning study included the isolation of the 2.5-kb EcoRI fragment of EG4550 in order to express and characterize the CryET39 protein of EG4550. When this fragment was cloned and expressed in a *B. thuringiensis* recombinant strain, however, only the 15 kDa protein was produced, indicating that the 2.5-kb EcoRI fragment does not contain a complete and functional cryET39 gene. This result also indicated that the genes for the 15-kDa crystal protein and CryET39 were, however, in close proximity. The recombinant *B. thuringiensis* strain expressing the 15-kDa protein, designated EG11467, was not toxic to larvae of SCRW.

The approximately 8.4 kb HindIII restriction fragment containing the cryET39 gene from EG5899 was isolated from total genomic DNA as described in Section 5.4. The DNA was digested with HindIII and electrophoresed through a 0.8% agarose, 1× TBE gel, overnight at 2 volts/cm of gel length. The gel was stained with ethidium bromide so that the digested DNA could be visualized when exposed to long-wave UV light. Gel slices containing DNA fragments of approximately 8.0-9.0 kb were excised from the gel with a razor blade. The DNA fragments were then purified from the gel slice using the Geneclean® procedure (Bio 101, Vista, Calif.).

The isolated DNA fragments were ligated into the phagemid pBluescript® II SK+ (Stratagene, LaJolla, Calif.) to create a library in *E. coli* of size-selected HindIII restriction fragments. The phagemid DNA vector pBluescript® II SK+ can replicate at a high copy number in *E. coli* and carries the gene for resistance to the antibiotic ampicillin, which can be used as a selectable marker. The fragments were mixed with HindIII-digested pBluescript® II SK+ that had been treated with bacterial alkaline phosphatase (GibcoBRL, Gaithersburg, Md.) to remove the 5' phosphates from the digested plasmid to prevent re-ligation of the vector to itself. T4 ligase and a ligation buffer (Promega Corp.) were added to the reaction containing the digested phagemid and the size-selected HindIII fragments. These were incubated at room temperature for 1 hour to allow the insertion and ligation of the HindIII fragments into the pBluescript® II SK+ vector.

The ligation mixture was introduced into transformation-competent *E. coli* DH5α™ cells (GibcoBRL) following procedures described by the manufacturer. The transformed *E. coli* cells were plated on LB agar plates containing 50 μg/ml ampicillin and incubated overnight at 37° C. The growth of several hundred ampicillin-resistant colonies on each plate indicated the presence of the recombinant plasmid in the cells of each of those colonies.

To isolate the colonies harboring the cloned 8.4-kb HindIII fragment containing the cryET39 gene, colonies were first transferred to nitrocellulose filters. This was accomplished by placing a circular filter (Millipore HATF 085 25, Millipore Corp., Bedford, Mass.) directly on top of the LB-ampicillin agar plates containing the transformed colonies. When the filter was slowly peeled off of the plate the colonies stuck to the filter giving an exact replica of the pattern of colonies from the original plate. Enough cells from each colony were left on the plate that 5 to 6 hours of growth at 37° C. restored the colonies. The plates were then stored at 4° C. until needed. The nitrocellulose filters with the transferred colonies were then placed, colony-side up, on fresh LB-ampicillin agar plates and allowed to grow at 37° C. until the colonies reached an approximate diameter of 1 mm.

To release the DNA from the recombinant *E. coli* cells the nitrocellulose fiters were placed colony-side up on 2 sheets of Whatman 3MM Chromatography paper (Whatman International Ltd., Maidstone, England) soaked with 0.5 N NaOH, 1.5 M NaCl for 15 min. This treatment lysed the cells and denatured the released DNA allowing it to stick to the nitrocellulose filter. The filters were then neutralized by placing the filters, colony-side up, on 2 sheets of Whatman paper soaked with 1 M ammonium acetate, 0.02 M NaOH for 10 min. The filters were then rinsed in 3×SSC, air dried, and baked for 1 hour at 80° C. in a vacuum oven to prepare them for hybridization.

The $NH_2$-terminal oligonucleotide specific for the cryET39 gene, wd271, was labeled at the 5' end with $\gamma$-$^{32}P$ and T4 polynucleotide kinase as described above. The labeled probe was added to the filters in 3×SSC, 0.1% SDS, 10× Denhardt's reagent (0.2% BSA, 0.2% polyvinylpyrrolidone, 0.2% Ficoll®), 0.2 mg/ml heparin and incubated overnight at 40° C. These conditions were chosen to allow hybridization of the labeled oligonucleotide to related sequences present on the nitocellulose blots of the transformed *E. coli* colonies. Following incubation the filters were washed in several changes of 3×SSC, 0.1% SDS at 45° C. The filters were blottted dry and exposed to Kodak X-OMAT AR X-ray film (Eastman Kodak) overnight at −70° C. with a DuPont Cronex Lightning Plus screen.

Several colonies from this transformation hybridized to wd271. These colonies were identified by lining up the signals on the autoradiogram with the colonies on the original transformation plates. The isolated colonies were then grown in LB-ampicillin liquid medium from which the cells could be harvested and recombinant plasmid prepared by the standard alkaline-lysis miniprep procedure (Maniatis et al., 1982). The isolated plasmids were digested with the restriction enzyme HindIII which indicated that the cloned fragments of EG5899 DNA were of the expected size, i.e. 8.4-kb. HindIII-digested plasmid DNA from six of the hybridizing colonies was electrophoresed through an agarose gel and transferred to nitrocellulose as described above. The blot was then hybridized with the oligonucleotide wd271 that had been radioactively labeled at the 5' end with $\gamma$-$^{32}P$ and T4 polynucleotide kinase. The approximately 8.4-kb insert fragments from all six of the digested plasmids hybridized with wd271 confirming the presence of the cryET39 gene. One of the plasmids with the 8.4 kb insert containing the cryET39 gene was designated pEG1319. The *E. coli* strain containing pEG1319 has been designated EG11521.

5.6 Example 6

Expression of Recombinant Proteins from EG11529

To characterize the properties of the CryET39 protein it was necessary to express the cloned cryET39 gene in *B. thuringiensis* cells that do not produce any crystal proteins ($Cry^-$). To accomplish this, the cloned 8.4-kb HindIII fragment from pEG1319 was inserted into a plasmid capable of replicating in *B. thuringiensis*, thus allowing the expression of the cryET39 gene and production of the encoded protein.

pEG1319 was digested with HindIII to excise the cloned 8.4-kb fragment. The digested plasmid was resolved on an agarose gel and a slice of the gel containing the 8.4-kb fragment was excised. The 8.4-kb Hind III fragment was purified from the gel slice using the GeneClean procedure (Bio101). The fragment was ligated into a *B. thuringiensis*/*E. coli* shuttle vector that had been digested with HindIII and treated with bacterial alkaline phosphatase. This shuttle vector, designated pEG597, was described by Baum et al., (1990). pEG597 is capable of replication in both *E. coli* and *B. thuringiensis*, conferring ampicillin resistance to *E. coli* and chloramphenicol resistance to *B. thuringiensis*. The ligation mixture was introduced into *E. coli* DH5α™ cells using transformation procedures described by the manufacturer (GibcoBRL). Plasmid DNA was prepared from $Amp^R$ transformants and restriction enzyme analysis was performed to confirm the proper construction. A plasmid containing the 8.4-kb HindIII fragment inserted into the pEG597 vector was designated pEG1321. The *E. coli* strain harboring pEG1321 was designated EG11525.

pEG1321 was introduced into a $Cry^-$ *B. thuringiensis* strain, EG10368, by electroporation (Macaluso and Mettus, 1991). Cells transformed to chloramphenicol resistance were selected by incubation overnight on LB agar plates containing 3 μg/ml chloramphenicol. Plasmid DNA was isolated from several of the *B. thuringiensis* transformants. The isolated plasmid was digested with HindIII and electrophoresed through an agarose gel. All of the transformants had restriction fragments corresponding to the 8.4 kb cryET39 fragment and the pEG597 vector. To verify the correct plasmid construction the restriction fragments were blotted to a nitrocellulose filter which was then hybridized with the cryET39-specific oligo wd271, as described above. The wd271 probe hybridized to the cloned 8.4 kb HindIII fragments confirming that pEG1321 contains the cryET39 gene and that it had been successfully introduced into *B. thuringiensis*. The *B. thuringiensis* recombinant strain containing pEG1321 was designated EG11529. EG11529 was deposited with the NRRL and given the accession number B-21917.

EG11529 was grown in DSM+glucose sporulation medium containing 5 μg/ml chloramphenicol [0.8% (wt./vol.) Difco nutrient broth, 0.5% (wt./vol.) glucose, 10 mM $K_2HPO_4$, 10 mM $KH_2PO_4$, 1 mM $Ca(NO_3)_2$, 0.5 mM $MgSO_4$, 10 μM $MnCl_2$, 10 μM $FeSO_4$] for three days at 30° C. during which the culture grew to stationary phase, sporulated and lysed, thus releasing the protein inclusions into the medium. The cultures were harvested by centrifugation. The pellet consisting of spores and protein crystals was washed in a solution of 0.005% Triton X-100®, 2 mM EDTA and centrifuged. The washed pellet was suspended at one-tenth the original volume in 0.005% Triton X-100®, 2 mM EDTA.

Crystal proteins were solubilized from the spores-crystal suspension by incubating the suspension in solubilization buffer [0.14 M Tris-HCl pH 8.0, 2% (wt./vol.) sodium dodecyl sulfate (SDS), 5% (vol./vol.) 2-mercaptoethanol, 10% (vol./vol.) glycerol, and 0.1% bromphenol blue] at 100° C. for 5 min. The solubilized crystal proteins were size-fractionated by SDS-PAGE. After size fractionation the proteins were visualized by staining with Coomassie Brilliant Blue R-250. This analysis showed that three distinct crystal proteins were produced in strain EG11529. In addition to the 44-kDa CryET39 toxin, approximately 15- and 35-kDa polypeptides were also produced.

The 35-kDa crystal protein expressed in *B. thuringiensis* EG11529 could be separated from the 44-kDa (CryET39) and 15-kDa proteins by centrifugation through a sucrose step gradient (steps: 55%, 68%, 72%, 79%) as described in Section 5.12. Determination of the $NH_2$-terminal amino acid sequence of the isolated 35-kDa protein was accomplished using procedures described in Section 5.3. The $NH_2$-terminal amino acid sequence of the 35-kDa protein was shown to be:

```
SILNLQDLSQKYMTAALNKI        (SEQ ID NO:22)
```

Comparison of the $NH_2$-terminus of the 35-kDa protein with the deduced amino acid sequence of CryET39 confirmed that it was not a processed form of the CryET39 protein. The approximately 35 kDa protein was designated CryET75, and the gene encoding it (which resides on the 8.4-kb fragment from EG5899) was designated cryET75.

The sucrose gradient fraction containing CryET39 also contained the approximately 15-kDa protein, designated CryET74. The $NH_2$-terminal amino acid sequence of CryET74 was determined as described for CryET39 in Section 5.3. The $NH_2$-terminal amino acid sequence of the isolated CryET74 protein was determined to be:

```
SARQVHIQINNKTRH         (SEQ ID NO:23)
```

Comparison of this sequence with that of CryET39 and CryET75 showed that CryET74 was a unique protein encoded by a third gene, designated cryET74, that was contained on the 8.4-kb HindIII fragment cloned from EG5899.

5.7 Example 7

Sequencing of the Cry Genes and Determination of the Amino Acids Sequences of the Encoded Polypeptides To facilitate the sequencing of the cryET39, cryET74, and cryET75 genes, the 8.4-kb HindIII fragment of pEG1319 was subcloned into HindIII-digested pUC18 (Yanisch-Perron et al., 1985). This plasmid was designated pEG1337, and is shown in FIG. 1.

Preparation of pEG1337 double-stranded plasmid template DNA was accomplished using either a standard alkaline lysis procedure or a Qiagen Plasmid Kit (Qiagen Inc., Chatworth, Calif.) following the manufacturer's procedures. The sequencing reactions were performed using the Sequenase™ Version 2.0 DNA Sequencing Kit (United States Biochemical/Amersham Life Science Inc., Cleveland, Ohio) following the manufacturer's procedures and using $^{35}S$-[dATP] as the labeling isotope (DuPont NEN Research Products, Boston, Mass.). Denaturing gel electrophoresis of the reactions was performed on a 6% (wt./vol.) acrylamide, 42% (wt./vol.) urea sequencing gel. The dried gel was exposed to Kodak X-OMAT AR X-ray film (Eastman Kodak) overnight at room temperature.

The $NH_2$-terminal specific oligonucleotide wd271 was used as the initial sequencing primer. The entire sequence for the cryET39 gene was determined using the procedures described above. Successive oligonucleotides to be used for priming sequencing reactions were designed from the sequencing data of the previous set of reactions. In this way the DNA sequencing progressed along both the top and bottom strand of the cryET39 gene in a step-wise fashion.

An oligonucleotide primer based on the $NH_2$-terminal amino acid sequence of the CryET75 protein was designed for use in sequencing the cryET75 gene. The oligonucleotide was designated MR51 and had the sequence:

```
5'-TCACAAAAATATATGAACAGC-3'   (SEQ ID NO:24)
```

Using the DNA sequencing procedures described above, a partial nucleotide sequence of the cryET75 gene was determined, with the completion of the sequence being achieved using automated sequencing. DNA samples were sequenced using the ABI PRISM® DyeDeoxy sequencing chemistry (Applied Biosystems, Inc., CA) according to the manufacturer's protocol. The completed reactions were run on an ABI 377 automated DNA sequencer. DNA sequence data were analyzed using Sequencher v3.0 DNA analysis software (Gene Codes Corporation, Ann Arbor, Mich.). The amino acid sequence of the CryET75 protein was then derived by translating the open reading frame of cryET75. The determined $NH_2$-terminal sequence of CryET75 was identical with the $NH_2$-terminal amino acid sequence derived from the nucleotide sequence.

Studies in which the 8.4-kb HindIII fragment from EG11529 was further digested and the fragments sub-cloned to express the crystal protein genes individually, or in combination, are described in Section 5.11. The expression of the CryET39 protein was dependent on cloning the cryET74 gene on the same restriction fragment. This suggested that the cryET74 gene was located upstream of the cryET39 gene and that the promoter for cryET74 also directs the expression of cryET39. Oligonucleotides specific for the DNA sequence 5' to the beginning of the cryET39 gene were designed for use as primers for automated sequencing. Successive primers were designed based on the data derived from each set of sequencing reactions. In this way the region upstream of cryET39 was sequenced in a step-wise fashion. A translation of the DNA sequence revealed an open reading frame encoding the CryET74 protein. Examination of the derived amino acid sequence found a region identical to the determined $NH_2$-terminal amino acid sequence of CryET74, identifying the open reading frame as the cryET74 gene.

5.7.1 CryET39

The DNA sequence of the CryET39 gene is represented by SEQ ID NO:7, and encodes the amino acid sequence of the CryET39 polypeptide, represented by SEQ ID NO:8.

5.7.1.3 Characteristics of the CryET39 Polypeptide Isolated from EG5899

The CryET39 polypeptide comprises a 385-amino acid sequence, has a calculated molecular mass of 44,246 Da, and has a calculated isoelectric constant (pI) equal to 5.47. The amino acid composition of the CryET39 polypeptide is given in Table 11.

TABLE 11

AMINO ACID COMPOSITION OF CRYET39

| Amino Acid | # Residues | % Total |
|---|---|---|
| Ala | 6 | 1.5 |
| Arg | 3 | 0.7 |
| Asn | 31 | 8.0 |
| Asp | 23 | 5.9 |
| Cys | 2 | 0.5 |
| Gln | 17 | 4.4 |
| Glu | 27 | 7.0 |
| Gly | 19 | 4.9 |
| His | 8 | 2.0 |
| Ile | 32 | 8.3 |
| Leu | 33 | 8.5 |
| Lys | 39 | 10.1 |
| Met | 8 | 2.0 |
| Phe | 6 | 1.5 |
| Pro | 16 | 4.1 |
| Ser | 30 | 7.7 |
| Thr | 36 | 9.3 |
| Trp | 7 | 1.8 |
| Tyr | 24 | 6.2 |
| Val | 18 | 4.6 |
| Acidic (Asp + Glu) | 50 | |
| Basic (Arg + Lys) | 42 | |
| Aromatic (Phe + Trp + Tyr) | 37 | |
| Hydrophobic (Aromatic + Ile + Leu + Met + Val) | 126 | |

5.7.2 CryET74

The DNA sequence of the CryET74 gene is represented by SEQ ID NO:5, and encodes the amino acid sequence of the CryET74 polypeptide, represented by SEQ ID NO:6.

5.7.2.3 Characteristics of the CryET74 Polypeptide

The CryET74 polypeptide comprises a 119-amino acid sequence, has a calculated molecular mass of 13,221 Da, and has a calculated pI equal to 6.21. The amino acid composition of the CryET74 polypeptide is given in Table 12.

TABLE 12

AMINO ACID COMPOSITION OF CRYET74

| Amino Acid | # Residues | % Total |
|---|---|---|
| Ala | 4 | 3.3 |
| Arg | 6 | 5.0 |
| Asn | 6 | 5.0 |
| Asp | 7 | 5.8 |
| Cys | 1 | 0.8 |
| Gln | 3 | 2.5 |
| Glu | 8 | 6.7 |
| Gly | 10 | 8.4 |
| His | 5 | 4.2 |
| Ile | 9 | 7.5 |
| Leu | 6 | 5.0 |
| Lys | 7 | 5.8 |
| Met | 2 | 1.6 |
| Phe | 4 | 3.3 |
| Pro | 3 | 2.5 |
| Ser | 13 | 10.9 |
| Thr | 12 | 10.0 |
| Trp | 1 | 0.8 |
| Tyr | 4 | 3.3 |
| Val | 8 | 6.7 |
| Acidic (Asp + Glu) | 15 | |
| Basic (Arg + Lys) | 13 | |
| Aromatic (Phe + Trp + Tyr) | 9 | |
| Hydrophobic (Aromatic + Ile + Leu + Met + Val) | 34 | |

5.7.3 CryET75

The DNA sequence of the CryET75 gene is represented by SEQ ID NO:15, and encodes the amino acid sequence of the CryET75 polypeptide, represented by SEQ ID NO:16.

5.7.3.3 Characteristics of the CryET75 Polypeptide

The CryET75 polypeptide comprises a 310-amino acid sequence, has a calculated molecular mass of 34,259 Da, and has a calculated pI equal to 5.67. The amino acid composition of the CryET75 polypeptide is given in Table 13.

TABLE 13

AMINO ACID COMPOSITION OF CRYET75

| Amino Acid | # Residues | % Total |
|---|---|---|
| Ala | 15 | 4.8 |
| Arg | 5 | 1.6 |
| Asn | 15 | 4.8 |
| Asp | 17 | 5.4 |
| Cys | 2 | 0.6 |
| Gln | 11 | 3.5 |
| Glu | 22 | 7.0 |
| Gly | 17 | 5.4 |
| His | 6 | 1.9 |
| Ile | 22 | 7.0 |
| Leu | 24 | 7.7 |
| Lys | 29 | 9.3 |
| Met | 7 | 2.2 |
| Phe | 11 | 3.5 |
| Pro | 9 | 2.9 |
| Ser | 34 | 10.9 |
| Thr | 33 | 10.6 |
| Trp | 1 | 0.3 |
| Tyr | 11 | 3.5 |
| Val | 19 | 6.1 |
| Acidic (Asp + Glu) | 39 | |
| Basic (Arg + Lys) | 34 | |
| Aromatic (Phe + Trp + Tyr) | 23 | |
| Hydrophobic (Aromatic + Ile + Leu + Met + Val) | 95 | |

5.8 Example 8

Homology Analyses for CryET39

The deduced amino acid sequence of the CryET39 protein was used to query electronic sequence databases for related protein homologies. The SWISS-PROT ALL (swall) database was queried using FASTA version 3.15 (Pearson and Lipman, 1988) on the FASTA server at the European Bioinformatics Institute under the following parameters (matrix =pam150, ktup=2, gapcost=−12, gapxcost=−2). The results of the database search showed that CryET39 exhibited ~25% amino acid sequence identity over a 322-amino acid region of the 42-kDa mosquitocidal crystal protein from *B. sphaericus*. CryET39 also showed ~20% sequence identity over a 343 amino acid region of the 51-kDa crystal protein from *B. sphaericus*. No other protein sequences in the database showed any significant sequence similarity with the CryET39 sequence. The amino acid sequence of CryET39 was also used to query the non-redundant (nr) database of the National Center Biotechnology Information (NCBI) using BLASTP version 2.0 (Altschul et al., 1997) using the following parameters: matrix=blosum62, gapped alignment, other parameters =default settings. The nr database comprises sequence entries from PDB, SWISS-PROT, PIR, and CDS translations of GenBank. The results of this search were in agreement with those obtained using the FASTA search.

5.9 Example 9

Database Searches for CryET74-Related Proteins

The deduced amino acid sequence for CryET74 was also used to query the SWISS-PROT ALL and nr databases using FASTA and BLASTP as described in Section 5.8. No proteins were found showing any significant sequence similarity to CryET74.

5.10 Example 10

Database Searches for CryET75-Related Proteins

The deduced amino acid sequence for CryET75 was also used to query the SWISS-PROT ALL and nr databases using FASTA and BLASTP as described in Section 5.8. The FASTA search revealed that CryET75 showed a 28.1% sequence identity with Cry15Aa (Genbank Accession Number M76442) over a 121-amino acid region. The BLASTP analysis revealed 23% sequence identity over a 231-amino acid region.

5.11 Example 11

Subcloning and Expression of the CryET39 and CryET74 Genes

The sucrose gradient fraction of parasporal crystals obtained from lysed cultures of strain EG11529 contained both CryET39 and CryET74 polypeptides. Bioassay evaluation of the CryET39 and CryET74 preparation demonstrated that this preparation was as toxic to WCRW larvae as total crystal protein prepared from EG11529. To determine the insecticidal activity of the CryET39 protein alone it was necessary to clone the cryET39 gene downstream from another promoter. As described below, this was accomplished by using the PCR™, to amplify the promoter region for the *B. thuringiensis* crystal protein, Cry2Ac (Wu et al., 1991) and placing it upstream of a PCR™-amplified cryET39 gene in a shuttle vector, thus allowing for the expression of only the CryET39 protein in a recombinant *B. thuringiensis* strain.

Oligonucleotides were designed for use as primers in the PCR™ amplification and subsequent cloning of the regulatory region of the cry2Ac gene; including the open reading frames ORF1 and ORF2, the ribosome binding site, and the start codon for Cry2Ac. Oligo mr47 includes the EcoRI restriction site 2124 base pairs upstream from the start codon of the cry2Ac coding region. The sequence of mr47 is:

```
                              (SEQ ID NO:25)
5'-ATATCTATAGAATTCGCAATTCGTCCATGTG-3'
            EcoRI
```

The complementary oligonucleotide primer, mr43, consists of the inverted complementary sequence for the ribosome binding site and start codon (Met) for the cry2Ac gene. A HindIII site has been incorporated between the RBS and the Met codon to allow for an in frame insertion of the sequence of the cryET39 gene. The sequence of mr43 is:

```
5'-CAGTATTCATATAAGCTTCCTCCTTTAATA-3' (SEQ ID NO:26)
        Met   HindIII RBS
```

The PCR™ reaction to amplify the cryET39 gene consisted of the following: four deoxynucleosidetriphosphates-dATP, dTTP, dCTP, dGTP- at a final concentration of 200 μM; 5 μl 10× Taq Extender™ Buffer (Stratagene Cloning Systems) for a final concentration of 1×; 10 ng pEG1273, which consisted of pUC18 into which the cry2Ac gene has been cloned; the oligonucleotide primers mr47 and mr43 at a final concentration of 2.5 μM each; 2.5 units Taq Extender™ (Stratagene Cloning Systems); 2.5 units Taq Polymerase (Promega Corp.); and $dH_2O$ to a final reaction volume of 50 μl. The reaction was performed in a PowerBlock™ EasyCycler™ Series temperature cycler (Ericomp, Inc., San Diego, Calif.). Cycling conditions consisted of a 2-min denaturation step at 94° C., followed by 30 cycles of 94° C. for 1 min, annealing at 50° C. for 1 min, and extension at 72° C. for 2 min. Following the cycling 5 μl of the reaction was electrophoresed through a 0.8% agarose gel to verify that an approximately 2-kb product band was produced by the PCR™. The remainder of the reaction product was purified using a QIAquick™ spin column following the manufacturer's instructions (QIAGEN, Inc.).

The PCR™-amplified cry2Ac promoter was then cloned into the *E. coli/B. thuringiensis* shuttle vector pHT315 (Arantes and Lereclus, 1991). This was accomplished by digesting both pHT315 and the PCR™ product, in separate reactions, with the restriction enzymes EcoRI and HindIII. These enzymes cut within the multiple cloning region of pHT315 and near the ends of the PCR™ product, within the sequences specified by the oligonucleotides mr47 and mr43. The digested PCR™ product was isolated by running the reaction through an agarose gel, followed by purification of the approximately 2-kb fragment using the Geneclean™ procedure (Bio 101). Digested pHT315 was purified in a similar manner. The fragment was then ligated into the digested pHT315 in a reaction containing T4 DNA ligase and a ligation buffer (Promega Corp.).

The ligation mixture was introduced into transformation-competent *E. coli* DH5α™ cells (GibcoBRL) following procedures described by the manufacturer. The *E. coli* cells were plated on LB agar plates containing 50 μg/ml ampicillin and incubated overnight at 37° C. pHT315 contains a gene that confers ampicillin resistance to recombinant cells into which it has been successfully introduced. Plasmid DNA was prepared from several ampicillin-resistant clones and digested with EcoRI and HindIII to confirm the presence of the 2-kb insert. One of these plasmids, designated pEG1915, was used for the cloning and expression of the cryET39 gene.

PCR™ was used to amplify cryET39 from the cloned 8.4-kb HindIII fragment in pEG1337. Oligonucleotide primers were designed to facilitate the insertion of cryET39 into pEG1915 so that the gene could be expressed from the cry2Ac promoter. The cryET39-specific oligonucleotide, mr44, includes the start codon (Met) for cryET39 with a HindIII site engineered 5' to the start codon. The sequence of mr44 is:

```
                                         (SEQ ID NO:27)
5'-AAGGTGAAGCTTTTATGTTAGATACTAATAAAGTTTATG-3'
         HindIII Met
```

A second primer, designated mr45, was designed to be complementary to a sequence 212 base pairs 3' to the end of the cryET39 coding region. A HindIII site was incorporated into the sequence of mr45.

```
5'-CCGGAATAGAAGCTTTGCATATGG-3'      (SEQ ID NO:28)
           HindIII
```

The cryET39 PCR™ product generated using mr44 and mr45 as a primers was cut with HindIII and inserted into the HindIII site specified by mr43 in the plasmid pEG1915. This places the Met codon of the cryET39 gene 7-base pairs downstream from the ribosome binding site of the cloned cry2Ac promoter. Such a configuration was expected to allow the efficient expression of the recombinant CryET39 protein. The ligation reaction that was performed to insert the cryET39 gene into pEG1915 was used to transform *E. coli* DH5α™ to ampicillin resistance. Plasmid DNA was prepared and subjected to restriction enzyme analysis to identify a clone in which the cryET39 gene had inserted into pEG1915 in the proper orientation. It was necessary for the sense strand of cryET39 to be oriented in the same direction as that of the cry2Ac regulatory region for efficient transcription to occur. Restriction digests using the enzymes shown in FIG. 2 identified a plasmid containing cryET39 in the proper orientation. This plasmid was designated pEG1921.

A Cry⁻ strain of *B. thuringiensis* was transformed to erythromycin resistance by the introduction of pEG1921. This recombinant strain, designated EG11937, was grown in C2 sporulation medium until sporulation and crystal formation had occurred. Phase contrast microscopy clearly identified crystalline inclusions in the shape of elongated rectangles, or needles, in the culture. The spores, crystals, and unlysed sporangia were harvested by centrifugation. The material in the pellet was washed twice in a solution of 0.005% Triton X-100®, 10 mM Tris-HCl pH7.5 and suspended at one-half the original volume in the wash solution.

SDS-PAGE was used to visualize the protein in the crystal. 25 μl of 0.5 N NaOH was added to 100 μl of the sample to inhibit proteolytic activity which can destroy the protein as the crystal is solubilized. After 2.5 min at room temperature 65 μL of 3× Laemmli sample buffer (30% glycerol, 15% 2-mercaptoethanol, 3% SDS, 0.1875 M Tris, 0.01% bromphenol blue) was added to the sample. The sample was heated to 100° C. for 5 min, centrifuged briefly to remove insoluble material, and loaded onto an acrylamide gel. The protein bands were visualized by staining with Coomassie Brilliant Blue R-250. This analysis demonstrated that EG11937 expressed the 44-kDa CryET39 protein and not the 13-kDa (CryET74) or 34-kDa (CryET75) proteins produced by recombinant strain, EG11529. The PCR™-generated copy of the cryET39 gene in pEG1921 was sequenced to confirm that it was identical to the wild-type copy from pEG1337. Strain EG11937 was grown and prepared for bioassays on WCRW larvae. Unexpectedly the crystal protein from EG11937 had no activity on the insects. This result suggested that either the CryET39 protein requires the presence of the CryET74 to be toxic, or that CryET74 is the active toxin protein.

pEG1337 was digested with the restriction enzymes HindIII and EcoRI to release an approximately 3.2-kb fragment containing the cryET74 gene and only a small piece of the cryET39 gene. This fragment was isolated on an agarose gel, purified, and cloned into the shuttle vector pHT315, digested with HindIII and EcoRI, using procedures described above. This plasmid, designated pEG1919, was introduced into the Cry⁻ *B. thuringiensis* strain, EG10650, by electroporation, transforming the recombinant cells to erythromycin resistance. One transformant, designated EG11935, was grown in C2 sporulation medium to determine if the cloned cryET74 gene could direct the expression of the crystal protein. The culture was harvested and the crystal protein analyzed by SDS-PAGE as described above. EG11935 produced only CryET74 and had no activity on larvae of the WCRW.

The observations that CryET39 and CryET74, individually, have no activity on WCRW larvae indicates that the two proteins interact to form a toxic protein composition. PCR™ was used to generate a DNA fragment containing the genes for CryET39 and CryET74, but not the gene for CryET75 also present on the 8.4-kb fragment of pEG1337 (see map of pEG1337). The m13/pUC forward sequencing primer, (GibcoBRL), and mr45 were used to amplify an approximately 3.7-kb product containing both cryET74 and cryET39. PCR™ was performed using conditions described above using pEG1337 as the template. The PCR™ product was gel purified, digested with HindIII, and cloned into pHT315 that had been cut with HindIII and treated with bacterial alkaline phosphatase. The resulting plasmid, designated pEG1920, was used to transform the Cry⁻ *B. thuringiensis* strain, EG10650, to erythromycin resistance. One recombinant, designated EG11936, was grown to assess crystal protein production. EG11936 produced both the 44-kDa CryET39 and the approximately 13-kDa CryET74 polypeptides. Crystal proteins produced by EG11936 had activity on WCRW larvae comparable to the activity seen with the recombinant strain, EG11529.

5.12 Example 12

Toxicity of Crystal Proteins to Insects

5.12.1 Toxicity of EG11529 Crystal Proteins to SCRW Larvae

The toxicity to SCRW larvae (*Diabrotica undecimpunctata howardi*) was determined for the recombinant strain EG11529, that expressed CryET39, CryET74, and CryET75 polypeptides.

EG11529 was grown in C2 medium at 30° C. for 3 days until sporulation and lysis had occurred. The cultures were harvested by centrifigation, washed twice in 1× original volume 0.005% Triton X-100®, and suspended in 1/10 the original culture volume of 0.005% Triton X-100®. For comparison EG11535, a recombinant *B. thuringiensis* strain expressing the coleopteran-toxic protein Cry3B2 (Donovan et al., 1992) was grown and harvested in the same manner.

SDS-PAGE was used to visualize the proteins. The proteins were quantified by comparison with standard loading of a known amount of bovine serum albumin (Sigma Chemical Co., St. Louis, Mo.) using a Computing Densitometer, Model 300A, (Molecular Dynamics, Sunnyvale, Calif.), following the manufacturer's procedures.

SCRW larvae were bioassayed via surface contamination of an artificial diet similar to Marrone et al., (1992), but without formalin. Each bioassay consisted of eight serial aqueous dilutions with aliquots applied to the surface of the diet. After the diluent (an aqueous 0.005% Triton X-100® solution) had dried, first instar larvae were placed on the diet and incubated at 28° C. Thirty-two larvae were tested per dose. Mortality was scored after 7 days. Data from replicated bioassays were pooled for probit analysis (Daum, 1970) with mortality being corrected for control death, the control being diluent only (Abbot, 1925). Results were reported as the amount of crystal protein per well (175 $mm^2$ of diet surface) resulting in an $LC_{50}$, the concentration killing 50% of the test insects. 95% confidence intervals were also reported.

TABLE 14

INSECTICIDAL ACTIVITY OF EG11529 PROTEINS ON SCRW LARVAE

| Sample | $LC_{50}$ (μg protein/well) | 95% C.I. |
|---|---|---|
| EG11529 | 34.1 | 28-41 |
| EG11535 (Cry3B2) | 49.5 | 33-83 |

The results shown in the above table demonstrated that the crystal proteins of EG11529 had significant activity on larvae of the SCRW. The $LC_{50}$ value for EG11529 was lower than that seen for the Cry3B2 control protein, although the 95% confidence intervals did overlap, indicating the difference may not have been significant.

5.12.2 Toxicity of CryET39 and CryET74 to WCRW Larvae

The toxicity to WCRW larvae (*Diabrotica virgifera virgifera*) was determined for EG11529, as well as the recombinant strains constructed to produce the individual crystal proteins of EG11529. The recombinant strains and the crystal proteins they produced are shown in Table 15.

TABLE 15

| Bt Recombinant Strain | Crystal Protein Expressed | MW (kDa)* |
|---|---|---|
| EG11529 | CryET39 | 44 kDa |
| | CryET74 | 13 kDa |
| | CryET75 | 34 kDa |
| EG11934 | CryET75 | 34 kDa |
| EG11935 | CryET74 | 13 kDa |
| EG11936 | CryET39 + CryET74 | 44 kDa + 13 kDa |
| EG11937 | CryET39 | 44 kDa |

*Molecular weights are estimated by migration of the protein on an SDS-PAGE gel and comparison with standards of known molecular weight.

A series of bioassays to determine the activity of the crystal proteins was performed essentially as described for the SCRW assays, with the exception that neonate larvae were used instead of first instar larvae. Purified crystal proteins were prepared for the first assay using sucrose step gradients. EG11529 was grown for three days at 30° C. in C2 sporulation medium. The sporulated and lysed cultures were harvested by centrifugation and washed, twice, in equal volumes of wash buffer (10 mM Tris-HCl, pH 7.5, 0.005% Triton X-100®), and suspended at $1/10^{th}$ the original volume in the wash solution. Sucrose step gradients were prepared by layering solutions of decreasing concentrations of sucrose, in the wash solution, in 25×89 mm Ultra-Clear centrifuge tubes (Beckman Instruments, Inc., Palo Alto, Calif.). The steps consisted of 7.5 ml each of the following concentrations of sucrose (bottom to top): 79%-72%-68%-55%. 5 ml of the spore/crystal suspension were layered on top of the gradient. The gradients were centrifuged at 18,000 rpm at 4° C. in an L8-70M ultracentrifuge (Beckman Instruments) overnight. The crystal proteins of EG11529 separated into two distinct bands. One band, at the 68%-72% interface, contained only the CryET75 protein. The second band, at the 72%-79% interface, contained both CryET39 and CryET74. The bands were pulled off with a pipet and washed, twice, in the wash buffer. The protein sample was then run over a second gradient to assure a complete separation of CryET75 from CryET39 and CryET74. The protein samples were run on an SDS-PAGE gel to verify the sample integrity. The samples were then quantified using a standard protein assay (Bio-Rad Laboratories, Hercules, Calif.), following manufacturer's procedures.

An assay was performed comparing the toxicity to WCRW larvae of the CryET39+CryET74 and the CryET75 purified crystal protein samples with the toxicity of EG11529. EG11529 was prepared as a spore/crystal suspension and the amount of protein was determined by SDS-PAGE and densitometry. Data from the assay were pooled for probit analysis (Daum, 1970) with mortality being corrected for control death, the control being diluent only (Abbot, 1925). Results are reported as the amount of crystal protein per well (175 $mm^2$ of diet surface) resulting in an $LC_{50}$, the concentration killing 50% of the test insects. 95% confidence intervals were also reported in Table 16.

TABLE 16

INSECTICIDAL ACTIVITY OF EG11529 PROTEINS ON WCRW LARVAE

| Sample | $LC_{50}$ (μg/well) | 95% C.I. |
|---|---|---|
| CryET75 | No Activity* | |
| EG11529 | 8.6 | 6.6-10.6 |
| CryET39 + CryET74 | 9.7 | 7.2-12.7 |

*6% mortality at a dose of 45 μg/well

This assay clearly demonstrated that the purified CryET75 protein was not toxic towards the larvae of the WCRW. The sample containing the mixture of CryET39 and CryET74 had activity similar to that of EG11529, indicating that the CryET75 played no synergistic role in the toxicity of EG11529 to WCRW larvae.

To determine if the CryET74 is the toxic component of the EG11529 strain a spore/crystal suspension of EG11935, which produces only CryET74, was compared in bioassay to spore/crystal suspensions of EG11529 and EG11936, which produces both CryET39 and CryET74. Data from replicated bioassays were pooled for probit analysis (Daum, 1970) with mortality being corrected for control death, the control being diluent only (Abbot, 1925). Results are reported as the amount of crystal protein per well (175 $mm^2$ of diet surface) resulting in an $LC_{50}$, the concentration killing 50% of the test insects. 95% confidence intervals are also reported in Table 17 below.

TABLE 17

| INSECTICIDAL ACTIVITY OF *B. thuringiensis* PROTEINS ON WCRW LARVAE | | |
|---|---|---|
| Sample | $LC_{50}$ (μg/well) | 95% C.I. |
| EG11935 | No Activity at 80 μg/well | |
| EG11529 | 9.78 | 6.9-12.5 |
| EG11936 | 14.5 | 9.7-19.5 |

The CryET74 protein produced by EG11935 had no activity on WCRW larvae, suggesting that the CryET39 protein, either alone or in combination with CryET74, was responsible for the insecticidal activity seen in EG11529 and EG11936.

An assay comparing a spore/crystal suspension of EG11937, which produces only the CryET39 crystal protein, with suspensions of EG11936 and EG11937 was performed. Also included in this assay were 50:50 mixtures of EG11935+EG11937 to see if a mixture of CryET39 and CryET74 had activity similar to that of EG11936. The data (Table 18) are expressed as percent control, which is mortality at a given dose corrected for control mortality in the diluent control. Two identical samples of EG11937 were prepared for the purposes of repetition.

TABLE 18

| Sample | Dose (μg/well) | Percent Control |
|---|---|---|
| EG11935 | 80 | 0 |
| EG11935 | 160 | 0 |
| EG11936 | 80 | 100 |
| EG11936 | 160 | 100 |
| EG11937 (1) | 80 | 10.5 |
| EG11937 (1) | 160 | 6.7 |
| EG11937 (2) | 80 | 13.3 |
| EG11937 (2) | 160 | 0 |
| EG11935 + EG11937 (1) | 80 | 100 |
| EG11935 + EG11937 (1) | 160 | 100 |
| EG11935 + EG11937 (2) | 80 | 100 |
| EG11935 + EG11937 (2) | 160 | 93.3 |

The results of this assay clearly demonstrated that CryET39 protein alone, as expressed in EG11937, does not account for the activity seen in EG11936 or EG11529. The addition of CryET74 to the CryET39 protein, however, resulted in a composition toxic to larvae of the WCRW. These data suggest that CryET39 and CryET74 interact to form the toxic component of EG11529 and EG11936.

5.12.3 Toxicity of the Crystal Proteins of EG11529 to CPB Larvae

A sporulated culture of EG11529 was harvested, washed and suspended as described above, to determine if the crystal proteins produced by EG11529 are toxic to the larvae of the Colorado potato beetle (CPB). The assay on CPB larvae was performed using techniques similar to those in the SCRW assay, except for the substitution of BioServe's #9380 insect diet (with potato flakes added) for the artificial diet. Mortality was scored at three days instead of seven days. For this assay 16 insects were used at a single dose of 140 μg/well. At this dose 100% of the larvae were killed demonstrating that EG11529 is toxic to CPB larvae.

5.13 Example 13

Identification of Genes Encoding Related δ-Endotoxin Polypeptides

*B. thuringiensis* strains producing crystal proteins of 40-50 kDa were identified by SDS-PAGE analysis of parasporal crystals produced by sporulating cultures. Total DNA was extracted from these strains following procedures described above, digested with the restriction endonuclease HindIII, and the restriction fragments resolved by agarose gel electrophoresis and blotted to nitrocellulose filters for Southern blot analysis. PCR™ was used to amplify a segment of the cryET39 gene for use as a hybridization probe to identify and clone related toxin genes from these *B. thuringiensis* strains. The PCR™ fragment extended from nucleotide 176 of the cryET39 coding sequence to approximately 200-bp 3' to the end of the gene and was generated using the opposing primers mr13 and mr24 and plasmid pEG1337 as a template.

```
mr13: 5'-TGACACAGCTATGGAGC-3'      (SEQ ID NO:33)

mr24: 5'-ATGATTGCCGGAATAGAAGC-3'   (SEQ ID NO:34)
```

The amplified DNA fragment was radioactively labeled using α-$^{32}$P-dATP and a random primer labeling kit (Prime-a-Gene® Labeling System; Promega Corporation, Madison, Wis.). Following incubation with the cryET39-specific hybridization probe, the filters were washed under moderately stringent conditions (e.g., in 0.1×-1.0×SSC at 55 C), and exposed to X-ray film to obtain an autoradiogram identifying DNA fragments containing cryET39-related sequences. Several strains yielded hybridization patterns that differed from that of EG5899. Three strains, designated EG4100, EG4851, and EG9444 respectively, were selected for further characterization.

The cloning and expression of the cry genes from strains EG4100, EG4851, and EG9444 was accomplished using procedures described in Section 5.4, Section 5.5 and Section 5.6. DNA was prepared from the strains and partially digested with the restriction enzyme MboI, resulting in an assortment of essentially random DNA fragments. The MboI fragments were resolved on an agarose gel and fragments in the 6-10-kb size range were purified. The purified MboI fragments were then ligated into a *B. thuringiensis/E. coli* shuttle vector, pHT315, previously digested with BamHI and treated with alkaline phosphatase. The ligation mixure was then used to transform *E. coli* to ampicillin resistance, thus constructing a library of cloned fragments representing the genome of each respective *B. thuringiensis* strain. The *E. coli* libraries were plated on LB agar containing 50 ug/ml ampicillin and the colonies transferred to nitrocellulose filters. To identify cryET39-related sequences the filters were probed with either the radiolabeled oligonucleotide wd271 (EG9444 library), as described in Section 5.4 and Section 5.5, or with the cryET39-specific hybridization probe described above (EG4100 and EG4851 libraries). Plasmid DNA was isolated from hybridizing *E. coli* colonies and used to transform an acrystalliferous *B. thuringiensis* host strain to erythromycin resistance. Recombinant *B. thuringiensis* clones were grown to sporulation in C2 medium and crystal proteins were analyzed by SDS-PAGE as described in Section 5.6.

A cloned fragment identified in the manner described above from the EG4100 library encoded an approximately 60-kDa crystal protein, designated CryET69 (SEQ ID NO:14). DNA sequence analysis revealed that the cryET69 gene (SEQ ID NO:13) encoded a protein of 520 amino acid residues. The CryET69 protein showed ~23% sequence identity to CryET39. The recombinant *B. thuringiensis* strain expressing CryET69 was designated EG11647 and the recombinant plasmid containing the cryET69 gene was designated pEG1820. EG4100 and EG11647 were deposited with the ARS Patent Culture Collection and given the NRRL accession numbers B-21786 and B-21787, respectively.

A cloned fragment isolated from the EG9444 library as described above encoded an approximately 45-kDa crystal protein, designated CryET71, that was related to CryET39, and an approximately 14-kDa crystal protein, designated CryET79, that was related to CryET74. DNA sequence analysis revealed that the cryET71 gene (SEQ ID NO:11) encodes a protein of 397 amino acids and that the cryET79 gene (SEQ ID NO:9) encodes a protein of 123 amino acids. The CryET71 protein (SEQ ID NO:12) showed 78% sequence identity to CryET39 while the CryET79 protein (SEQ ID NO:10) showed 80% sequence identity to CryET74. The recombinant *B. thuringiensis* strain expressing CryET71 and CryET79 was designated EG11648 and the recombinant plasmid containing the cryET71 and cryET79 genes was designated pEG1821 (Table 9). EG11648 was toxic to larvae of the WCRW. By analogy to the related CryET39 and CryET74 proteins, it was presumed that both CryET71 and CryET79 were required for full WCRW toxicity. EG9444 and EG11648 have been deposited with the ARS Patent Culture Collection and given the NRRL accession numbers B-21785 and B-21788, respectively.

A cloned fragment isolated from the EG4851 library as described above encoded an approximately 44-kDa crystal protein, designated CryET76, that was related to CryET39, and an approximately 15-kDa protein, designated CryET80, that was related to CryET74. DNA sequence analysis revealed that the cryET76 gene (SEQ ID NO:1) encoded a protein of 387 amino acids and that the cryET80 gene (SEQ ID NO:3) encoded a protein of 132 amino acids. The CryET76 protein (SEQ ID NO:2) showed 61% sequence identity to CryET39 while the CryET80 protein SEQ ID NO:4) showed 52% sequence identity to CryET74. The recombinant *B. thuringiensis* strain expressing CryET76 and CryET80 was designated EG11658, and the recombinant plasmid containing the cryET76 and cryET80 genes has been designated pEG1823 (Table 9). EG11658 was toxic to larvae of the WCRW. By analogy to the related CryET39 and CryET74 proteins, it was presumed that both CryET76 and CryET80 were required for full WCRW toxicity. EG4851 and EG11658 were deposited with the ARS Patent Culture Collection and given the NRRL accession numbers B-21915 and B-21916, respectively.

Based on these results, the inventors contemplate that the utilization of procedures similar to those described herein will lead to the discovery and isolation of additional *B. thuringiensis* crystal protein toxins. DNA probes, based on the novel sequences disclosed herein may be prepared from oligonucleotides, PCR™ products, or restriction fragments and used to identify additional genes related to those described herein. These new genes may also be cloned, characterized by DNA sequencing, and their encoded proteins evaluated in bioassay on a variety of insect pests using the methods described herein. Novel genes, in turn, may therefore result in the identification of new families of related genes, as seen in the above Examples.

5.14 Example 14

Sequencing of Related Cry Genes

5.14.1 CryET71

An initial nucleotide sequence for the cryET71 gene was obtained using the oligonucleotide wd271 as a sequencing primer and procedures described in Section 5.7. Successive oligonucleotides to be used for priming sequencing reactions were designed from the sequencing data of the previous set of reactions to obtain the complete the sequence of the cryET71 gene.

The DNA sequence of the CryET71 gene is represented by SEQ ID NO:11, and encodes the amino acid sequence of the CryET71 polypeptide, represented by SEQ ID NO:12.

5.14.1.4 Characteristics of the CryET71 Polypeptide

The CryET71 polypeptide comprises a 397-amino acid sequence, has a calculated molecular mass of 45,576 Da, and has a calculated pI equal to 4.75. The amino acid composition of the CryET71 polypeptide is given in Table 19.

TABLE 19

AMINO ACID COMPOSITION OF CRYET71

| Amino Acid | # Residues | % Total |
|---|---|---|
| Ala | 11 | 2.7 |
| Arg | 8 | 2.0 |
| Asn | 38 | 9.5 |
| Asp | 28 | 7.0 |
| Cys | 2 | 0.5 |
| Gln | 25 | 6.2 |
| Glu | 22 | 5.5 |
| Gly | 19 | 4.7 |
| His | 5 | 1.2 |
| Ile | 41 | 10.3 |
| Leu | 31 | 7.8 |
| Lys | 30 | 7.5 |
| Met | 8 | 2.0 |
| Phe | 6 | 1.5 |
| Pro | 16 | 4.0 |
| Ser | 29 | 7.3 |
| Thr | 33 | 8.3 |
| Trp | 7 | 1.7 |
| Tyr | 24 | 6.0 |
| Val | 14 | 3.5 |
| Acidic (Asp + Glu) | 50 | |
| Basic (Arg + Lys) | 38 | |
| Aromatic (Phe + Trp + Tyr) | 37 | |
| Hydrophobic (Aromatic + Ile + Leu + Met + Val) | 131 | |

5.14.2 CryET79

An initial sequence for the upstream cryET79 gene was obtained using an oligonucleotide primer designed from the completed cryET71 sequence. DNA samples were sequenced using the ABI PRISM™ DyeDeoxy sequencing chemistry kit (Applied Biosystems) according to the manufacturer's protocol. The completed reactions were run on as ABI 377 automated DNA sequencer. DNA sequence data were analyzed using Sequencher v3.0 DNA analysis software (Gene Codes Corp.). Successive oligonucleotides to be used for priming sequencing reactions were designed from the sequencing data of the previous set of reactions to obtain the complete cryET79 gene sequence.

5.14.2.3 Characteristics of the CryET79 Polypeptide

The CryET79 polypeptide comprises a 123-amino acid sequence, has a calculated molecular mass of 13,609 Da, and has a calculated pI equal to 6.32. The amino acid composition of the CryET79 polypeptide is given in Table 20.

TABLE 20

AMINO ACID COMPOSITION OF CRYET79

| Amino Acid | # Residues | % Total |
|---|---|---|
| Ala | 5 | 4.0 |
| Arg | 4 | 3.2 |
| Asn | 12 | 9.7 |
| Asp | 5 | 4.0 |
| Cys | 0 | 0 |
| Gln | 6 | 4.8 |
| Glu | 7 | 5.6 |
| Gly | 13 | 10.5 |
| His | 6 | 4.8 |
| Ile | 6 | 4.8 |
| Leu | 4 | 3.2 |
| Lys | 6 | 4.8 |
| Met | 2 | 1.6 |
| Phe | 3 | 2.4 |
| Pro | 3 | 2.4 |
| Ser | 13 | 10.5 |
| Thr | 13 | 10.5 |
| Trp | 1 | 0.8 |
| Tyr | 8 | 6.5 |
| Val | 6 | 4.8 |
| Acidic (Asp + Glu) | 12 | |
| Basic (Arg + Lys) | 10 | |
| Aromatic (Phe + Trp + Tyr) | 12 | |
| Hydrophobic (Aromatic + Ile + Leu + Met + Val) | 30 | |

5.14.3 CryET69

The $NH_2$-terminal amino acid sequence of the isolated CryET69 protein was determined using procedures described in Section 5.3. The $NH_2$-terminal sequence of the isolated protein was:

```
                                         (SEQ ID NO:29)
  1   2   3   4   5   6   7   8   9  10  11
Met Asn Val Asn His Gly Met Ser Cys Gly Cys
```

An oligonucleotide primer based on the $NH_2$-terminal amino acid sequence of the CryET69 protein was designed for use in sequencing cryET69. This oligonucleotide, designated crc12, has the following sequence:

```
5'-ATGAATGTAAATCATGGGATGWSNTGT-3'    (SEQ ID NO:30)
```

where W=A and T and S=C and G. An initial nucleotide sequence was obtained using crc12 as a sequencing primer and procedures described in Section 5.7. Successive oligonucleotides to be used for priming sequencing reactions were designed from the sequencing data of the previous set of reactions. The completion of the sequence was achieved using automated sequencing. DNA samples were sequenced using the ABI PRISM DyeDeoxy sequencing chemistry kit (Applied Biosystems) according to the manufacturer's protocol. The completed reactions were run on as ABI 377 automated DNA sequencer. DNA sequence data were analyzed using Sequencher v3.0 DNA analysis software (Gene Codes Corp.).

5.14.3.3 Characteristics of the CryET69 Polypeptide

The CryET69 polypeptide comprises a 520-amino acid sequence, has a calculated molecular mass of 58,609 Da, and has a calculated pI equal to 5.84. The amino acid composition of the CryET69 polypeptide is given in Table 21.

TABLE 21

AMINO ACID COMPOSITION OF CRYET69

| Amino Acid | # Residues | % Total |
|---|---|---|
| Ala | 24 | 4.6 |
| Arg | 30 | 5.7 |
| Asn | 60 | 11.5 |
| Asp | 27 | 5.1 |
| Cys | 9 | 1.7 |
| Gln | 32 | 6.1 |
| Glu | 24 | 4.6 |
| Gly | 32 | 6.1 |
| His | 9 | 1.7 |
| Ile | 24 | 4.6 |
| Leu | 31 | 5.9 |
| Lys | 15 | 2.8 |
| Met | 10 | 1.9 |
| Phe | 20 | 3.8 |
| Pro | 24 | 4.6 |
| Ser | 39 | 7.5 |
| Thr | 48 | 9.2 |
| Trp | 6 | 1.1 |
| Tyr | 22 | 4.2 |
| Val | 34 | 6.5 |
| Acidic (Asp + Glu) | 51 | |
| Basic (Arg + Lys) | 45 | |
| Aromatic (Phe + Trp + Tyr) | 48 | |
| Hydrophobic (Aromatic + Ile + Leu + Met + Val) | 147 | |

5.16 Example 16

Database Searches for CryET69-Related Proteins

The deduced amino acid sequence for CryET69 was used to query the SWISS-PROT ALL and nr databases using FASTA and BLASTP as described for CryET39 in Section 5.8 except that the blosum50 comparison matrix was used for the FASTA search. The results of the FASTA search indicated that CryET69 showed ~32% sequence identity over a 338-amino acid region with the 42-kDa mosquitocidal crystal protein of *B. sphaericus* and ~30% sequence identity over a 440-amino acid region with the 51-kDa crystal protein of *B. sphaericus*.

5.17 Example 17

Database Searches for CryET71- and CryET79-Related Proteins

The deduced amino acid sequences for CryET71 and CryET79 were used to query the SWISS-PROT ALL and nr databases using FASTA and BLASTP as described for CryET39 in Section 5.8. The results of the FASTA search indicated that CryET71 showed ~25% sequence identity over a 323-amino acid region with the 42-kDa mosquitocidal crystal protein of *B. sphaericus* and ~25% sequence identity over a 388-amino acid region with the 51-kDa crystal protein of *B. sphaericus*. The FASTA and BLASTP searches did not identify proteins with significant sequence identity to CryET79.

5.18 Example 18

Sequencing of the CryET76 and CryET80 Genes

A partial DNA sequence of the genes cloned on pEG1823 was determined following established dideoxy chain-termination DNA sequencing procedures (Sanger et al., 1977). Preparation of the double stranded plasmid template DNA was accomplished using a Wizard® SV Miniprep Kit (Promega Corp.) following the manufacturer's procedures or a Qiagen Plasmid Kit (Qiagen Inc.) following the manufacturer's procedures, followed by a phenol:chloroform: isoamyl alcohol (50:48:2) extraction and then a chlorform: isoamyl alcohol (24:1) extraction. The sequencing reactions were performed using the Sequenase™ Version 2.0 DNA Sequencing Kit (United States Biochemical/Amersham Life Science Inc.) following the manufacturer's procedures and using $^{35}$S-[dATP] as the labeling isotope (DuPont NEN® Research Products). Denaturing gel electrophoresis of the reactions was performed on a 6% (wt./vol.) acrylamide, 42% (wt./vol.) urea sequencing gel or on a CastAway™ Precast 6% acrylamide sequencing gel (Stratagene). The dried gel was exposed to Kodak X-OMAT AR X-ray film (Eastman Kodak) overnight at room temperature to obtain an autoradiogram.

A partial DNA sequence for the cryET76 and cryET80 genes on pEG1823 was obtained by using the procedures described above. The cryET39-specific oligonucleotide mr18 was used as the initial sequencing primer. The sequence of mr18 is:

```
5'-GTACCAGAAGTAGGAGG-3'        (SEQ ID NO.31)
```

Successive oligonucleotides to be used for priming sequencing reactions were designed from the sequencing data of the previous set of reactions. The completion of the sequence was achieved using automated sequencing. DNA samples were sequenced using the ABI PRISM DyeDeoxy sequencing chemistry kit (Applied Biosystems) according to the manufacturer's suggested protocol. The completed reactions were run on as ABI 377 automated DNA sequencer. DNA sequence data were analyzed using Sequencher v3.0 DNA analysis software (Gene Codes Corp.). The DNA sequence of cryET76 (SEQ ID NO:1) and cryET80 (SEQ ID NO:3) is shown below. The deduced amino acid sequence of the CryET76 protein (SEQ ID NO:2) and the CryET80 protein (SEQ ID NO:4) is also shown below. The entire sequenced region is shown in (SEQ ID NO:17).

5.18.1 CryET76

The DNA sequence of the CryET76 gene is represented by SEQ ID NO:1, and encodes the amino acid sequence of the CryET76 polypeptide, represented by SEQ ID NO:2.

5.18.1.3 Characteristics of the CryET76 Polypeptide

The CryET76 polypeptide comprises a 387-amino acid sequence, has a calculated molecular mass of 43,812 Da, and has a calculated pI equal to 5.39. The amino acid composition of the CryET76 polypeptide is given in Table 22.

TABLE 22

AMINO ACID COMPOSITION OF CRYET76

| Amino Acid | # Residues | % Total |
|---|---|---|
| Ala | 14 | 3.6 |
| Arg | 7 | 1.8 |
| Asn | 39 | 10.0 |
| Asp | 17 | 4.3 |
| Cys | 1 | 0.2 |
| Gln | 17 | 4.3 |
| Glu | 22 | 5.6 |
| Gly | 22 | 5.6 |
| His | 4 | 1.0 |
| Ile | 31 | 8.0 |
| Leu | 34 | 8.7 |
| Lys | 27 | 6.9 |
| Met | 5 | 1.2 |
| Phe | 8 | 2.0 |
| Pro | 10 | 2.5 |
| Ser | 30 | 7.7 |
| Thr | 47 | 12.1 |
| Trp | 8 | 2.0 |
| Tyr | 24 | 6.2 |
| Val | 20 | 5.1 |
| Acidic (Asp + Glu) | 39 | |
| Basic (Arg + Lys) | 34 | |
| Aromatic (Phe + Trp + Tyr) | 40 | |
| Hydrophobic (Aromatic + Ile + Leu + Met + Val) | 130 | |

5.18.2 CryET80

The DNA sequence of the CryET80 gene is represented by SEQ ID NO:3, and encodes the amino acid sequence of the CryET80 polypeptide, represented by SEQ ID NO:4.

5.18.2.3 Characteristics of the CryET80 Polypeptide

The CryET80 polypeptide comprises a 132-amino acid sequence, has a calculated molecular mass of 14,839 Da, and has a calculated pI equal to 6.03. The amino acid composition of the CryET80 polypeptide is given in Table 23.

TABLE 23

AMINO ACID COMPOSITION OF CRYET80

| Amino Acid | # Residues | % Total |
|---|---|---|
| Ala | 7 | 5.3 |
| Arg | 8 | 6.0 |
| Asn | 13 | 9.8 |
| Asp | 8 | 6.0 |
| Cys | 1 | 0.7 |
| Gln | 3 | 2.2 |
| Glu | 8 | 6.0 |
| Gly | 9 | 6.8 |
| His | 8 | 6.0 |
| Ile | 13 | 9.8 |
| Leu | 6 | 4.5 |
| Lys | 4 | 3.0 |
| Met | 2 | 1.5 |
| Phe | 2 | 1.5 |
| Pro | 3 | 2.2 |
| Ser | 11 | 8.3 |
| Thr | 11 | 8.3 |
| Trp | 1 | 0.7 |
| Tyr | 6 | 4.5 |
| Val | 8 | 6.0 |
| Acidic (Asp + Glu) | 16 | |
| Basic (Arg + Lys) | 12 | |
| Aromatic (Phe + Trp + Tyr) | 9 | |
| Hydrophobic (Aromatic + Ile + Leu + Met + Val) | 38 | |

5.18.3 Characteristics of the CryET76, CryET80 and CryET84 Genes Isolated from EG4851 (SEQ ID NO:17)

The DNA sequence of the entire three gene operon containing the CryET76, CryET80, and CryET84 coding regions is represented by SEQ ID NO:17.

In strain EG4851, the cryET84 gene is located immediately 5' to the cryET80 and cryET76 genes. The cryET84 gene begins at nucleotide 656 and ends at nucleotide 1681. The cryET80 gene begins at nucleotide 1773 and ends at nucleotide 2168. The cryET76 gene begins at nucleotide 2264 and ends at nucleotide 3424.

5.19 Example 19

Analysis of Sequence Homologies 5.19.1 Database Searches for CryET76- and CryET80-Related Proteins The amino acid sequences of the CryET76 and CryET80 proteins, deduced by translation of the nucleotide sequence, were used to query sequence databases for related protein sequences. The SWISS-PROT ALL database was queried using FASTA version 3.15 (Pearson and Lipman, 1988) provided by the FASTA server at European Biotechnology Institute using the following parameters (library=swall, matrix=pam150, ktup=2, gapcost=−12, gapxcost=−2). The amino acid sequences of CryET76 and CryET80were also used to query the non-redundant (nr) database of the National Center Biotechnology Information (NCBI) using BLASTP version 2.0 (Altschul et al., 1997) with the following parameters: matrix=blosum62, gapped alignment, other parameters=default settings.

The results of the FASTA analysis revealed that CryET76 showed ~27% sequence identity over a 320-amino acid region with the 42-kDa mosquitocidal crystal protein from *B. sphaericus* while CryET80 showed no significant sequence similarity to sequences in SWISS-PROT ALL. The results of the BLASTP search were in general agreement with those of the FASTA search. No proteins with significant sequence similarity to CryET80 were identified.

5.19.2 Additional Sequence Comparisons with Cry Proteins

Sequence alignments were performed to compare the CryET39, CryET74, CryET75, CryET71, CryET79, CryET76, CryET80 and CryET69 sequences with sequences from recently published patent applications. The alignments were performed using PALIGN in the PC/GENE version 6.85 sequence analysis package (Intelligenetics Corp. Mountain View, Calif.). The pairwise alignments were performed using the following parameters: comparison matrix=unitary, open gap cost=3, unit gap cost=1.

5.19.2.1 CryET39

Sequence alignment comparing the CryET39 sequence with sequences from recently published patent applications revealed sequence similarity between CryET39 and proteins identified by sequence identifiers 11, 38 and 43 of Intl. Pat. Appl. Publ. No. WO 97/40162. CryET39 showed a 99.2% sequence identity to sequence number 11, 78.6% sequence identity to sequence number 38, and 79.9% sequence identity to sequence number 43.

5.19.2.2 CryET74

Sequence alignment comparing the CryET74 sequence with sequences from recently published patent applications revealed sequence similarity between CryET74 and sequence identifier numbers 32, 36, and 41 of the Intl. Pat. Appl. Publ. No. WO 97/40162. CryET74 shows 100% sequence identity with sequence identifier number 32, 80.7% sequence identity with sequence identifier number 36, and 77.3% sequence identity with sequence identifier number 41 of that application.

5.19.2.3 CryET75

Sequence alignment comparing CryET75 with sequences from recently published patent applications revealed approximately 26% sequence identity between CryET75 and CryET33, a coleopteran-toxic protein, disclosed in Intl. Pat. Appl. Publ. No. WO 97/17600.

5.19.2.4 CryET71

Sequence alignment comparing the CryET71 sequence with sequences from recently published patent applications revealed sequence similarity between CryET71 and sequence identifier numbers 11, 38, and 43 of the Intl. Pat. Appl. Publ. No. WO 97/40162. CryET71 showed 78.4% sequence identity with sequence identifier number 11; 91.9% sequence identity with sequence identifier number 38; and 97.4% sequence identity with sequence identifier number 43.

5.19.2.5 CryET79

Sequence alignment comparing the CryET79 sequence with sequences from recently published patent applications revealed sequence similarity between CryET79 and the sequences identifier numbers 32, 36, and 41 of the Intl. Pat. Appl. Publ. No. WO 97/40162. CryET79 showed 79.8% sequence identity with sequence identifier number 32; 95.9% sequence identity with sequence identifier number 36; and 91% sequence identity with sequence identifier number 41.

5.19.2.6 CryET76

Sequence alignment comparing the CryET76 sequence with sequences from recently published patent applications revealed sequence similarity between CryET76 and sequence identifier numbers 11, 38, and 43 of the Intl. Pat. Appl. Publ. No. WO 97/40162. CryET76 showed 60.8% sequence identity to sequence identifier number 11; 61.6% sequence identity to sequence identifier number 38; and 61.9% sequence identity to sequence identifier number 43.

5.19.2.7 CryET80

Sequence alignment comparing the CryET80 sequence with sequences from recently published patent applications revealed sequence similarity between CryET80 and sequence identifier numbers 32, 36, and 41 of the Intl. Pat. Appl. Publ. No. WO 97/40162. CryET80 showed 52.1% sequence identity to sequence identifier number 32; 56.1% sequence identity to sequence identifier number 36; and 54.5% sequence identity to sequence identifier number 41.

5.19.2.8 CryET69

Sequence alignment comparing the CryET69 sequence revealed only 23-25% sequence identity between CryET69 and sequence identifier numbers 11, 38, and 43 of the Intl. Pat. Appl. Publ. No. WO 97/40162. This crystal protein showed a higher degree of homology to the mosquitocidal crystal proteins of *B. sphaericus* than to the crystal proteins of *B. thuringiensis*.

5.19.3 Summary

These analyses demonstrated that the amino acid sequences of CryET69, CryET75, CryET76 and CryET80 are markedly different from the sequences of previously described insecticidal crystal proteins. Employing the nomenclature established for *B. thuringiensis* crystal proteins (Crickmore et al., 1998), CryET76 and CryET80 would be assigned a new secondary rank and CryET69 and CryET75 would be assigned a new primary rank.

5.20 Example 20

Expression of Recombinant CryET76 and CryET80 Polypeptides

To characterize the properties of the CryET76 and CryET80 proteins, it was necessary to express the cloned cryET76 and cryET80 genes in a *B. thuringiensis* strain that did not produce other crystal proteins (i.e. a Cry$^-$ strain). The plasmid containing the cloned cryET76 and cryET80 genes, pEG1823, contains a *B. thuringiensis* origin of replication as well as an origin that directs replication in *E. coli*, as described above. pEG1823 was used to transform the Cry$^-$ *B. thuringiensis* strain EG10650 to erythromycin resistance ($Em^R$) by electroporation (Macaluso and Mettus, 1991). Cells transformed to $Em^R$ were selected by incubation overnight on LB agar plates containing 25 μg/ml erythromycin. One $Em^R$ colony from each transformation was selected for further analysis. One isolate was designated EG11658.

EG11658 was grown in C2 sporulation medium containing 25 μg/ml erythromycin for four days at 25° C., at which point sporulation and cell lysis had occurred. Microscopic examination of the sporulated cultures demonstrated that the recombinant strain was producing parasporal inclusions. The sporulated culture of EG11658 was harvested by centrifugation, washed, and resuspended at one-tenth the original volume in $H_2O$. The crystal protein in the suspension was characterized by SDS-PAGE analysis which revealed the production of approximately 44- and 15-kDa proteins.

5.21 Example 21

Toxicity of CryET76 and CryET80 to Insects

The toxicity of CryET76 and CryET80 protein towards WCRW was determined.

EG11658 was grown in C2 medium at 25° C. for four days until sporulation and cell lysis had occurred. The culture was harvested by centrifugation, washed in approximately 2.5 times the original volume with distilled $H_2O$, and resuspended in 0.005% Triton X-100® at one-tenth the original volume. For comparison with EG11658, the recombinant *B. thuringiensis* strains, EG11529, producing the WCRW-toxic proteins CryET39 and CryET74, and EG11648, producing the WCRW-toxic proteins CryET71 and CryET79, were grown and harvested in the same manner. Toxin proteins from the samples were quantified by SDS-PAGE as described (Brussock and Currier, 1990. The procedure was modified to eliminate the neutralization step with 3M HEPES.

WCRW larvae were bioassayed via surface contamination of an artificial diet (20 g agar, 50 g wheatgerm, 39 g sucrose, 32 g casein, 14 g fiber, 9 g Wesson salts mix, 1 g methyl paraben, 0.5 g sorbic acid, 0.06 g cholesterol, 9 g Vanderzant's vitamin mix, 0.5 ml linseed oil, 2.5 ml phosphoric/propionic acid per 1 liter). Each bioassay of EG11658 (CryET76 and CryET80), EG11529 (CryET39 and CryET74), and EG11648 (CryET71 and CryET79) consisted of eight serial aqueous dilutions with aliquots applied to the surface of the diet. After the diluent (an aqueous 0.005% Triton X-100® solution) had dried, neonate larvae were placed on the diet and incubated at 28° C. Thirty-two larvae were tested per dose. Mortality was scored after seven days. Data from replicated bioassays were pooled for probit analysis (Daum, 1970) with mortality being corrected for control death, the control being diluent only (Abbott, 1925). Results are reported as the amount of crystal protein per well (175 $mm^2$ of diet surface) resulting in an $LC_{50}$, the concentration killing 50% of the test insects. 95% confidence intervals are also reported for the $LC_{50}$ values (Table 24).

TABLE 24

INSECTICIDAL ACTIVITY OF CRY PROTEINS TO WCRW LARVAE

| Sample | Crystal Protein | $LC_{50}$ (μg protein/well) | 95% C.I. | $LC_{95}$ (μg protein/well) |
|---|---|---|---|---|
| EG11658 | CryET76<br>CryET80 | 10.7 | 2.2-18.9 | 46 |
| EG11648 | CryET71<br>CryET79 | 5.3 | 0.9-10.1 | 27 |
| EG11936 | CryET39<br>CryET74 | 12.3 | 12.5-14.3 | 32 |

The results shown in Table 24 demonstrated that the CryET76 and CryET80 proteins had significant activity on WCRW larvae.

5.22 Example 22

Toxicity of CryET69 to Incests

The toxicity of CryET69 towards WCRW was determined using procedures described in Section 5.21. Results are reported as the amount of crystal protein per well (175 $mm^2$ of diet surface) resulting in an $LC_{50}$, the concentration killing 50% of the test insects. 95% confidence intervals are also reported for the $LC_{50}$ values (Table 25).

TABLE 25

INSECTICIDAL ACTIVITY OF CRYET69 TO WCRW LARVAE

| Sample | Crystal Protein | $LC_{50}$ (μg protein/well) | 95% C.I. | $LC_{95}$ (μg protein/well) |
|---|---|---|---|---|
| EG11204 | Cry3B2 | 13.8 | 3.2-30.1 | 502 |
| EG11647 | CryET69 | 147.3 | 73-1292 | 6190 |

Control mortality=22%

These results demonstrated that CryET69 was significantly less active than Cry3B2 against WCRW. Nevertheless, this crystal protein apparently represents a new class of coleopteran-toxic δ-endotoxins.

5.23 Example 23

Construction of Strains EG12156 and EG12158

Recombinant *B. thuringiensis* strains were constructed that produce either CryET76 or CryET80. A frameshift mutation was introduced into the cryET76 coding sequence on pEG1823 to generate a recombinant plasmid capable of directing the production of CryET80 alone. A unique AgeI restriction site within the cryET76 coding sequence was identified by computer analysis of the determined cryET76 nucleotide sequence. Subsequent digestion of pEG1823 with AgeI confirmed that this restriction site was unique to the plasmid. To generate a frameshift mutation at this site, pEG1823 was digested with AgeI and the DNA ends blunt-ended with T4 polymerase in the presence of dNTPs. The linear DNA fragment was subsequently resolved by electrophoresis on a 1% agarose gel, the DNA band excised with a razor blade, and the DNA purified using the Qiagen gel extraction kit. The purified DNA was self-ligated using T4 ligase and used to transform the *E. coli* strain DH5α to ampicillin resistance. Restriction enzyme analysis of DNA recovered from several ampicillin-resistant clones confirmed the disruption of the AgeI site on pEG1823. The recombinant plasmid from one such clone was designated pEG2206. pEG2206 was subsequently used to transform, via electroporation, the acrystalliferous *B. thuringiensis* strain EG10650 to erythromycin resistance. The recombinant Bt strain containing pEG2206 was designated EG12156.

A deletion mutation was introduced into the cryET80 coding sequence on pEG1823 to generate a recombinant plasmid capable of directing the production of CryET76 alone. A unique DraIII restriction site within the cryET80 coding sequence was identified by computer analysis of the determined cryET80 nucleotide sequence. Subsequent digestion of pEG1823 with DraIII confirmed that this restriction site was unique to the plasmid. To generate a mutation at this site, pEG1823 was digested with DraIII and the DNA ends blunt-ended with T4 polymerase in the presence of dNTPs. The linear DNA fragment was subsequently resolved by electrophoresis on a 1% agarose gel, the DNA band excised with a razor blade, and the DNA purified using the Qiagen gel extraction kit. The purified DNA was self-ligated using T4 ligase and used to transform the *E. coli* strain DH5α to ampicillin resistance. Restriction enzyme analysis of DNA recovered from several ampicillin-resistant clones confirmed the disruption of the DraIII site on pEG1823. The recombinant plasmid from one such clone was designated pEG2207. pEG2207 was subsequently used to transform, via electroporation, the acrystalliferous *B. thuringiensis* strain EG10650 to erythromycin resistance. The recombinant strain containing pEG2207 was designated EG12158.

Strains EG11658, EG12156, and EG12158 were used to inoculate 100 ml C2 broth cultures containing 10 μg/ml erythromycin. The broth cultures were grown with shaking in 500 ml baffled flasks at 28-30° C. for 3 days at which time the cultures were fully sporulated and the sporangia lysed. The spores and crystals were pelleted by centrifugation at 8,000 rpm (~9800×g) in a JA14 rotor for 20 min at 4° C. The pellets were suspended in 50 ml of 10 mM Tris-HCl, 50 mM NaCl, 1 mM EDTA, 0.005% Triton® X-100 (pH 7.0). The spores and crystals were pelleted again by centrifugation at 3,750 rpm (~3200×g) in a Beckman GPR centrifuge for 1 hour at 4° C. The pellets were resuspended in 10 ml of 10 mM Tris-HCl, 50 mM NaCl, 1 mM EDTA, 0.005% Triton® X-100 (pH 7.0) and stored at 4-8° C.

Crystal proteins produced by these cultures were detected by SDS-PAGE and subsequent staining of the SDS gels with Coomassie Brilliant Blue R-250 as described in Section 5.11. The results of this analysis confirmed that strain EG12156 produced CryET80, but not CryET76, while strain EG12158 produced CryET76, but not CryET80 (FIG. 3). Thus, each crystal protein could be produced independently of the other crystal protein. The role of each crystal protein in effecting toxicity towards WCRW larvae may now be studied in even greater detail.

The SDS-PAGE analysis described in FIG. 3 also revealed the presence of an additional protein present in both the EG12156 and EG12158 crystal preparations. This protein exhibited an apparent molecular mass of approximately 35 kDa and was designated CryET84.

Additional DNA sequence analysis of the cloned insert in pEG1823 revealed a third open reading frame sufficient to code for a ~38-kDa protein (SEQ ID NO:19). This coding region is located immediately 5' to the cryET80 gene. Thus, cryET84, cryET80, and cryET76 may comprise an operon. The CryET84 protein isolated from EG4851 comprises a 341-amino acid sequence, and has a calculated molecular mass of approximately 37,884 Da. CryET84 has a calculated isoelectric constant (pI) equal to 5.5.

SDS-PAGE analysis of the EG11658 crystal proteins used for the WCRW bioassays described in Section 5.21 did not detect the CryET84 protein band. Apparently, subtle differences in the cultivation of the strain or in the harvesting and washing of the spore-crystal suspension can result in the loss of CryET84.

Sequence comparisons using Blast 2.0 and FASTA 3, as described in Example 8, revealed no significant sequence similarity between CryET84 and all known *B. thuringiensis* crystal proteins.

5.24 Example 24

Preparation of Insect-Resistant Transgenic Plants 5.24.1 Plant Transgene Construction The expression of a plant transgene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., U.S. Pat. No. 5,463,175, specifically incorporated herein by reference).

The particular promoter selected should be capable of causing sufficient expression of the enzyme coding sequence to result in the production of an effective amount of protein. One set of preferred promoters are constitutive promoters such as the CaMV35S or FMV35S promoters that yield high levels of expression in most plant organs (U.S. Pat. No. 5,378,619, specifically incorporated herein by reference). Another set of preferred promoters are root enhanced or specific promoters such as the CaMV derived 4 as-1 promoter or the wheat POX1 promoter (U.S. Pat. No. 5,023,179, specifically incorporated herein by reference; Hertig et al., 1991). The root enhanced or specific promoters would be particularly preferred for the control of corn rootworm (*Diabroticus* spp.) in transgenic corn plants.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eucaryotic genes, or from a synthetic gene sequence. The present invention is not limited to constructs wherein the non-translated region is derived from the 5' non-translated sequence that accompanies the promoter sequence.

For optimized expression in monocotyledenous plants such as maize, an intron may also be included in the DNA expression construct. This intron would typically be placed near the 5' end of the mRNA in untranslated sequence. This intron could be obtained from, but not limited to, a set of introns consisting of the maize hsp70 intron (U.S. Pat. No. 5,424,412; specifically incorporated herein by reference) or the rice Act1 intron (McElroy et al., 1990).

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of *Agrobacterium* tumor-inducing (Ti) plasmid genes, such as the nopaline synthase (NOS) gene and (2) plant genes such as the pea ssRUBISCO E9 gene (Wong et al., 1992).

5.24.2 Plant Transformation and Expression

A transgene containing a δ-endotoxin coding sequence of the present invention can be inserted into the genome of a plant by any suitable method such as those detailed herein. Suitable plant transformation vectors include those derived from a Ti plasmid of *A. tumefaciens*, as well as those disclosed, e.g., by Herrera-Estrella (1983), Bevan et al. (1983), Klee (1985) and Eur. Pat. Appl. Publ. No. EP0120516. In addition to plant transformation vectors derived from the Ti or root-inducing (Ri) plasmids of *A. tumefaciens*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Fromm et al., 1990). Such methods are described in detail in Section 4.0.

5.24.3 Construction of Plant Expression Vectors

For efficient expression of the polynucleotides disclosed herein in transgenic plants, the selected sequence region(s) encoding the insecticidal polypeptide(s) must have a suitable sequence composition (Diehn et al., 1996).

For example, to place one or more of cry genes described herein in a vector suitable for expression in monocotyledonous plants (e.g., under control of the enhanced Cauliflower Mosaic Virus 35S promoter and link to the hsp70 intron followed by a nopaline synthase polyadenylation site as in U.S. Pat. No. 5,424,412, specifically incorporated herein by reference), the vector may be digested with appropriate enzymes such as NcoI and EcoRI. The larger vector band of approximately 4.6 kb is then electrophoresed, purified, and ligated with T4 DNA ligase to the appropriate restriction fragment containing the plantized cry gene. The ligation mix is then transformed into *E. coli*, carbenicillin resistant colonies recovered and plasmid DNA recovered by DNA miniprep procedures. The DNA may then be subjected to restriction endonuclease analysis with enzymes such as NcoI and EcoRI (together), NotI, and PstI to identify clones containing the cry gene coding sequence fused to the hsp70 intron under control of the enhanced CaMV35S promoter).

To place the δ-endotoxin gene in a vector suitable for recovery of stably transformed and insect resistant plants, the restriction fragment from pMON33708 containing the lysine oxidase coding sequence fused to the hsp70 intron under control of the enhanced CaMV35S promoter may be isolated by gel electrophoresis and purification. This fragment can then be ligated with a vector such as pMON30460 treated with NotI and calf intestinal alkaline phosphatase (pMON30460 contains the neomycin phosphotransferase coding sequence under control of the CaMV35S promoter). Kanamycin resistant colonies may then be obtained by transformation of this ligation mix into *E. coli* and colonies containing the resulting plasmid can be identified by restriction endonuclease digestion of plasmid miniprep DNAs. Restriction enzymes such as NotI, EcoRV, HindIII, NcoI, EcoRI, and BglII can be used to identify the appropriate clones containing the restriction fragment properly inserted in the corresponding site of pMON30460, in the orientation such that both genes are in tandem (i.e. the 3' end of the cry gene expression cassette is linked to the 5' end of the nptII expression cassette). Expression of the Cry proteins by the resulting vector is then confirmed in plant protoplasts by electroporation of the vector into protoplasts followed by protein blot and ELISA analysis. This vector can be introduced into the genomic DNA of plant embryos such as maize by particle gun bombardment followed by paromomycin selection to obtain corn plants expressing the cry gene essentially as described in U.S. Pat. No. 5,424,412, specifically incorporated herein by reference. In this example, the vector was introduced via cobombardment with a hygromycin resistance conferring plasmid into immature embryo scutella (IES) of maize, followed by hygromycin selection, and regeneration. Transgenic plant lines expressing the selected cry protein are then identified by ELISA analysis. Progeny seed from these events may then subsequently tested for protection from susceptible insect feeding.

5.25 Example 25

Modification of Bacterial Genes for Expression in Plants

Many wild-type genes encoding bacterial crystal proteins are known to be expressed poorly in plants as a full-length gene or as a truncated gene. Typically, the G+C content of a cry gene is low (37%) and often contains many A+T rich regions, potential polyadenylation sites and numerous ATTTA sequences. Table 26 shows a list of potential polyadenylation sequences which should be avoided when preparing the "plantized" gene construct.

TABLE 26

| LIST OF SEQUENCES OF POTENTIAL POLYADENYLATION SIGNALS | |
|---|---|
| AATAAA* | AAGCAT |
| AATAAT* | ATTAAT |
| AACCAA | ATACAT |
| ATATAA | AAAATA |
| AATCAA | ATTAAA** |
| ATACTA | AATTAA** |
| ATAAAA | AATACA** |
| ATGAAA | CATAAA** |

*indicates a potential major plant polyadenylation site.
**indicates a potential minor animal polyadenylation site.
All others are potential minor plant polyadenylation sites.

The regions for mutagenesis may be selected in the following manner. All regions of the DNA sequence of the cry gene are identified which contained five or more consecutive base pairs which were A or T. These were ranked in terms of length and highest percentage of A+T in the surrounding sequence over a 20-30 base pair region. The DNA is analysed for regions which might contain polyadenylation sites or ATTTA sequences. Oligonucleotides are then designed which maximize the elimination of A+T consecutive regions which contained one or more polyadenylation sites or ATTTA sequences. Two potential plant polyadenylation sites have been shown to be more critical based on published reports. Codons are selected which increase G+C content, but do not generate restriction sites for enzymes useful for cloning and assembly of the modified gene (e.g., BamHI, BglII, SacI, NcoI, EcoRV, etc.). Likewise condons are avoided which contain the doublets TA or GC which have been reported to be infrequently-found codons in plants.

Although the CaMV35S promoter is generally a high level constitutive promoter in most plant tissues, the expression level of genes driven the CaMV35S promoter is low in floral tissue relative to the levels seen in leaf tissue. Because the economically important targets damaged by some insects are the floral parts or derived from floral parts (e.g., cotton squares and bolls, tobacco buds, tomato buds and fruit), it is often advantageous to increase the expression of crystal proteins in these tissues over that obtained with the CaMV35S promoter.

The 35S promoter of Figwort Mosaic Virus (FMV) is analogous to the CaMV35S promoter. This promoter has been isolated and engineered into a plant transformation vector. Relative to the CaMV promoter, the FMV 35S promoter is highly expressed in the floral tissue, while still providing similar high levels of gene expression in other tissues such as leaf. A plant transformation vector, may be constructed in which one or more full-length native or plantized δ-endotoxin-encoding genes is driven by the FMV 35S promoter. For example, tobacco plants may be transformed with such a vector and compared for expression of the crystal protein(s) by Western blot or ELISA immunoassay in leaf and/or floral tissue. The FMV promoter has been used to produce relatively high levels of crystal protein in floral tissue compared to the CaMV promoter.

5.26 Example 26

Expression of Native or Plantized Cry Genes with ssRUBISCO Promoters and Chloroplast Transit Peptides The genes in plants encoding the small subunit of RUBISCO (SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an $NH_2$-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of heterologous genes in plants. Some SSU promoters are very highly expressed and could give rise to expression levels as high or higher than those observed with the CaMV35S promoter. The tissue distribution of expression from SSU promoters is different from that of the CaMV35S promoter, so for control of some insect pests, it may be advantageous to direct the expression of crystal proteins to those cells in which SSU is most highly expressed. For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express the protein of the present invention in only a subset of plant tissues, if for example expression of such a protein in certain cells was found to be deleterious to those cells. For example, for control of Colorado potato beetle in potato, it may be advantageous to use SSU promoters to direct crystal protein expression to the leaves but not to the edible tubers.

Utilizing SSU CTP sequences to localize crystal proteins to the chloroplast might also be advantageous. Localization of the *B. thuringiensis* crystal proteins to the chloroplast could protect these from proteases found in the cytoplasm. This could stabilize the proteins and lead to higher levels of accumulation of active toxin. cry genes containing the CTP may be used in combination with the SSU promoter or with other promoters such as CaMV35S.

5.27 Example 27

Targeting of δ-Endotoxin Polypeptides to the Extracellular Space or Vacuole Using Signal Peptides The *B. thuringiensis* δ-endotoxin polypeptides described herein may primarily be localized to the cytoplasm of transformed plant cell, and this cytoplasmic localization may result in plants that are insecticidally-resistant. However, in certain embodiments, it may be advantageous to direct the localization or production of the *B. thuringiensis* polypeptide(s) to one or more compartments of a plant, or to particular types of plant cells. Localizing *B. thuringiensis* proteins in compartments other than the cytoplasm may result in less exposure of the *B. thuringiensis* proteins to cytoplasmic proteases leading to greater accumulation of the protein yielding enhanced insecticidal activity. Extracellular localization could lead to more efficient exposure of certain insects to the *B. thuringiensis* proteins leading to greater efficacy. If a *B. thuringiensis* protein were found to be deleterious to plant cell function, then localization to a noncytoplasmic compartment could protect these cells from the toxicity of the protein.

In plants as well as other eukaryotes, proteins that are destined to be localized either extracellularly or in several specific compartments are typically synthesized with an $NH_2$-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion into the endoplasmic reticulum with cleavage of the signal peptide occurring at this stage. The mature protein then passes through the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasm of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct *B. thuringiensis* proteins out of the cytoplasm is to fuse the genes for synthetic *B. thuringiensis* genes to DNA sequences encoding known plant signal peptides. These fusion genes will give rise to *B. thuringiensis* proteins that enter the secretory pathway, and lead to extracellular secretion or targeting to the vacuole or other compartments.

Signal sequences for several plant genes have been described. One such sequence is for the tobacco pathogenesis related protein PR1b has been previously described (Cornelissen et al., 1986). The PR1b protein is normally localized to the extracellular space. Another type of signal peptide is contained on seed storage proteins of legumes. These proteins are localized to the protein body of seeds, which is a vacuole like compartment found in seeds. A signal peptide DNA sequence for the β-subunit of the 7S storage protein of common bean (*Phaseolus vulgaris*), PvuB has been described (Doyle et al., 1986). Based on the published these published sequences, genes may be synthesized chemically using oligonucleotides that encode the signal peptides for PR1b and PvuB. In some cases to achieve secretion or compartmentalization of heterologous proteins, it may be necessary to include some amino acid sequence beyond the normal cleavage site of the signal peptide. This may be necessary to insure proper cleavage of the signal peptide.

6.0 REFERENCES

The following references, to the extent that they provide exemplary procedural or other details supplementary to those set forth herein, are specifically incorporated herein by reference:

U.S. Pat. No. 4,196,265, issued Apr. 1, 1980.
U.S. Pat. No. 4,237,224, issued Dec. 2, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,766,203, issued Aug. 23, 1988.
U.S. Pat. No. 4,769,061, issued Sep. 6, 1988.
U.S. Pat. No. 4,800,159, issued Jan. 24, 1989.
U.S. Pat. No. 4,883,750, issued Nov. 28, 1989.
U.S. Pat. No. 4,940,835, issued Feb. 23, 1990.
U.S. Pat. No. 4,943,674, issued Jul. 24, 1990.
U.S. Pat. No. 4,965,188, issued Oct. 23, 1990.
U.S. Pat. No. 4,971,908, issued Nov. 20, 1990.
U.S. Pat. No. 4,987,071, issued Jan. 22, 1991.
U.S. Pat. No. 5,023,179, issued Jun. 11, 1991.
U.S. Pat. No. 5,097,025, issued Mar. 17, 1992.
U.S. Pat. No. 5,106,739, issued Apr. 21, 1992.
U.S. Pat. No. 5,110,732, issued May 5, 1992.
U.S. Pat. No. 5,139,954, issued Aug. 19, 1992.
U.S. Pat. No. 5,176,995, issued Oct. 15, 1991.
U.S. Pat. No. 5,177,011, issued Jan. 5, 1993.
U.S. Pat. No. 5,187,091, issued Oct. 15, 1991.
U.S. Pat. No. 5,334,711, issued Aug. 2, 1994.
U.S. Pat. No. 5,378,619, issued Jan. 3, 1995.
U.S. Pat. No. 5,384,253, issued Jan. 24, 1995.
U.S. Pat. No. 5,401,836, issued Mar. 28, 1995.
U.S. Pat. No. 5,424,412, issued Jun. 13, 1995.
U.S. Pat. No. 5,436,002, issued Jul. 25, 1995.
U.S. Pat. No. 5,436,393, issued Jul. 25, 1995.
U.S. Pat. No. 5,442,052, issued Aug. 15, 1995.
U.S. Pat. No. 5,447,858, issued Sep. 5, 1995.
U.S. Pat. No. 5,459,252, issued Oct. 17, 1995.

U.S. Pat. No. 5,463,175, issued Oct. 31, 1995.
U.S. Pat. No. 5,491,288, issued Feb. 13, 1996.
U.S. Pat. No. 5,504,200, issued Apr. 2, 1996.
U.S. Pat. No. 5,530,196, issued Jun. 25, 1996.
U.S. Pat. No. 5,538,879, issued Jul. 23, 1996.
U.S. Pat. No. 5,576,198, issued Nov. 19, 1996.
U.S. Pat. No. 5,589,583, issued Dec. 31, 1996.
U.S. Pat. No. 5,589,610, issued Dec. 31, 1996.
U.S. Pat. No. 5,589,614, issued Dec. 31, 1996
U.S. Pat. No. 5,595,896, issued Jan. 21, 1997.
U.S. Pat. No. 5,608,144, issued Mar. 4, 1997.
U.S. Pat. No. 5,614,399, issued Mar. 25, 1997.
U.S. Pat. No. 5,631,359, issued May 20, 1997.
U.S. Pat. No. 5,633,363, issued May 27, 1997.
U.S. Pat. No. 5,633,439, issued May 27, 1997.
U.S. Pat. No. 5,633,440, issued May 27, 1997.
U.S. Pat. No. 5,633,441, issued May 27, 1997.
U.S. Pat. No. 5,646,333, issued Jul. 8, 1997.
U.S. Pat. No. 5,659,124, issued Aug. 19, 1997.
U.S. Pat. No. 5,689,040, issued Nov. 18, 1997.
U.S. Pat. No. 5,689,049, issued Nov. 18, 1997.
U.S. Pat. No. 5,689,051, issued Nov. 18, 1997.
U.S. Pat. No. 5,689,056, issued Nov. 18, 1997.
U.S. Pat. No. 5,700,922, issued Dec. 23, 1997.
U.S. Pat. No. 5,712,112, issued Jan. 27, 1998.
Int. Pat. Appl. Publ. No. PCT/US87/00880.
Int. Pat. Appl. Publ. No. PCT/US89/01025.
Int. Pat. Appl. Publ. No. WO 88/10315.
Int. Pat. Appl. Publ. No. WO 89/06700.
Int. Pat. Appl. Publ. No. WO 90/13651.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Int. Pat. Appl. Publ. No. WO 96/10083.
Int. Pat. Appl. Publ. No. WO 97/17507.
Int. Pat. Appl. Publ. No. WO 97/17600.
Int. Pat. Appl. Publ. No. WO 97/40162.
Eur. Pat. Appl. Publ. No. EP0120516.
Eur. Pat. Appl. Publ. No. EP0360257.
Eur. Pat. Appl. Publ. No. EP 320,308.
Eur. Pat. Appl. Publ. No. EP 329,822.
Eur. Pat. Appl. Publ. No. 92110298.4
Great Britain Pat. Appl. Publ. No. GB 2,202,328.
Abdullah et al., *Biotechnology*, 4:1087, 1986.
Abbott, "A method for computing the effectiveness of an insecticide," *J. Econ. Entomol.*, 18:265-267, 1925.
Altschul, Stephen F. et al., "Gapped BLAST and PSI-BLAST: a new generation of protein database search programs", *Nucl. Acids Res.* 25:3389-3402, 1997.
Arantes and Lereclus, *Gene*, 108:115-119, 1991.
Armitage et al., *Proc. Natl. Acad. Sci. USA*, 94(23):12320-12325, 1997.
Baumlein, Boerjan, Nagy, Panitz, Inze, Wobus, "Upstream sequences regulating legumin gene expression in heterologous transgenic plants," *Mol. Gen. Genet.*, 225(1):121-128, 1991.
Baum, et al., *Appl. Envior. Biol.* 56:3420-3428, 1990.
Baumann et al., *J. Bacteriol.*, 170:2045-2050, 1988.
Benbrook et al., *In: Proceedings Bio Expo* 1986, Butterworth, Stoneham, Mass., pp. 27-54, 1986.
Berna and Bernier, "Regulated expression of a wheat germin gene in tobacco: oxalate oxidase activity and apoplastic localization of the heterologous protein," *Plant Mol. Biol.*, 33(3):417-429, 1997.
Bevan et al., *Nucleic Acids Res.*, 11(2):369-85, 1983.
Boffa, Carpaneto, Allfrey, *Proc. Natl. Acad. Sci. USA*, 92:1901-1905, 1995.
Boffa, Morris, Carpaneto, Louissaint, Allfrey, *J. Biol. Chem.*, 271:13228-13233, 1996.
Boronat, Martinez, Reina, Puigdomenech, Palau, "Isolation and sequencing of a 28 kd gluteline-2 gene from maize: Common elements in the 5' flanking regions among zein and glutelin genes," *Plant Sci.*, 47:95-102, 1986.
Brussock and Currier, "Use of sodium dodecyl sulfate-polacryamide gel electrophoresis to quantify *Bacillus thuringiensis* δ-endotoxins," *In: Analytical Chemistry of Bacillus thuringiensis*, L. A. Hickle and W. L. Fitch, (Eds), American Chemical Society, Washington D.C., pp. 78-87, 1990.
Bytebier et al., *Proc. Natl. Acad. Sci. USA*, 84:5345, 1987.
Callis et al., *Genes and Development*, 1:1183, 1987.
Callis, Fromm, Walbot, "Introns increase gene expression in cultured maize cells," *Genes Devel.*, 1:1183-1200, 1987.
Campbell, "Monoclonal Antibody Technology, Laboratory Techniques in Biochemistry and Molecular Biology," Vol. 13, Burden and Von Knippenberg, Eds. pp. 75-83, Elsevier, Amsterdam, 1984.
Capecchi, "High efficiency transformation by direct microinjection of DNA into cultured mammalian cells," *Cell*, 22(2):479-488, 1980.
Carlsson et al., *Nature*, 380:207, 1996.
Carlton and Gonzalez, *Molecular Biology of Microbial Differnetiation*, Ninth International Spore Conference, Asilomar, Calif., USA Sep. 3-6, 1984. IX+280P. American Society for Microbiology, 246-252, 1985.
Cashmore et al., *Gen. Eng. of Plants*, Plenum Press, New York, 29-38, 1983.
Charles et al., *Zent. Bakteriol. Suppl.*, 28(0):99-100, 1996a.
Charles et al., *Annual Review of Entomology*, 41:451-472, 1996b.
Chau et al., *Science*, 244:174-181, 1989.
Chen et al., *Nucl. Acids Res.*, 20:4581-9, 1992.
Cheng, Sardana, Kaplan, Altosaar, "*Agrobacterium*-transformed rice plants expressing synthetic cryIA(b) and cryIA(c) genes are highly toxic to striped stem borer and yellow stem borer," *Proc. Natl. Acad. Sci. USA*, 95(6):2767-2772, 1998.
Chowrira and Burke, *Nucl. Acids Res.*, 20:2835-2840, 1992.
Christensen et al., *J. Pept. Sci.*, 1(3):175-183, 1995.
Christensen, Sharrock, Quail, "Maize polyubiquitin genes: Structure, thermal perturbation of expression and transcript splicing, and promoter activity following transfer to protoplasts by electroporation," *Plant Mol. Biol.*, 18:675-689, 1992.
Clapp, "Somatic gene therapy into hematopoietic cells. Current status and future implications," *Clin. Perinatol.*, 20(1):155-168, 1993.
Collins and Olive, *Biochem.*, 32:2795-2799, 1993.
Conway and Wickens, *In: RNA Processing*, p. 40, Cold Spring Harbor Laboratory, Cold Spring Harbor, N.Y., 1988.
Corey, *Trends Biotechnol.*, 15(6):224-229, 1997.
Cornelissen et al., *Nature*, 321(6069):531-2, 1986.
Crickmore et al., "Revision of the nomenclature for the *Bacillus thuringiensis* pesticidal crystal proteins," *Proc. Natl. Acad Sci USA* 62:807-813, 1998
Cristou et al., *Plant Physiol.*, 87:671-674, 1988.
Curiel, Agarwal, Wagner, Cotten, "Adenovirus enhancement of transferrin-polylysine-mediated gene delivery," *Proc. Natl. Acad. Sci. USA*, 88(19):8850-8854, 1991.

Curiel, Wagner, Cotten, Birnstiel, Agarwal, Li, Loechel, and Hu, "High-efficiency gene transfer mediated by adenovirus coupled to DNA-polylysine complexes," *Hum. Gen. Ther.*, 3(2):147-154, 1992.

Daum, "Revision of two computer programs for probit analysis," *Bull. Entomol. Soc. Amer.*, 16:10-15, 1970.

Dean et al., *Nucl. Acids Res.*, 14(5):2229, 1986.

Dennis, Gerlach, Pryor, Bennetzen, Inglis, Llewellyn, Sachs, Ferl, Peackocock, "Molecular analysis of the alcohol dehydrogenase (Adh1) gene of maize," *Nucl. Acids Res.*, 12:3983-4000, 1984.

Diehn et al., *Genet. Eng.* (N.Y.), 18:83-99, 1996.

Dhir, Dhir, Hepburn, Widholm, "Factors affecting transient gene expression in electroporated *Glycine-max* protoplasts," *Plant Cell Rep.*, 10(2):106-110, 1991a.

Donovan et al., *Appl. Environ. Microbiol.*, 58:3921-3927, 1992.

Doyle et al., *J. Biol. Chem.*, 261(20):9228-38, 1986.

Dropulic et al., *J. Virol.*, 66:1432-41, 1992.

Dueholm et al., *J. Org. Chem.*, 59:5767-5773, 1994.

Egholm et al., *Nature*, 365:566-568, 1993.

Eglitis and Anderson, "Retroviral vectors for introduction of genes into mammalian cells," *Biotechniques*, 6(7):608-614, 1988.

Eglitis, Kantoff, Kohn, Karson, Moen, Lothrop, Blaese, Anderson, "Retroviral-mediated gene transfer into hemopoietic cells," *Avd. Exp. Med. Biol.*, 241:19-27, 1988.

Elroy-Stein and Moss, *Proc. Natl. Acad. Sci. USA*, 87:6743-7, 1990.

English and Slatin, *Insect Biochem. Mol. Biol.*, 22:1-7, 1992.

Faktor, Kooter, Dixon, Lamb, "Functional dissection of a bean chalcone synthase gene promoter in transgenic tobacco plants reveals sequence motifs essential for floral expression," *Plant Mol. Biol.*, 32(5):849-859, 1996.

Ficker, Kirch, Eijlander, Jacobsen, Thompson, "Multiple elements of the S2-RNase promoter from potato (*Solanum tuberosum* L.) are required for cell type-specific expression in transgenic potato and tobacco," *Mol. Gen. Genet.*, 257(2):132-142, 1998.

Footer, Engholm, Kron, Coull, Matsudaira, *Biochemistry*, 35:10673-10679, 1996.

Fraley et al., *Biotechnology*, 3:629, 1985.

Fraley et al., *Proc. Natl. Acad. Sci. USA*, 80:4803, 1983.

French, Janda, Ahlquist, "Bacterial gene inserted in an engineered RNA virus: efficient expression in monocotyledonous plant cells," *Science*, 231:1294-1297, 1986.

Frohman, *In: PCR™ Protocols: A Guide to Methods and Applications*, Academic Press, New York, 1990.

Fromm et al., *Biotechnology* (*N.Y.*), 8(9):833-9, 1990.

Fromm, Taylor, Walbot, "Expression of genes transferred into monocot and dicot plant cells by electroporation," *Proc. Natl. Acad. Sci. USA*, 82(17):5824-5828, 1985.

Fromm et al., *Nature*, 319:791-793, 1986.

Fujimura et al., *Plant. Tiss. Cult. Lett.*, 2:74, 1985.

Fynan, Webster, Fuller, Haynes, Santoro, Robinson, "DNA vaccines: protective immunizations by parenteral, mucosal, and gene gun inoculations," *Proc. Natl. Acad. Sci. USA*, 90(24):11478-11482, 1993.

Gallie and Young, "The regulation of expression in transformed maize aleurone and endosperm protoplasts," *Plant Physiol.*, 106:929-939, 1994.

Gallie, Feder, Schimke, Walbot, "Post-transcriptional regulation in higher eukaryotes: the role of the reporter gene in controlling expression," *Mol. Gen. Genet.*, 228:258-264, 1991.

Gallie, Lucas, Walbot, "Visualizing mRNA expression in plant protoplasts: factors influencing efficient mRNA uptake and translation," *Plant Cell*, 1:301-311, 1989.

Gallie, Sleat, Turner, Wilson, "Mutational analysis of the tobacco mosaic virus 5'-leader for altered ability to enhance translation," *Nucl. Acids Res.*, 16:883-893, 1988.

Gallie, Sleat, Watts, Turner, Wilson, "A comparison of eukaryotic viral 5'-leader sequences as enhancers of mRNA expression in vivo," *Nucl. Acids Res.*, 15:8693-8711, 1987b.

Gallie, Sleat, Watts, Turner, Wilson, "The 5'-leader sequence of tobacco mosaic virus RNA enhances the expression of foreign gene transcripts in vitro and in vivo," *Nucl. Acids Res.*, 15:3257-3273, 1987a.

Gambacorti-Passerini et al., *Blood*, 88:1411-1417, 1996.

Gao and Huang, *Nucl. Acids Res.*, 21:2867-72, 1993.

Gefter et al., *Somat. Cell Genet.*, 3:231-236, 1977.

Gehrke, Auron, Quigley, Rich, Sonenberg, "5'-Conformation of capped alfalfa mosaic virus ribonucleic acid 4 may reflect its independence of the cap structure or of cap-binding protein for efficient translation," *Biochemistry*, 22:5157-5164, 1983.

Genovese and Milcarek, *In: RNA Processing*, p. 62, Cold Spring Harbor Laboratory, Cold Spring Harbor, N.Y., 1988.

Gil and Proudfoot, *Nature*, 312:473, 1984.

Goding, "Monoclonal Antibodies: Principles and Practice," pp. 60-74. 2nd Edition, Academic Press, Orlando, Fla., 1986.

Goelet, Lomonossoff, Butler, Akam, Gait, Karn, "Nucleotide sequence of tobacco mosaic virus RNA," *Proc. Natl. Acad. Sci. USA*, 79:5818-5822, 1982.

Gonzalez Jr. et al., *Proc. Natl. Acad. Sci USA*, 79:6951-6955, 1982.

Good and Nielsen, *Antisense Nucleic Acid Drug Dev.*, 7(4):431-437, 1997.

Graham, Craig, Waterhouse, "Expression patterns of vascular-specific promoters ROIC and Sh in transgenic potatoes and their use in engineering PLRV-resistant plants," *Plant Mol. Biol.*, 33(4):729-735, 1997.

Graham, F. L., and van der Eb, A. J., "Transformation of rat cells by DNA of human adenovirus 5," *Virology*, 54(2):536-539, 1973.

Griffith et al., *J. Am. Chem. Soc.*, 117:831-832, 1995.

Grosset, Alary, Gautier, Menossi, Martinez-Izquierdo, Joudrier, "Characterization of a barley gene coding for an alpha-amylase inhibitor subunit (Cmd protein) and analysis of its promoter in transgenic tobacco plants and in maize kernels by microprojectile bombardment," *Plant Mol. Biol.*, 34(2):331-338, 1997.

Guerrier-Takada et al., *Cell*, 35:849, 1983.

Haaima, Lohse, Buchardt, Nielsen, *Angew. Chem., Int. Ed. Engl.*, 35:1939-1942, 1996.

Hampel and Tritz, *Biochem.*, 28:4929, 1989.

Hampel et al., *Nucl. Acids Res.*, 18:299, 1990.

Hanvey et al., *Science*, 258:1481-1485, 1992.

Harlow and Lane, "Antibodies: A Laboratory Manual," Cold Spring Harbor Laboratory, Cold Spring Harbor, N.Y., 1988.

Herrera-Estrella et al., *Embo. J.*, 2(6):987-996, 1983.

Hertig et al., *Plant Mol. Biol.*, 16(1):171-4, 1991.

Hess, *Intern Rev. Cytol.*, 107:367, 1987.

Höfte and Whiteley, *Microbiol. Rev.*, 53:242-255, 1989.

Horsch, Fry, Hoffmann, Eichholtz, Rogers, Fraley, "A simple and general method for transferring genes into plants," *Science*, 227(4691):1229-1231, 1985.

Huang, An, McDowell, McKinney, Meagher, "The *Arabidopsis* ACT11 action gene is strongly expressed in tissues of the emerging inflorescence, pollen and developing ovules," *Plant Mol. Biol*., 33(1):125-139, 1997.

Hudspeth and Grula, "Structure and expression of the maize gene encoding the phosphoenolpyruvate carboxylase isozyme involved in C4 photosynthesis," *Plant Mol. Biol*., 12:579-589, 1989.

Hyrup and Nielsen, *Bioorg. Med. Chem*., 1996.

Ingelbrecht, Herman, Dekeyser, Van Montagu, Depicker, "Different 3' end regions strongly influence the level of gene expression in plant cells," *Plant Cell,* 1:671-680, 1989.

Jameson and Wolf, "The Antigenic Index: A Novel Algorithm for Predicting Antigenic Determinants," *Compu. Appl. Biosci*., 4(1):181-6, 1988.

Jensen et al., *Biochemistry,* 36(16):5072-5077, 1997.

Jobling and Gehrke, "Enhanced translation of chimaeric messenger RNAs containing a plant viral untranslated leader sequence," *Nature,* 325:622-625, 1987.

Johnston and Tang, "Gene gun transfection of animal cells and genetic immunization," *Methods Cell. Biol*., 43(A):353-365, 1994.

Jones, Dean, Gidoni, Gilbert, Bond-Nutter, Lee, Bedbrook, Dunsmuir, "Expression of bacterial chitinase protein in tobacco leaves using two photosynthetic gene promoters," *Mol. Gen. Genet*., 212:536-542, 1988.

Jorgensen et al., *Mol. Gen. Genet*., 207:471, 1987.

Joshi, "An inspection of the domain between putative TATA box and translation start site in 79 plant genes," *Nucl. Acids Res*., 15:6643-6653, 1987.

Kaiser and Kezdy, *Science,* 223:249-255, 1984.

Kashani-Sabet et al., *Antisense Res. Dev*., 2:3-15, 1992.

Keller et al., *EMBO J*., 8:1309-14, 1989.

Klee, Yanofsky, Nester, "Vectors for transformation of higher plants," *Bio-Technology,* 3(7):637-642, 1985.

Klein et al., *Nature,* 327:70, 1987.

Klein et al., *Proc. Natl. Acad. Sci. USA,* 85:8502-8505, 1988.

Koch et al., *Tetrahedron Lett*., 36:6933-6936, 1995.

Kohler and Milstein, *Eur. J. Immunol*., 6:511-519, 1976.

Kohler and Milstein, *Nature,* 256:495-497, 1975.

Koppelhus, *Nucleic Acids Res*., 25(11):2167-2173, 1997.

Korn and Queen, *DNA,* 3:421-436, 1984.

Koziel, Beland, Bowman, Carozzi, Crenshaw, Crossland, Dawson, Desai, Hill, Kadwell, Launis, Lewis, Maddox, McPherson, Meghji, Merlin, Rhodes, Warren, Wright, Evola, "Field performance of elite transgenic maize plants expressing an insecticidal protein derived from *Bacillus thuringiensis, Bio/technology,* 11:194-200, 1993.

Koziel, Carozzi, Desai, "Optimizing expression of transgenes with an emphasis on post-transcriptional events," *Plant Mol. Biol*., 32(102):393-405, 1996.

Kremsky et al., *Tetrahedron Lett*., 37:4313-4316, 1996.

Krieg et al., *In: Zangew. Ent*., 96:500-508, 1983.

Kuby, "Immunology" 2nd Edition. W. H. Freeman & Company, New York, 1994.

Kunkel, Roberts, Zakour, "Rapid and efficient site-specific mutagenesis without phenotypic selection," *Methods Enzymol*., 154:367-382, 1987.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA,* 86(4):1173-1177, 1989.

Kyozuka, Fujimoto, Izawa, Shimamoto, "Anaerobic induction and tissue-specific expression of maize Adh1 promoter in transgenic rice plants and their progeny," *Mol. Gen. Genet*., 228(1-2):40-48, 1991.

Kyte and Doolittle, "A simple method for displaying the hydropathic character of a protein," *J. Mol. Biol*., 157(1):105-132, 1982.

L'Huillier et al., *EMBO J*., 11:4411-8, 1992.

Lambert et al., *Appl. Environ. Microbiol*., 58:2536-2642, 1992b.

Lambert et al., *Gene,* 110:131-132, 1992a.

Landsdorp et al., *Hum. Mol. Genet*., 5:685-691, 1996.

Langridge et al., *Proc. Natl. Acad. Sci. USA,* 86:3219-3223, 1989.

Lieber et al., *Methods Enzymol*., 217:47-66, 1993.

Lindstrom et al., *Developmental Genetics,* 11:160, 1990.

Lisziewicz et al., *Proc. Natl. Acad. Sci. U.S.A*., 90:8000-4, 1993.

Lorz et al., *Mol. Gen. Genet*., 199:178, 1985.

Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med.,* 178(6):2089-2096, 1993.

Luehrsen et al., *Prog. Nucleic Acid Res. Mol. Biol*., 47:149-93, 1994.

Luehrsen and Walbot, "Intron enhancement of gene expression and the splicing efficiency of introns in maize cells," *Mol. Gen. Genet*., 225:81-93, 1991.

Luo et al., *Plant Mol. Biol. Reporter,* 6:165, 1988.

Lutcke, Chow, Mickel, Moss, Kern, Scheele, "Selection of AUG initiation codons differs in plants and animals," *EMBO J*., 6:43-48, 1987.

Maas, Laufs, Grant, Korfhage, Werr, "The combination of a novel stimulatory element in the first exon of the maize shrunken-1 gene with the following intron enhances reporter gene expression 1000-fold," *Plant Mol. Biol*., 16:199-207, 1991.

Macaluso and Mettus, *J. Bacteriol*., 173:1353-1356, 1991.

Maddock et al., *Third International Congress of Plant Molecular Biology*, Abstract 372, 1991.

Maloy, "Experimental Techniques in Bacterial Genetics" Jones and Bartlett Publishers, Boston, Mass., 1990.

Maloy et al., "Microbial Genetics" 2nd Edition. Jones and Barlett Publishers, Boston, Mass., 1994.

Maniatis et al., "Molecular Cloning: a Laboratory Manual," Cold Spring Harbor Laboratory, Cold Spring Harbor, N.Y., 1982.

Marcotte et al., *Nature,* 335:454, 1988.

Marrone, "Influence of artificial diet on southern corn rootworm life history and susceptibility to insecticidal compounds," *Westview Studies in Insect Biology; Advances in insect rearing for research and pest management,* 229-235, 1992.

Mascerenhas, Mettler, Pierce, Lowe, "Intron mediated enhancement of heterologous gene expression in maize," *Plant Mol. Biol*., 15:913-920, 1990.

McBride, Svab, Schaaf, Hogan, Stalker, Maliga, "Amplification of a chimeric *Bacillus* gene in chloroplasts leads to an extraordinary level of an insecticidal protein in tobacco," *Bio/technology,* 13:362-365, 1995.

McCabe et al., *Biotechnology,* 6:923, 1988.

McDevitt et al., *Cell,* 37:993-999, 1984.

McElroy, Zhang, Wu, "Isolation of an efficient promoter for use in rice transformation," *Plant Cell,* 2:163-171, 1990.

Michael, *Biotechniques,* 16:410-412, 1994.

Mollegaard, Buchardt, Egholm, Nielsen, *Proc. Natl. Acad. Sci. USA,* 91:3892-3895, 1994.

Nawrath, Poirier, Somerville, "Targeting of the polyhydroxybutyrate biosynthetic pathway to the plastids of *Arabidopsis thaliana* results in high levels of polymer accumulation," *Proc. Natl. Acad. Sci. USA,* 91:12760-12764, 1994.

Neilsen, *In: Perspectives in Drug Discovery and Design* 4, Escom Science Publishers, pp. 76-84, 1996.

Nielsen et al., *Anticancer Drug Des*., 8(1):53-63, 1993b.

Nielsen, Egholm, Berg, Buchardt, *Science,* 254:1497-1500, 1991.

Norton, Piatyszek, Wright, Shay, Corey, *Nat. Biotechnol*., 14:615-620, 1996.

Norton, Waggenspack, Varnum, Corey, *Bioorg. Med. Chem*., 3:437-445, 1995.

Oard, Paige, Dvorak, "Chimeric gene expression using maize intron in cultured cells of breadwheat," *Plant Cell. Rep*., 8:156-160, 1989.

Odell et al., *Nature,* 313:810, 1985.

Ohara et al., *Proc. Natl. Acad. Sci. U.S.A*., 86(15):5673-7, 1989.

Ohkawa, Yuyama, Taira, "Activities of HIV-RNA targeted ribozymes transcribed from a 'shot-gun' type ribozyme-trimming plasmid," *Nucl. Acids Symp. Ser*., 27:15-6, 1992.

Ojwang et al., *Proc. Natl. Acad. Sci. USA,* 89:10802-6, 1992.

Omirulleh et al., *Plant Mol. Biol*., 21:415-428, 1993.

Orum, Nielsen, Egholm, Berg, Buchardt, Stanley, *Nucl. Acids Res*., 21:5332-5336, 1993.

Orum, Nielsen, Jorgensen, Larsson, Stanley, Koch, *BioTechniques,* 19:472-480, 1995.

Pandey and Marzluff, In "RNA Processing," p. 133, Cold Spring Harbor Laboratory, Cold Spring Harbor, N.Y., 1987.

Pardridge, Boado, Kang, *Proc. Natl. Acad. Sci. USA,* 92:5592-5596, 1995.

Pearson and Lipman, *Proc. Natl. Acad Sci USA,* 85(8): 2444-8, 1988.

Pena et al., *Nature,* 325:274, 1987.

Perlak, Deaton, Armstrong, Fuchs, Sims, Greenplate, Fischhoff, "Insect resistant cotton plants," *Bio/Technology,* 8:939-943, 1990.

Perlak, Fuchs, Dean, McPherson, Fischhoff, "Modification of the coding sequence enhances plant expression of insect control protein genes," *Proc. Natl. Acad. Sci. USA,* 88:3324-3328, 1991.

Perlak, Stone, Muskopf, Peterson, Parker, McPherson, Wyman, Love, Reed, Biever, Fischhoff, "Genetically improved potatoes: protection from damage by Colorado potato beetles," *Plant Mol. Biol*., 22:313-321, 1993.

Perrault et al., *Nature,* 344:565, 1990.

Perrotta and Been, *Biochem*., 31:16, 1992.

Perry-O'Keefe, Yao, Coull, Fuchs, Egholm, *Proc. Natl. Acad. Sci. USA,* 93:14670-14675, 1996.

Petersen, Jensen, Egholm, Nielsen, Buchardt, *Bioorg. Med. Chem. Lett*., 5:1119-1124, 1995.

Pieken et al., *Science,* 253:314, 1991.

Poogin and Skryabin, "The 5' untranslated leader sequence of potato virus X RNA enhances the expression of the heterologous gene in vivo," *Mol. Gen. Genet.,* 234:329-331, 1992.

Poszkowski et al., *EMBO J*., 3:2719, 1989.

Potrykus et al., *Mol. Gen. Genet*., 199:183, 1985.

Poulsen et al., *Mol. Gen. Genet*., 205:193-200, 1986.

Prokop and Bajpai, *Ann. N.Y. Acad. Sci*., 646, 1991.

Rogers et al., *In: Methods For Plant Molecular Biology*, Weissbach and Weissbach, eds., Academic Press Inc., San Diego, Calif. 1988.

Rogers et al., *Methods Enzymol*., 153:253-277, 1987.

Rose, *Anal. Chem*., 65(24):3545-3549, 1993.

Rossi et al., *Aids Res. Hum. Retrovir*., 8:183, 1992.

Ruskowski et al., *Cancer,* 80(12 Suppl):2699-2705, 1997.

Russell and Fromm, "Tissue-specific expression in transgenic maize for four endosperm promoters from maize and rice," *Transgenic Res*., 6(2):157-168, 1997.

Sadofsky and Alwine, *Mol. Cell. Biol*., 4(8):1460-1468, 1984.

Sambrook et al., "Antibodies: A Laboratory Manual," Cold Spring Harbor Laboratory, Cold spring Harbor, N.Y., 1989a.

Sambrook et al., "Molecular Cloning: A Laboratory Manual," Cold Spring Harbor Laboratory, Cold Spring Harbor, N.Y., 1989b.

Sanger et al., "DNA sequencing with chain-terminating inhibitors," *Proc. Natl. Acad. Sci. USA,* 74(12):5463-5467, 1977.

Sarver et al., *Science,* 247(4947):1222-5, 1990.

Saville and Collins, *Cell,* 61:685-696, 1990.

Saville and Collins, *Proc. Natl. Acad. Sci. USA,* 88:8826-8830, 1991.

Scanlon et al., *Proc. Natl. Acad. Sci. USA,* 88:10591-5, 1991.

Scaringe et al., *Nucl. Acids Res*., 18:5433-5441, 1990.

Seeger et al., *Biotechniques,* 23(3):512-517, 1997.

Segal, "Biochemical Calculations" 2nd Edition. John Wiley & Sons, New York, 1976.

Shaw and Kamen, *Cell,* 46:659-667, 1986.

Shaw and Kamen, In: "RNA Processing", p. 220, Cold Spring Harbor Laboratory, Cold Spring Harbor, N.Y., 1987.

Simpson, *Science,* 233:34, 1986.

Sleat, Gallie, Jefferson Bevan, Turner, Wilson, "Characterization of the 5'-leader sequence of tobacco mosaic virus RNA as a general enhancer of translation in vitro," *Gene,* 217:217-225, 1987.

Sleat, Hull, Turner, Wilson, "Studies on the mechanism of translational enhancement by the 5'-leader sequence of tobacco mosaic virus RNA," *Eur. J. Biochem*., 175:75-86, 1988.

Southern, *J. Mol. Biol*., 98:503-517, 1975.

Spielmann et al., *Mol. Gen. Genet*., 205:34, 1986.

Stetsenko, Lubyako, Potapov, Azhikina, Sverdlov, *Tetrahedron Lett*., 37:3571-3574, 1996.

Taira et al., *Nucl. Acids Res*., 19:5125-30, 1991.

Tanaka, Mita, Ohta, Kyozuka, Shimamoto, Nakamura, "Enhancement of foreign gene expression by a dicot intron in rice but not in tobacco is correlated with an increased level of mRNA and an efficient splicing of the intron," *Nucl. Acids Res.,* 18:6767-6770, 1990.

Thanabalu et al., *Appl. Environ. Microbiol*., 61(11):4031-6, 1995.

Thanabalu et al., *J. Bacteriol*., 173(9):2776-85, 1991.

Thiede, Bayerdorffer, Blasczyk, Wittig, Neubauer, *Nucleic Acids Res*., 24:983-984, 1996.

Thisted, Just, Petersen, Hyldig-Nielsen, Godtfredsen, *Cell Vision,* 3:358-363, 1996.

Thomson et al., *Tetrahedron,* 51:6179-6194, 1995.

Tomic, Sunjevaric, Savtchenko, Blumenberg, "A rapid and simple method for introducing specific mutations into any position of DNA leaving all other positions unaltered," *Nucl. Acids Res*., 18(6):1656, 1990.

Toriyama et al., *Theor Appl. Genet*., 73:16, 1986.

Treacy, Hattori, Prud'homme, Barbour, Boutilier, Baszczynski, Huang, Johnson, Miki, "Bnm1, a *Brassica* pollen-specific gene," *Plant Mol. Biol*., 34(4):603-611, 1997.

Uchimiya et al., *Mol. Gen. Genet*., 204:204, 1986.

Ulmann, Will, Breipohl, Langner, Ryte, *Angew. Chem., Int. Ed. Engl*., 35:2632-2635, 1996.

Upender, Raj, Weir, "Megaprimer method for in vitro mutagenesis using parallel templates," *Biotechniques,* 18:29-31, 1995.

Usman et al., *J. Am. Chem. Soc*., 109:7845-7854, 1987.

Usman and Cedergren, *TIBS,* 17:34, 1992.

Van Camp, Herouart, Willekens, Takahashi, Saito, Van Montagu, Inze, "Tissue-specific activity of two manganese superoxide dismutase promoters in transgenic tobacco," *Plant Physiol*., 112(2):525-535, 1996.

Van Tunen et al., *EMBO J*., 7:1257, 1988.

Vander, Van Montagu, Inze, Boerjan, "Tissue-specific expression conferred by the S-adenosyl-L-methionine synthetase promoter of *Arabidopsis thaliana* in transgenic poplar," *Plant Cell Physiol*., 37(8):1108-1115, 1996.

Vasil et al., "Herbicide-resistant fertile transgenic wheat plants obtained by microprojectile bombardment of regenerable embryogenic callus," *Biotechnology,* 10:667-674, 1992.

Vasil, *Biotechnology,* 6:397, 1988.

Vasil, Clancy, Ferl, Vasil, Hannah, "Increased gene expression by the first intron of maize shrunken-1 locus in grass species," *Plant Physiol*., 91:1575-1579, 1989.

Ventura et al., *Nucl. Acids Res*., 21:3249-55, 1993.

Veselkov, Demidov, Nielsen, Frank-Kamenetskii, *Nucl. Acids Res*., 24:2483-2487, 1996.

Vickers, Griffith, Ramasamy, Risen, Freier, *Nucl. Acids Res*., 23:3003-3008, 1995.

Vodkin et al., *Cell,* 34:1023, 1983.

Vogel, Dawe, Freeling, "Regulation of the cell type-specific expression of maize Adh1 and Sh1 electroporation-directed gene transfer into protoplasts of several maize tissues," *J. Cell. Biochem*., (Suppl. 0) 13:Part D, 1989.

Wagner et al., "Coupling of adenovirus to transferrin-polylysine/DNA complexes greatly enhances receptor-mediated gene delivery and expression of transfected genes," *Proc. Natl. Acad. Sci. USA,* 89(13):6099-6103, 1992.

Walker, Little, Nadeau, Shank, "Isothermal in vitro amplification of DNA by a restriction enzyme/DNA polymerase system," *Proc. Natl. Acad. Sci. USA,* 89(1):392-396, 1992.

Wang et al., *J. Am. Chem. Soc*., 118:7667-7670, 1996.

Watson, "Fluid and electrolyte disorders in cardiovascular patients," *Nurs. Clin. North Am*., 22(4):797-803, 1987.

Webb and Hurskainen, *J. Biomol. Screen*., 1:119-121, 1996.

Weerasinghe et al., *J. Virol*., 65:5531-4, 1991.

Weissbach and Weissbach, *Methods for Plant Molecular Biology*, (eds.), Academic Press, Inc., San Diego, Calif., 1988.

Wenzler et al., *Plant Mol. Biol*., 12:41-50, 1989.

Wickens and Stephenson, *Science*, 226:1045, 1984.

Wickens et al., In: "RNA Processing," p. 9, Cold Spring Harbor Laboratory, Cold Spring Harbor, N.Y., 1987.

Wilson, Flint, Deaton, Fischhoff, Perlak, Armstrong, Fuchs, Berberich, Parks, Stapp, "Resistance of cotton lines containing a *Bacillus thuringiensis* toxin to pink bollworm (Lepidopteran: Gelechiidae) and other insects," *J. Econ. Entomol.,* 4:1516-1521, 1992.

Wolf et al., *Compu. Appl. Biosci*., 4(1):187-911988.

Wong et al., *Plant Mol. Biol.* 20(1):81-93, 1992.

Wong and Neumann, "Electric field mediated gene transfer," *Biochim. Biophys. Res. Commun*., 107(2):584-587, 1982.

Woolf et al., *Proc. Natl. Acad. Sci. USA*, 89:7305-7309, 1992.

Wu et al., FEMS Microbiol. Lett., 81, 31-36, 1991.

Wu and Dean, "Functional significance of loops in the receptor binding domain of *Bacillus thuringiensis* CryIIIA delta-endotoxin," *J. Mol. Biol*., 255(4):628-640, 1996.

Yamada et al., *Plant Cell Rep*., 4:85, 1986.

Yang et al., *Proc. Natl. Acad. Sci. USA*, 87:4144-48, 1990.

Yanisch-Perron et al., *Gene*, 33(1):103-19, 1985.

Yin, Chen, Beachy, "Promoter elements required for phloem-specific gene expression from the RTBV promoter in rice," *Plant J*., 12(5):1179-1188, 1997b.

Yin, Zhu, Dai, Lamb, Beachy, "RF2a, a bZIP transcriptional activator of the phloem-specific rice tungro bacilliform virus promoter, functions in vascular development," *EMBO J*., 16(17):5247-5259, 1997a.

Yu et al., *Proc. Natl. Acad. Sci. USA*, 90:6340-4, 1993.

Zatloukal, Wagner, Cotten, Phillips, Plank, Steinlein, Curiel, Birnstiel, "Transferrinfection: a highly efficient way to express gene constructs in eukaryotic cells," *Ann. N.Y. Acad. Sci*., 660:136-153, 1992.

Zhou et al., *Methods Enzymol*., 101:433, 1983.

Zhou et al., *Mol. Cell Biol*., 10:4529-37, 1990.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An insecticidal polypeptide prepared by a process comprising the steps of:

(a) culturing *Bacillus thuringiensis* NRRL B-21915 or NRRL B-21916 cells under conditions effective to produce an insecticidal polypeptide having an amino acid sequence of SEQ ID NO:2 and SEQ ID NO:4; and (b) obtaining from said cells the insecticidal polypeptide so produced.

2. An isolated polypeptide comprising SEQ ID NO:2 and SEQ ID NO:4.

3. The polypeptide of claim 2, wherein the polypeptide is encoded by SEQ ID NO:1 and SEQ ID NO:3.

4. A composition comprising two or more polypeptides, wherein two of the polypeptides are SEQ ID NO:2 and SEQ ID NO:4.

5. The composition of claim 4, further comprising SEQ ID NO:19.

6. The composition of claim 4, comprising a cell extract, cell suspension, cell homogenate, cell lysate, cell supernatant, cell filtrate, or cell pellet of *Bacillus thuringiensis* NRRL B-21915 or NRRL B-21916 cells.

7. The composition of claim 6, wherein said composition is a powder, dust, pellet, granule, spray, emulsion, colloid, or solution.

8. The composition of claim 6, wherein said composition is prepared by desiccation, lyophilization, homogenization, extraction, filtration, centrifugation, sedimentation, or concentration of a culture of *Bacillus thuringiensis* cells.

9. The composition of claim 4, comprising from about 1% to about 99% by weight of said two or more polypeptides.

* * * * *

SEQUENCE LISTING

```
<160> NUMBER OF SEQ ID NOS: 34

<210> SEQ ID NO 1
<211> LENGTH: 1161
<212> TYPE: DNA
<213> ORGANISM: Bacillus thuringiensis

<400> SEQUENCE: 1
```

```
atgatagaaa ctaataagat atatgaaata agcaataaag ctaatggatt atatgcaact      60

acttatttaa gttttgataa ttcaggtgtt agtttattaa ataaaaatga atctgatatt     120

aatgattata atttgaaatg gtttttattt cctattgata ataatcagta tattattaca     180

agttatggag taaataaaaa taaggtttgg actgctaatg gtaataaaat aaatgttaca     240

acatattccg cagaaaattc agcacaacaa tggcaaataa gaaacagttc ttctggatat     300

ataatagaaa ataataatgg gaaaatttta acggcaggaa caggccaatc attaggttta     360

ttatatttaa ctgatgaaat acctgaagat tctaatcaac aatggaattt aacttcaata     420

caaacaattt cacttccttc acaaccaata attgatacaa cattagtaga ttaccctaaa     480

tattcaacga ccggtagtat aaattataat ggtacagcac ttcaattaat gggatggaca     540

ctcataccat gtattatggt atacgataaa acgatagctt ctacacacac tcaaattaca     600

acaacccctt attatatttt gaaaaaatat caacgttggg tacttgcaac aggaagtggt     660

ctatctgtac ctgcacatgt caaatcaact ttcgaatacg aatggggaac agacacagat     720

caaaaaacca gtgtaataaa tacattaggt tttcaaatta atacagatac aaaattaaaa     780

gctactgtac cagaagtagg tggaggtaca acagatataa gaacacaaat cactgaagaa     840

cttaaagtag aatatagtag tgaaaataaa gaaatgcgaa aatataaaca aagctttgac     900

gtagacaact taaattatga tgaagcacta aatgctgtag gatttattgt tgaaacttca     960

ttcgaattat atcgaatgaa tggaaatgtc cttataacaa gtataaaaac tacaaataaa    1020

gacacctata atacagttac ttatccaaat cataaagaag ttttattact tcttacaaat    1080

cattcttatg aagaagtaac agcactaact ggcatttcca aagaaagact tcaaaatctt    1140

aaaaacaatt ggaaaaaaag a                                              1161
```

<210> SEQ ID NO 2
<211> LENGTH: 387
<212> TYPE: PRT
<213> ORGANISM: Bacillus thuringiensis

<400> SEQUENCE: 2

```
Met Ile Glu Thr Asn Lys Ile Tyr Glu Ile Ser Asn Lys Ala Asn Gly
1               5                   10                  15

Leu Tyr Ala Thr Thr Tyr Leu Ser Phe Asp Asn Ser Gly Val Ser Leu
            20                  25                  30

Leu Asn Lys Asn Glu Ser Asp Ile Asn Asp Tyr Asn Leu Lys Trp Phe
        35                  40                  45

Leu Phe Pro Ile Asp Asn Asn Gln Tyr Ile Ile Thr Ser Tyr Gly Val
    50                  55                  60

Asn Lys Asn Lys Val Trp Thr Ala Asn Gly Asn Lys Ile Asn Val Thr
65                  70                  75                  80

Thr Tyr Ser Ala Glu Asn Ser Ala Gln Gln Trp Gln Ile Arg Asn Ser
                85                  90                  95

Ser Ser Gly Tyr Ile Ile Glu Asn Asn Asn Gly Lys Ile Leu Thr Ala
            100                 105                 110

Gly Thr Gly Gln Ser Leu Gly Leu Leu Tyr Leu Thr Asp Glu Ile Pro
        115                 120                 125

Glu Asp Ser Asn Gln Gln Trp Asn Leu Thr Ser Ile Gln Thr Ile Ser
    130                 135                 140

Leu Pro Ser Gln Pro Ile Ile Asp Thr Thr Leu Val Asp Tyr Pro Lys
145                 150                 155                 160

Tyr Ser Thr Thr Gly Ser Ile Asn Tyr Asn Gly Thr Ala Leu Gln Leu
```

-continued

```
                165                 170                 175

Met Gly Trp Thr Leu Ile Pro Cys Ile Met Val Tyr Asp Lys Thr Ile
            180                 185                 190

Ala Ser Thr His Thr Gln Ile Thr Thr Thr Pro Tyr Tyr Ile Leu Lys
        195                 200                 205

Lys Tyr Gln Arg Trp Val Leu Ala Thr Gly Ser Gly Leu Ser Val Pro
    210                 215                 220

Ala His Val Lys Ser Thr Phe Glu Tyr Glu Trp Gly Thr Asp Thr Asp
225                 230                 235                 240

Gln Lys Thr Ser Val Ile Asn Thr Leu Gly Phe Gln Ile Asn Thr Asp
                245                 250                 255

Thr Lys Leu Lys Ala Thr Val Pro Glu Val Gly Gly Gly Thr Thr Asp
            260                 265                 270

Ile Arg Thr Gln Ile Thr Glu Glu Leu Lys Val Glu Tyr Ser Ser Glu
        275                 280                 285

Asn Lys Glu Met Arg Lys Tyr Lys Gln Ser Phe Asp Val Asp Asn Leu
    290                 295                 300

Asn Tyr Asp Glu Ala Leu Asn Ala Val Gly Phe Ile Val Glu Thr Ser
305                 310                 315                 320

Phe Glu Leu Tyr Arg Met Asn Gly Asn Val Leu Ile Thr Ser Ile Lys
                325                 330                 335

Thr Thr Asn Lys Asp Thr Tyr Asn Thr Val Thr Tyr Pro Asn His Lys
            340                 345                 350

Glu Val Leu Leu Leu Leu Thr Asn His Ser Tyr Glu Glu Val Thr Ala
        355                 360                 365

Leu Thr Gly Ile Ser Lys Glu Arg Leu Gln Asn Leu Lys Asn Asn Trp
    370                 375                 380

Lys Lys Arg
385


<210> SEQ ID NO 3
<211> LENGTH: 396
<212> TYPE: DNA
<213> ORGANISM: Bacillus thuringiensis

<400> SEQUENCE: 3

atgtcagcac gtgaagtaca cattgaaata ataaatcata caggtcatac cttacaaatg      60

gataaaagaa ctagacttgc acatggtgaa tggattatta cacccgtgaa tgttccaaat     120

aattcttctg atttatttca agcaggttct gatggagttt tgacaggagt agaaggaata     180

ataatttata ctataaatgg agaaatagaa attaccttac attttgacaa tccttatgca     240

ggttctaata aatattctgg acgttctagt gatgatgatt ataaagttat aactgaagca     300

agagcagaac atagagctaa taatcatgat catgtaacat atacagttca aagaaacata     360

tcacgatata ccaataaatt atgttctaat aactcc                               396


<210> SEQ ID NO 4
<211> LENGTH: 132
<212> TYPE: PRT
<213> ORGANISM: Bacillus thuringiensis

<400> SEQUENCE: 4

Met Ser Ala Arg Glu Val His Ile Glu Ile Ile Asn His Thr Gly His
1               5                   10                  15

Thr Leu Gln Met Asp Lys Arg Thr Arg Leu Ala His Gly Glu Trp Ile
            20                  25                  30
```

```
Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Thr Leu His Phe Asp Asn Pro Tyr Ala
65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Val Gln Arg Asn Ile Ser Arg Tyr Thr Asn Lys Leu Cys
        115                 120                 125

Ser Asn Asn Ser
    130


<210> SEQ ID NO 5
<211> LENGTH: 402
<212> TYPE: DNA
<213> ORGANISM: Bacillus thuringiensis

<400> SEQUENCE: 5

aaggaacata catataaaaa ggggaaacct accgaaaaat attatcattt ttttaagtta      60

aatacataca ttaatttagt atctgtaaaa acattaattt tatggaggtt gatatttatg     120

tcagctcgcg aagtacacat tgaaataaac aataaaacac gtcatacatt acaattagag     180

gataaaacta aacttagcgg aggtagatgg cgaacatcac ctacaaatgt tgctcgtgat     240

acaattaaaa catttgtagc agaatcacat ggttttatga caggagtaga aggtattata     300

tattttagtg taaacggaga cgcagaaatt agtttacatt ttgacaatcc ttatatagtt     360

ctaataaatg tgatggttct tctgatagac ctgaatatga ag                        402


<210> SEQ ID NO 6
<211> LENGTH: 119
<212> TYPE: PRT
<213> ORGANISM: Bacillus thuringiensis

<400> SEQUENCE: 6

Met Ser Ala Arg Glu Val His Ile Glu Ile Asn Asn Lys Thr Arg His
1               5                   10                  15

Thr Leu Gln Leu Glu Asp Lys Thr Lys Leu Ser Gly Gly Arg Trp Arg
            20                  25                  30

Thr Ser Pro Thr Asn Val Ala Arg Asp Thr Ile Lys Thr Phe Val Ala
        35                  40                  45

Glu Ser His Gly Phe Met Thr Gly Val Glu Gly Ile Ile Tyr Phe Ser
    50                  55                  60

Val Asn Gly Asp Ala Glu Ile Ser Leu His Phe Asp Asn Pro Tyr Ile
65                  70                  75                  80

Gly Ser Asn Lys Cys Asp Gly Ser Ser Asp Lys Pro Glu Tyr Glu Val
                85                  90                  95

Ile Thr Gln Ser Gly Ser Gly Asp Lys Ser His Val Thr Tyr Thr Ile
            100                 105                 110

Gln Thr Val Ser Leu Arg Leu
        115


<210> SEQ ID NO 7
<211> LENGTH: 1155
```

<212> TYPE: DNA
<213> ORGANISM: Bacillus thuringiensis

<400> SEQUENCE: 7

```
atgttagata ctaataaagt ttatgaaata agcaatcttg ctaatggatt atatacatca     60
acttatttaa gtcttgatga ttcaggtgtt agtttaatga gtaaaaagga tgaagatatt    120
gatgattaca atttaaaatg gtttttattt cctattgata ataatcaata tattattaca    180
agctatggag ctaataattg taaagtttgg aatgttaaaa atgataaaat aaatgtttca    240
acttattctt caacaaactc tgtacaaaaa tggcaaataa aagctaaaga ttcttcatat    300
ataatacaaa gtgataatgg aaaggtctta acagcaggag taggtgaatc tcttggaata    360
gtacgcctaa ctgatgaatt tccagagaat tctaaccaac aatggaattt aactcctgta    420
caaacaattc aactcccaca aaaacctaaa atagatgaaa aattaaaaga tcatcctgaa    480
tattcagaaa ccggaaatat aaatcctaaa acaactcctc aattaatggg atggacatta    540
gtaccttgta ttatggtaaa tgattcagga atagataaaa acactcaaat taaaactact    600
ccatattata tttttaaaaa atataaatac tggaatctag caaaaggaag taatgtatct    660
ttacttccac atcaaaaaag atcatatgat tatgaatggg gtacagaaaa aaatcaaaaa    720
acatctatta ttaatacagt aggattgcaa attaatatag attcaggaat gaaatttgaa    780
gtaccagaag taggaggagg tacagaagac ataaaaacac aattaactga agaattaaaa    840
gttgaatata gcactgaaac caaaataatg acgaaatatc aagaacactc agagatagat    900
aatccaacta atcaaccaat gaattctata ggacttctta tttatacttc tttagaatta    960
tatcgatata acggtacaga aattaagata atggacatag aaacttcaga tcatgatact   1020
tacactctta cttcttatcc aaatcataaa gaagcattat tacttctcac aaaccattcg   1080
tatgaagaag tagaagaaat aacaaaaata cctaagcata cacttataaa attgaaaaaa   1140
cattatttta aaaaa                                                    1155
```

<210> SEQ ID NO 8
<211> LENGTH: 385
<212> TYPE: PRT
<213> ORGANISM: Bacillus thuringiensis

<400> SEQUENCE: 8

```
Met Leu Asp Thr Asn Lys Val Tyr Glu Ile Ser Asn Leu Ala Asn Gly
1               5                   10                  15

Leu Tyr Thr Ser Thr Tyr Leu Ser Leu Asp Asp Ser Gly Val Ser Leu
            20                  25                  30

Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Glu Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140
```

```
Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Gly Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Ser Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385


<210> SEQ ID NO 9
<211> LENGTH: 372
<212> TYPE: DNA
<213> ORGANISM: Bacillus thuringiensis

<400> SEQUENCE: 9

atgtcagcac gtgaagtaca cattaatgta aataataaga caggtcatac attacaatta      60

gaagataaaa caaaacttga tggtggtaga tggcgaacat cacctacaaa tgttgctaat     120

gatcaaatta aaacatttgt agcagaatca catggtttta tgacaggtac agaaggtcat     180

atatattata gtataaatgg agaagcagaa attagtttat attttgataa tccttattca     240

ggttctaata aatatgatgg gcattccaat aaacctcaat atgaagttac tacccaagga     300

ggatcaggaa atcaatctca tgttacgtat actattcaaa ctgcatcttc acgatatggg     360

aataactcat aa                                                         372


<210> SEQ ID NO 10
<211> LENGTH: 123
<212> TYPE: PRT
<213> ORGANISM: Bacillus thuringiensis

<400> SEQUENCE: 10
```

-continued

```
Met Ser Ala Arg Glu Val His Ile Asn Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly His Ile Tyr Tyr Ser
    50                  55                  60

Ile Asn Gly Glu Ala Glu Ile Ser Leu Tyr Phe Asp Asn Pro Tyr Ser
65                  70                  75                  80

Gly Ser Asn Lys Tyr Asp Gly His Ser Asn Lys Pro Gln Tyr Glu Val
                85                  90                  95

Thr Thr Gln Gly Gly Ser Gly Asn Gln Ser His Val Thr Tyr Thr Ile
            100                 105                 110

Gln Thr Ala Ser Ser Arg Tyr Gly Asn Asn Ser
        115                 120
```

<210> SEQ ID NO 11
<211> LENGTH: 1152
<212> TYPE: DNA
<213> ORGANISM: Bacillus thuringiensis

<400> SEQUENCE: 11

```
atgttagata ctaataaagt ttatgaaata agtaatcatg ctaatggact atatgcagca     60

acttatttaa gtttagatga ttcaggtgtt agtttaatga ataaaaatga tgatgatatt    120

gatgattata acttaaaatg gtttttattt cctattgatg atgatcaata tattattaca    180

agctatgcag caaataattg taaagtttgg aatgttaata atgataaaat aaatgtttcg    240

acttattctt caacaaattc aatacaaaaa tggcaaataa aagctaatgg ttcttcatat    300

gtaatacaaa gtgataatgg aaaagtctta acagcaggaa ccggtcaagc tcttggattg    360

atacgtttaa ctgatgaatc ctcaaataat cccaatcaac aatggaattt aacttctgta    420

caaacaattc aacttccaca aaaacctata atagatacaa aattaaaaga ttatcccaaa    480

tattcaccaa ctggaaatat agataatgga acatctcctc aattaatggg atggacatta    540

gtaccttgta ttatggtaaa tgatccaaat atagataaaa atactcaaat taaaactact    600

ccatattata ttttaaaaaa atatcaatat tggcaacgag cagtaggaag taatgtagct    660

ttacgtccac atgaaaaaaa atcatatact tatgaatggg gaacagaaat agatcaaaaa    720

acaacaatca taaatacatt aggatttcaa atcaatatag attcaggaat gaaatttgat    780

ataccagaag taggtggagg tacagatgaa ataaaaacac aactaaatga agaattaaaa    840

atagaatata gtcgtgaaac taaaataatg gaaaaatatc aagaacaatc tgaaatagat    900

aatccaactg atcaaccaat gaattctata ggatttctta ctattacttc tttagaatta    960

tatagatata atggctcaga aattcgtata atgcaaattc aaacctcaga taatgatact   1020

tataatgtta cttcttatcc agatcatcaa caagctttat tacttcttac aaatcattca   1080

tatgaagaag tagaagaaat aacaaatatt cctaaaagta cactaaaaaa attaaaaaaa   1140

tattattttt aa                                                        1152
```

<210> SEQ ID NO 12
<211> LENGTH: 383
<212> TYPE: PRT
<213> ORGANISM: Bacillus thuringiensis

<400> SEQUENCE: 12

-continued

```
Met Leu Asp Thr Asn Lys Val Tyr Glu Ile Ser Asn His Ala Asn Gly
1               5                   10                  15

Leu Tyr Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Lys Trp Phe
        35                  40                  45

Leu Phe Pro Ile Asp Asp Asp Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Pro Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ser Thr Leu Lys Lys Leu Lys Lys Tyr Tyr Phe
    370                 375                 380
```

<210> SEQ ID NO 13
<211> LENGTH: 1952
<212> TYPE: DNA
<213> ORGANISM: Bacillus thuringiensis
<220> FEATURE:

-continued

<221> NAME/KEY: misc_feature
<222> LOCATION: (1903)..(1903)
<223> OTHER INFORMATION: N= any A,C,T, or G
<220> FEATURE:
<221> NAME/KEY: misc_feature
<222> LOCATION: (1932)..(1932)
<223> OTHER INFORMATION: N= any A,C,T, or G

<400> SEQUENCE: 13

```
aaaatctttt acatatattt gttaggaagc atgaaaataa aaatagatta tatagaagga     60

gtgaaataga tgaatgtaaa tcacggtatg tcttgtggat gtggttgcca gcaaggtaaa    120

gaagaatata acgattatca tgtgtcaaat gaatataggg acgaaaatcc tagtacaact    180

tgtaattctc aacaaggtaa ttatgagtac gaacaaagta aagaaacata taacaatgat    240

tatcaatcat atgaatacaa tcaacaaaat tataatactt gcggaaggaa tcaaggaacg    300

atggaacagg agtcgatgca aaaggatagg aattgggaga atgcaaatta tagtggatat    360

gatggatgta gtccaaatca gttgaatgca ctaaatttac cagatgaaag tactaggttt    420

caaaaaataa ctaatgtaaa tactcgtgat agtcatcgtg ttttagacat gatggacgtt    480

cctagtggaa ctaggcttga tactcgtgta cctcctattt gtagtcaaac cgaatttaca    540

aatacggtta gtaatgaatt agtttccacg aatcatgata cacaattttt aatttttttat    600

caaacagatg atagttcatt tattattggg aatcgaggaa atggtcgagt tttagatgtt    660

tttcctagta atagaaatgg ttatacaata gtttcaaatg tgtatagtgg ttcaaggaat    720

aatcagcgtt ttcgtatgaa taaagcatct aataatcaat ttagtttaca aaccattttt    780

aaggacagag taaatatatg tggtcatatt cacaatttta acgcgataat tacagctact    840

actttaggtg agaatgatag taatgcttta tttcaagtac aatcttccac aaatataaca    900

ctacctacat taccacctag gacaacatta gaaccaccaa gagcattaac aaatataaat    960

gatacaggtg attctccagc gcaagcacct cgagcggtag aaggaagtgt tcttatcccc   1020

gcaatagcgg taaatgatgt cattccggta gcgcaaagaa tgcaagaaag tccgtattat   1080

gtgttaacat ataatacata ttggcataga gttatttcag caatactacc aggtagtggg   1140

caaactacaa ggttcgatgt aaacttacca ggtcctaatc aaagtacaat ggtagatgta   1200

ttagatacag caattactgc agattttaga ttacaatttg ttggaagtgg acgaacaaat   1260

gtatttcaac aacaaattag aaatggatta aatatattaa attctacaac gtctcatcgt   1320

ttaggagatg aaacacgtaa ttgggatttt acaaatagag gtgctcaagg aagattagcg   1380

tttttttgtaa aagcacatga gtttgtatta acacgtgcga atggaacacg agtaagtgat   1440

ccatgggtgg cattagatcc gaatgttaca gctgctcaaa catttggagg agtattactt   1500

acattagaaa aagaaaaaat agtatgtgca agtaatagtt ataatttatc agtatggaaa   1560

acaccaatgg aaataaagaa tggaaaaatt tatacaaaaa atgaatggaa tacaaaacca   1620

aactacaaat aaacaaaatg attctgttga caagtttgaa aaaacaaaaa ttggtttgca   1680

aaatatggtt ccggtgcaaa aattccaaaa tgattgaaaa ggatttatca aacttgtcca   1740

tactggtact actacttaaa aaaggtgtgt gattagtatg ggaccagaaa atttatttaa   1800

gtggaaacat tatcaaccag atattatttt atcaacagta cgttggtacc tacggtacaa   1860

cttaagtttt cgtgatttgg tagaaatgat ggaggaacga ggnttatctt tggctcatac   1920

aaccattatg cngttgggtt catcaatatg gt                                 1952
```

<210> SEQ ID NO 14
<211> LENGTH: 520

-continued

```
<212> TYPE: PRT
<213> ORGANISM: Bacillus thuringiensis

<400> SEQUENCE: 14

Met Asn Val Asn His Gly Met Ser Cys Gly Cys Gly Cys Gln Gln Gly
1               5                   10                  15

Lys Glu Glu Tyr Asn Asp Tyr His Val Ser Asn Glu Tyr Arg Asp Glu
            20                  25                  30

Asn Pro Ser Thr Thr Cys Asn Ser Gln Gln Gly Asn Tyr Glu Tyr Glu
        35                  40                  45

Gln Ser Lys Glu Thr Tyr Asn Asn Asp Tyr Gln Ser Tyr Glu Tyr Asn
    50                  55                  60

Gln Gln Asn Tyr Asn Thr Cys Gly Arg Asn Gln Gly Thr Met Glu Gln
65                  70                  75                  80

Glu Ser Met Gln Lys Asp Arg Asn Trp Glu Asn Ala Asn Tyr Ser Gly
                85                  90                  95

Tyr Asp Gly Cys Ser Pro Asn Gln Leu Asn Ala Leu Asn Leu Pro Asp
            100                 105                 110

Glu Ser Thr Arg Phe Gln Lys Ile Thr Asn Val Asn Thr Arg Asp Ser
        115                 120                 125

His Arg Val Leu Asp Met Met Asp Val Pro Ser Gly Thr Arg Leu Asp
    130                 135                 140

Thr Arg Val Pro Pro Ile Cys Ser Gln Thr Glu Phe Thr Asn Thr Val
145                 150                 155                 160

Ser Asn Glu Leu Val Ser Thr Asn His Asp Thr Gln Phe Leu Ile Phe
                165                 170                 175

Tyr Gln Thr Asp Asp Ser Ser Phe Ile Ile Gly Asn Arg Gly Asn Gly
            180                 185                 190

Arg Val Leu Asp Val Phe Pro Ser Asn Arg Asn Gly Tyr Thr Ile Val
        195                 200                 205

Ser Asn Val Tyr Ser Gly Ser Arg Asn Asn Gln Arg Phe Arg Met Asn
    210                 215                 220

Lys Ala Ser Asn Asn Gln Phe Ser Leu Gln Thr Ile Phe Lys Asp Arg
225                 230                 235                 240

Val Asn Ile Cys Gly His Ile His Asn Phe Asn Ala Ile Ile Thr Ala
                245                 250                 255

Thr Thr Leu Gly Glu Asn Asp Ser Asn Ala Leu Phe Gln Val Gln Ser
            260                 265                 270

Ser Thr Asn Ile Thr Leu Pro Thr Leu Pro Pro Arg Thr Thr Leu Glu
        275                 280                 285

Pro Pro Arg Ala Leu Thr Asn Ile Asn Asp Thr Gly Asp Ser Pro Ala
    290                 295                 300

Gln Ala Pro Arg Ala Val Glu Gly Ser Val Leu Ile Pro Ala Ile Ala
305                 310                 315                 320

Val Asn Asp Val Ile Pro Val Ala Gln Arg Met Gln Glu Ser Pro Tyr
                325                 330                 335

Tyr Val Leu Thr Tyr Asn Thr Tyr Trp His Arg Val Ile Ser Ala Ile
            340                 345                 350

Leu Pro Gly Ser Gly Gln Thr Thr Arg Phe Asp Val Asn Leu Pro Gly
        355                 360                 365

Pro Asn Gln Ser Thr Met Val Asp Val Leu Asp Thr Ala Ile Thr Ala
    370                 375                 380

Asp Phe Arg Leu Gln Phe Val Gly Ser Gly Arg Thr Asn Val Phe Gln
385                 390                 395                 400
```

-continued

```
Gln Gln Ile Arg Asn Gly Leu Asn Ile Leu Asn Ser Thr Thr Ser His
                405                 410                 415

Arg Leu Gly Asp Glu Thr Arg Asn Trp Asp Phe Thr Asn Arg Gly Ala
            420                 425                 430

Gln Gly Arg Leu Ala Phe Phe Val Lys Ala His Glu Phe Val Leu Thr
        435                 440                 445

Arg Ala Asn Gly Thr Arg Val Ser Asp Pro Trp Val Ala Leu Asp Pro
    450                 455                 460

Asn Val Thr Ala Ala Gln Thr Phe Gly Gly Val Leu Leu Thr Leu Glu
465                 470                 475                 480

Lys Glu Lys Ile Val Cys Ala Ser Asn Ser Tyr Asn Leu Ser Val Trp
                485                 490                 495

Lys Thr Pro Met Glu Ile Lys Asn Gly Lys Ile Tyr Thr Lys Asn Glu
            500                 505                 510

Trp Asn Thr Lys Pro Asn Tyr Lys
        515                 520
```

<210> SEQ ID NO 15
<211> LENGTH: 1024
<212> TYPE: DNA
<213> ORGANISM: Bacillus thuringiensis

<400> SEQUENCE: 15

```
agtgcgagca tttattaata caatagaaat gctcacatat gtaacaacct ttagtatatt     60

taaatataag gagttgtata acttgagtat cttaaatctt caagacttat cacaaaaata    120

tatgactgca gctttaaata agataaatcc aaaaaaagta ggtactttcc attttgagga    180

accaatagta ctttcagaat cttctactcc cacacgttct gaaattgatg cccctcttaa    240

tgttatgttt cacgcttcac aagatcttga taatagaagg ggcactagtg atttaaaaca    300

aactgtttct ttttctcaaa ctcaaataaa tactgttgaa accaaaacta ctgatggtgt    360

taaaacaact aaagaacata catttagtgg tacattagaa ctaaagatta aatatgcaat    420

gtttgattta gggggagtgt caggcacata tcaatataaa aaaagtactg aaaacgatat    480

tagttcagaa aagagtaaat cgaagtcaga ttctcaaact tggtcaatat caagtgaata    540

tacagttaaa cctggagtaa aagaaactct tcatttttat attgtaggaa taaaaaaccg    600

aagtgccttt taaatatttt tgctgaattt caaggtacta aaactattga taatgtatcc    660

aatgttatgg cttatcaaga gtttataagt caagatgatg aacatataag agcatgtatg    720

aaagcaagta aattggctaa tcctgatcat ctttcaggat atacagctcc aaaggaatta    780

aaagcaaata caagtaaagg atcagtagaa tttagaggta cagctatagc taaaataaat    840

acaggagtaa aatgtcttgt tgtagttaat ggaaaaaatt caataactgg aaaaacttat    900

tcttatatac atcctaaaac aatgttagct gatggaacca ttgaatattt agaaagtgag    960

atagatcttt tagaaagtga gatagatctt ttaactacaa gtagtatttt agtttaaaca   1020

atta                                                                1024
```

<210> SEQ ID NO 16
<211> LENGTH: 310
<212> TYPE: PRT
<213> ORGANISM: Bacillus thuringiensis

<400> SEQUENCE: 16

```
Met Ser Ile Leu Asn Leu Gln Asp Leu Ser Gln Lys Tyr Met Thr Ala
1               5                   10                  15
```

```
Ala Leu Asn Lys Ile Asn Pro Lys Lys Val Gly Thr Phe His Phe Glu
            20                  25                  30

Glu Pro Ile Val Leu Ser Glu Ser Ser Thr Pro Thr Arg Ser Glu Ile
        35                  40                  45

Asp Ala Pro Leu Asn Val Met Phe His Ala Ser Gln Asp Leu Asp Asn
    50                  55                  60

Arg Arg Gly Thr Ser Asp Leu Lys Gln Thr Val Ser Phe Ser Gln Thr
65                  70                  75                  80

Gln Ile Asn Thr Val Glu Thr Lys Thr Thr Asp Gly Val Lys Thr Thr
                85                  90                  95

Lys Glu His Thr Phe Ser Gly Thr Leu Glu Leu Lys Ile Lys Tyr Ala
            100                 105                 110

Met Phe Asp Leu Gly Gly Val Ser Gly Thr Tyr Gln Tyr Lys Lys Ser
        115                 120                 125

Thr Glu Asn Asp Ile Ser Ser Glu Lys Ser Lys Ser Lys Ser Asp Ser
    130                 135                 140

Gln Thr Trp Ser Ile Ser Ser Glu Tyr Thr Val Lys Pro Gly Val Lys
145                 150                 155                 160

Glu Thr Leu Asp Phe Tyr Ile Val Gly Ile Lys Thr Glu Val Pro Leu
                165                 170                 175

Asn Ile Phe Ala Glu Phe Gln Gly Thr Lys Thr Ile Asp Asn Val Ser
            180                 185                 190

Asn Val Met Ala Tyr Gln Glu Phe Ile Ser Gln Asp Asp Glu His Ile
        195                 200                 205

Arg Ala Cys Met Lys Ala Ser Lys Leu Ala Asn Pro Asp His Leu Ser
    210                 215                 220

Gly Tyr Thr Ala Pro Lys Glu Leu Lys Ala Asn Thr Ser Lys Gly Ser
225                 230                 235                 240

Val Glu Phe Arg Gly Thr Ala Ile Ala Lys Ile Asn Thr Gly Val Lys
                245                 250                 255

Cys Leu Val Val Val Asn Gly Lys Asn Ser Ile Thr Gly Lys Thr Tyr
            260                 265                 270

Ser Tyr Ile His Pro Lys Thr Met Leu Ala Asp Gly Thr Ile Glu Tyr
        275                 280                 285

Leu Glu Ser Glu Ile Asp Leu Leu Glu Ser Glu Ile Asp Leu Leu Thr
    290                 295                 300

Thr Ser Ser Ile Leu Val
305                 310
```

<210> SEQ ID NO 17
<211> LENGTH: 3607
<212> TYPE: DNA
<213> ORGANISM: Bacillus thuringiensis

<400> SEQUENCE: 17

```
gaattcttaa aaaaaataag gttttttatg gaaaattgtc ggaaagctgt atgttttgtg     60

aatagataag tatatttttt aaaattaatt tatataaaat atataatatc aacgagtgaa    120

tatatagcat tgtctaatta tagataaaag agcttatttt tttcacatat aaactactta    180

ttacgtatag tacagtgaga caatttttaa cagttgtttc atataaccct ccattcattt    240

tataagagca aaaaaacaaa cacgcttatg aaaaggaata tttgtttttc atttattatt    300

tatttcaaga aaattgaaat gtgtatatat gattaagcaa catttggagt tgtttttgat    360

tctcctctta ttcaaattgc cggagtttaa aattcaaata aatttattga tgtatattac    420
```

```
tcttctgaag atgataatct taaatattac caattgataa aagttgaatc tcattttgta    480
caaactacct ttagcaaaca gttgatgaaa gagcgtggaa aaattaaaca atagtttagt    540
catttcaaag ataaagggct ggaacagcca cgttgatatg gttaaaatcg ctatctattg    600
catatatatt tttagtaaat aactttttat tattaaaaat ataattttat aaaggatgtg    660
tttaagtttg actatcataa atatattaga ttatgcagat tcttatttaa gagctgctat    720
taaaaaatat ggaggatacc caagttctag taaagctaga ttcttatcta ctccaaaaat    780
ttcagaacca gagtggtatt accctgctaa agaatctgtt aatgcatatg aaattggtaa    840
acaatctggt tcgtatccta atcattcttc tacatctcaa aattttaatg taccaattcg    900
ttatcctgtt tccactacta gttcaacaaa aactataaat ggttttaaaa cagataaaag    960
tatttctaaa aatttaaatc ttaacttagg gataaatgca aaaataccta atataaatat   1020
tcctggtggc tttgaaattg aagttaaacc tggagctgag gtttcaagaa atgttaaaac   1080
gaatcaaaca gtagacttta gtagtacttc tgaaaaaaca caaaatacaa atgacactcc   1140
atctgacaca actcaatctt tctcttgtcc tcctaacaca aaagcaacat atatagttat   1200
ttatttcggg ggagaaccta aagtagaagt tacagctgta acagatataa taggaaatgg   1260
atctggaata ggaacagatc ctactactgg tcaagaaaaa tcgcaaagaa atgttttagc   1320
aactttagat tacagtaaag aaggtcaagc tggtaaaaaa tatactatga tggtaactgc   1380
agatcaatta gcaactaaaa tacctggata taatcctcca ccaagagtcg aacaagatcg   1440
tagtcataat gcattaacta ttcatagtga ccttatagta aatttaaaag aagattttgc   1500
atatgaaata attgtaaaat ttgaaaattt atcttattcg acacttttta atgaagatct   1560
ctttatttat agattcgaca aaaatcataa tcttcttata gaaaaaacag ttggatcatt   1620
atttgaaact aatctacatg cagatatttt ttatgaacat attgaaagtg aattagaata   1680
aaaatatttt tttaaatatg ataactccac ttatttaaaa tcacaaaagt tttaaacaaa   1740
attaacaaaa aaattaaatg gaggttgaaa atatgtcagc acgtgaagta cacattgaaa   1800
taataaatca tacaggtcat accttacaaa tggataaaag aactagactt gcacatggtg   1860
aatggattat tacacccgtg aatgttccaa ataattcttc tgatttattt caagcaggtt   1920
ctgatggagt tttgacagga gtagaaggaa taataattta tactataaat ggagaaatag   1980
aaattacctt acattttgac aatccttatg caggttctaa taaatattct ggacgttcta   2040
gtgatgatga ttataaagtt ataactgaag caagagcaga acatagagct aataatcatg   2100
atcatgtaac atatacagtt caaagaaaca tatcacgata taccaataaa ttatgttcta   2160
ataactccta aaatttattt taattattaa aaacaaagtt ctataaattt gaataaagaa   2220
ctttgttttt atttgaaaaa atcacaaaaa ggtgtgtgaa attatgatag aaactaataa   2280
gatatatgaa ataagcaata aagctaatgg attatatgca actacttatt taagttttga   2340
taattcaggt gttagtttat taaataaaaa tgaatctgat attaatgatt ataatttgaa   2400
atggttttta tttcctattg ataataatca gtatattatt acaagttatg gagtaaataa   2460
aaataaggtt tggactgcta atggtaataa aataaatgtt acaacatatt ccgcagaaaa   2520
ttcagcacaa caatggcaaa taagaaacag ttcttctgga tatataatag aaaataataa   2580
tgggaaaatt ttaacggcag gaacaggcca atcattaggt ttattatatt taactgatga   2640
aatacctgaa gattctaatc aacaatggaa tttaacttca atacaaacaa tttcacttcc   2700
ttcacaacca ataattgata caacattagt agattaccct aaatattcaa cgaccggtag   2760
```

-continued

```
tataaattat aatggtacag cacttcaatt aatgggatgg acactcatac catgtattat   2820

ggtatacgat aaaacgatag cttctacaca cactcaaatt acaacaaccc cttattatat   2880

tttgaaaaaa tatcaacgtt gggtacttgc aacaggaagt ggtctatctg tacctgcaca   2940

tgtcaaatca actttcgaat acgaatgggg aacagacaca gatcaaaaaa ccagtgtaat   3000

aaatacatta ggttttcaaa ttaatacaga tacaaaatta aaagctactg taccagaagt   3060

aggtggaggt acaacagata taagaacaca aatcactgaa gaacttaaag tagaatatag   3120

tagtgaaaat aaagaaatgc gaaaatataa acaaagcttt gacgtagaca acttaaatta   3180

tgatgaagca ctaaatgctg taggatttat tgttgaaact tcattcgaat tatatcgaat   3240

gaatggaaat gtccttataa caagtataaa aactacaaat aaagacacct ataatacagt   3300

tacttatcca aatcataaag aagttttatt acttcttaca aatcattctt atgaagaagt   3360

aacagcacta actggcattt ccaaagaaag acttcaaaat cttaaaaaca attggaaaaa   3420

aagataaaat atatatagag ttaaaagttc cgtaaggaac ggggagtgtt tttgagaaga   3480

acactaaaaa agtcggtttt ttaattttca cctaaaggca aagacaatcc ctcagaagcg   3540

tctagaagct tgtatagagc gtttaaaagt atgtttagat aaaatactag ggaaaagtag   3600

tgaattc                                                             3607
```

<210> SEQ ID NO 18
<211> LENGTH: 1026
<212> TYPE: DNA
<213> ORGANISM: Bacillus thuringiensis

<400> SEQUENCE: 18

```
atgtgtttaa gtttgactat cataaatata ttagattatg cagattctta tttaagagct     60

gctattaaaa aatatggagg atacccaagt tctagtaaag ctagattctt atctactcca    120

aaaatttcag aaccagagtg gtattaccct gctaaagaat ctgttaatgc atatgaaatt    180

ggtaaacaat ctggttcgta tcctaatcat tcttctacat ctcaaaattt taatgtacca    240

attcgttatc ctgtttccac tactagttca acaaaaacta taaatggttt taaaacagat    300

aaaagtattt ctaaaaattt aaatcttaac ttagggataa atgcaaaaat acctaatata    360

aatattcctg gtggctttga aattgaagtt aaacctggag ctgaggtttc aagaaatgtt    420

aaaacgaatc aaacagtaga ctttagtagt acttctgaaa aaacacaaaa tacaaatgac    480

actccatctg acacaactca atctttctct tgtcctccta acacaaaagc aacatatata    540

gttatttatt tcgggggaga acctaaagta gaagttacag ctgtaacaga tataatagga    600

aatggatctg gaataggaac agatcctact actggtcaag aaaaatcgca aagaaatgtt    660

ttagcaactt tagattacag taaagaaggt caagctggta aaaaatatac tatgatggta    720

actgcagatc aattagcaac taaaatacct ggatataatc ctccaccaag agtcgaacaa    780

gatcgtagtc ataatgcatt aactattcat agtgacctta tagtaaattt aaaagaagat    840

tttgcatatg aaataattgt aaaatttgaa aatttatctt attcgacact ttttaatgaa    900

gatctcttta tttatagatt cgacaaaaat cataatcttc ttatagaaaa aacagttgga    960

tcattatttg aaactaatct acatgcagat attttttatg aacatattga aagtgaatta   1020

gaataa                                                              1026
```

<210> SEQ ID NO 19
<211> LENGTH: 341
<212> TYPE: PRT
<213> ORGANISM: Bacillus thuringiensis -continued

<400> SEQUENCE: 19

```
Met Cys Leu Ser Leu Thr Ile Ile Asn Ile Leu Asp Tyr Ala Asp Ser
1               5                   10                  15

Tyr Leu Arg Ala Ala Ile Lys Lys Tyr Gly Gly Tyr Pro Ser Ser Ser
            20                  25                  30

Lys Ala Arg Phe Leu Ser Thr Pro Lys Ile Ser Glu Pro Glu Trp Tyr
        35                  40                  45

Tyr Pro Ala Lys Glu Ser Val Asn Ala Tyr Glu Ile Gly Lys Gln Ser
    50                  55                  60

Gly Ser Tyr Pro Asn His Ser Ser Thr Ser Gln Asn Phe Asn Val Pro
65                  70                  75                  80

Ile Arg Tyr Pro Val Ser Thr Thr Ser Ser Thr Lys Thr Ile Asn Gly
                85                  90                  95

Phe Lys Thr Asp Lys Ser Ile Ser Lys Asn Leu Asn Leu Asn Leu Gly
            100                 105                 110

Ile Asn Ala Lys Ile Pro Asn Ile Asn Ile Pro Gly Gly Phe Glu Ile
        115                 120                 125

Glu Val Lys Pro Gly Ala Glu Val Ser Arg Asn Val Lys Thr Asn Gln
    130                 135                 140

Thr Val Asp Phe Ser Ser Thr Ser Glu Lys Thr Gln Asn Thr Asn Asp
145                 150                 155                 160

Thr Pro Ser Asp Thr Thr Gln Ser Phe Ser Cys Pro Pro Asn Thr Lys
                165                 170                 175

Ala Thr Tyr Ile Val Ile Tyr Phe Gly Gly Glu Pro Lys Val Glu Val
            180                 185                 190

Thr Ala Val Thr Asp Ile Ile Gly Asn Gly Ser Gly Ile Gly Thr Asp
        195                 200                 205

Pro Thr Thr Gly Gln Glu Lys Ser Gln Arg Asn Val Leu Ala Thr Leu
    210                 215                 220

Asp Tyr Ser Lys Glu Gly Gln Ala Gly Lys Lys Tyr Thr Met Met Val
225                 230                 235                 240

Thr Ala Asp Gln Leu Ala Thr Lys Ile Pro Gly Tyr Asn Pro Pro Pro
                245                 250                 255

Arg Val Glu Gln Asp Arg Ser His Asn Ala Leu Thr Ile His Ser Asp
            260                 265                 270

Leu Ile Val Asn Leu Lys Glu Asp Phe Ala Tyr Glu Ile Ile Val Lys
        275                 280                 285

Phe Glu Asn Leu Ser Tyr Ser Thr Leu Phe Asn Glu Asp Leu Phe Ile
    290                 295                 300

Tyr Arg Phe Asp Lys Asn His Asn Leu Leu Ile Glu Lys Thr Val Gly
305                 310                 315                 320

Ser Leu Phe Glu Thr Asn Leu His Ala Asp Ile Phe Tyr Glu His Ile
                325                 330                 335

Glu Ser Glu Leu Glu
            340
```

<210> SEQ ID NO 20
<211> LENGTH: 15
<212> TYPE: PRT
<213> ORGANISM: Bacillus thuringiensis

<400> SEQUENCE: 20

```
Met Leu Asp Thr Asn Lys Val Tyr Glu Ile Ser Asn His Ala Asn
1               5                   10                  15
```

<210> SEQ ID NO 21
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 21
atgttagata caaataaagt atatgaaatt tcaaatcatg c 41

<210> SEQ ID NO 22
<211> LENGTH: 20
<212> TYPE: PRT
<213> ORGANISM: Bacillus thuringiensis

<400> SEQUENCE: 22

Ser Ile Leu Asn Leu Gln Asp Leu Ser Gln Lys Tyr Met Thr Ala Ala
1 5 10 15

Leu Asn Lys Ile
20

<210> SEQ ID NO 23
<211> LENGTH: 15
<212> TYPE: PRT
<213> ORGANISM: Bacillus thuringiensis

<400> SEQUENCE: 23

Ser Ala Arg Gln Val His Ile Gln Ile Asn Asn Lys Thr Arg His
1 5 10 15

<210> SEQ ID NO 24
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 24
tcacaaaaat atatgaacag c 21

<210> SEQ ID NO 25
<211> LENGTH: 31
<212> TYPE: DNA
<213> ORGANISM: Artificial Sequence
<220> FEATURE:
<223> OTHER INFORMATION: Synthetic Oligonucleotide

SEQUENCE: 25 atatctatag aattcgcaat tcgtccatgt g 31

<210> SEQ ID NO 26
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 26
cagtattcat ataagcttcc tcctttaata 30

<210> SEQ ID NO 27
<211> LENGTH: 39
<212> TYPE: DNA

<213> ORGANISM: Artificial Sequence
<220> FEATURE:
<223> OTHER INFORMATION: Synthetic Oligonucleotide

<400> SEQUENCE: 27
aaggtgaagc ttttatgtta gatactaata aagtttatg 39

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 28
ccggaataga agctttgcat atgg 24

<210> SEQ ID NO 29
<211> LENGTH: 11
<212> TYPE: PRT
<213> ORGANISM: Bacillus thuringiensis

<400> SEQUENCE: 29

Met Asn Val Asn His Gly Met Ser Cys Gly Cys
1 5 10

<210> SEQ ID NO 30
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (22)..(22)
<223> OTHER INFORMATION: W = A or T
<220> FEATURE:
<221> NAME/KEY: misc_feature
<222> LOCATION: (23)..(23)
<223> OTHER INFORMATION: S = G or C
<220> FEATURE:
<221> NAME/KEY: misc_feature
<222> LOCATION: (24)..(24)
<223> OTHER INFORMATION: N = A, C, G or T

<400> SEQUENCE: 30
atgaatgtaa atcatgggat gwsntgt 27

<210> SEQ ID NO 31
<211> LENGTH: 12
<212> TYPE: RNA
<213> ORGANISM: Artificial Sequence
<220> FEATURE:
<223> OTHER INFORMATION: Synthetic Oligonucleotide

<400> SEQUENCE: 31
uaaacaaugg cu 12

<210> SEQ ID NO 32
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 32
gtaccagaag taggagg 17

-continued

```
<210> SEQ ID NO 33
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 33

tgacacagct atggagc                                                    17


<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34

atgattgccg gaatagaagc                                                 20
```